(12) United States Patent
Svendesn et al.

(10) Patent No.: US 8,309,337 B2
(45) Date of Patent: Nov. 13, 2012

(54) HYBRID POLYPEPTIDE OF A MALTOGENIC ALPHA-AMYLASE AND A CYCLODEXTRIN GLUCANOTRANSFERASE

(75) Inventors: Allan Svendesn, Horsholm (DK); Lars Beier, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/197,167

(22) Filed: Aug. 3, 2011

(65) Prior Publication Data

US 2011/0287142 A1 Nov. 24, 2011

Related U.S. Application Data

(63) Continuation of application No. 12/703,986, filed on Feb. 11, 2010, now Pat. No. 8,017,371, which is a continuation of application No. 11/624,750, filed on Jan. 19, 2007, now abandoned, which is a continuation-in-part of application No. PCT/DK2005/000515, filed on Aug. 2, 2005.

(60) Provisional application No. 60/598,150, filed on Aug. 2, 2004.

(51) Int. Cl.
*C12N 9/26* (2006.01)
*A21D 10/00* (2006.01)

(52) U.S. Cl. ......................... 435/201; 426/549
(58) Field of Classification Search .................. None
See application file for complete search history.

(56) References Cited

U.S. PATENT DOCUMENTS

| | | | |
|---|---|---|---|
| 5,631,149 A | 5/1997 | Matsui et al. | |
| 6,004,790 A * | 12/1999 | Dijkhuizen et al. | 435/193 |
| 6,162,628 A | 12/2000 | Cherry et al. | |
| 6,368,805 B1 | 4/2002 | Borchert et al. | |
| 6,482,622 B1 | 11/2002 | Cherry et al. | |
| 6,940,002 B1 | 9/2005 | Nielsen et al. | |
| 7,348,470 B2 | 3/2008 | Nielsen et al. | |
| 8,017,371 B2 * | 9/2011 | Svendesn et al. | 435/201 |
| 2003/0199072 A1 | 10/2003 | Crennell et al. | |

FOREIGN PATENT DOCUMENTS

| | | |
|---|---|---|
| WO | WO 95-22625 | 8/1995 |
| WO | WO 96-33267 | 10/1996 |
| WO | WO 99-19467 | 4/1999 |
| WO | WO 99-43793 | 9/1999 |
| WO | WO 99-43794 | 9/1999 |
| WO | WO 01-16349 | 3/2001 |
| WO | WO 03-073238 | 9/2003 |
| WO | WO 2004-026043 | 4/2004 |
| WO | WO 2005-003337 | 1/2005 |

OTHER PUBLICATIONS

Beier et al, Prot Eng, vol. 13 No. 7, pp. 509-513 (2000).
Dauter et al, Biochemistry, vol. 38, pp. 8385-8392 (1999).
Eyal et al, Proteins, vol. 50, No. 2, pp. 272-282 (2003).
Gujral et al, Cereal Chem, vol. 80, No. 6, pp. 750-754 (2003).
Kim et al, Appl Environ Microbiol, vol. 69, No. 8, pp. 4866-4874 (2003).
Lee et al, J Agric Food Chem, vol. 50, pp. 1411-1415 (2002).
Leemhuis et al, Biochemistry, vol. 42, pp. 7518-7526 (2003).
Leemhuis et al, J Appl Glycosci, vol. 50, No. 2, pp. 263-271 (2003).
Leemhuis et al, J Biotechnol, vol. 103, pp. 203-212 (2003).
Leemhuis, Univ Lib Groningen Chap 8, pp. 117-127 (1973).
Ma et al, Biochim Biophys Acta, vol. 1777, pp. 317-326 (2008).
Morrison et al, Cur Op Chem Biol, vol. 5, No. 3, pp. 302-307 (2001).
Ness et al, Nat Biotechnol, vol. 20, pp. 1251-1255 (2002).
Numata et al, Biochim Biophys Acta, vol. 1545, No. 1-2, pp. 174-183 (2001).
Ohdan et al, Appl Environ Microbiol, vol. 66, No. 7, pp. 3058-3064 (2000).
Penninga et al, J Biol Chem, vol. 271, No. 51, pp. 32777-32784 (1996).
Przylas et al, J Mol Biol, vol. 296, pp. 873-886 (2000).
Saraf et al, PNAS, vol. 101, No. 12, pp. 4142-4147 (2004).
Shim et al, Prot Eng Design Struc, vol. 17, No. 3, pp. 205-211 (2004).
Svensson, Plant Mol Biol 25(2), 141-157 (1994).
Tao, Enzym Biomass Cony, pp. 372-383 (1991).
Tonkova, Enzym Microbiol Technol, vol. 22, pp. 678-686 (1998).
Vajda et al, Biopolymers, vol. 33, No. 1, pp. 173-192 (1993).
Wind et al, 1998, FEBS, Eur J Biochem 253(3), 598-605 (1998).
Sequence 17 from Patent WO2005003337 (Jan. 25, 2005).
AAB74216 Standard Protein 719AA, (May 23, 2001).

* cited by examiner

*Primary Examiner* — David J Steadman
(74) *Attorney, Agent, or Firm* — Kristin J. McNamara

(57) ABSTRACT

The inventors realized that the diversity generated by conventional methods may be limited by steric hindrance between amino acid residues in the three-dimensional structures of the resulting polypeptides. The steric hindrance may occur between amino acid residues at widely different positions in the amino acid sequences, e.g. between residues in two different domains of the 3D structure, and resulting polypeptides which include such steric hindrance may never be observed in the conventional recombination methods because they may be expressed in poor yields or may have poor activity or stability. The inventors developed a method to identify and alleviate such steric hindrance in the resulting polypeptides. In an alignment of the three-dimensional structures, steric hindrance is indicated when residues from two different structures are located within a certain distance. Pairs of residues at corresponding positions in the amino acid sequences are not considered, and residues close to the surface (high solvent accessibility) are considered to be less prone to steric hindrance.

7 Claims, 8 Drawing Sheets

```
                      1                                                                  50
SEQ ID NO:  1   MSKKTLKRLL ALVVVLFILS GSGILDFSIT SANAQQATDR SNSVNYSTDG
SEQ ID NO:  2   MRKKTLKRLL TLVVGLVILS GLSILDFSIT SASAQQATDR SNSVNYSTDV
SEQ ID NO:  3   .......MKS RYKRLTSLAL SLSMALGISL PAWASPDTSV DNKVNFSTDV
SEQ ID NO:  4   .......MKK QVKWLTSVSM SVGIALGAAL PVWASPDTSV NNKLNFSTDT
SEQ ID NO:  5   .......... .......... .......... ....ASDTAV SNVVNYSTDV
SEQ ID NO:  6   .......... .......... .......... ....APDTSV SNVVNYSTDV
SEQ ID NO:  7   MFQMAKRAFL STTLTLGLLA GSALPFLPAS AVYADPDTAV TNKQSFSTDV
SEQ ID NO:  8   MFQMAKRVLL STTLTFSLLA GSALPFLPAS AIYADADTAV TNKQNFSTDV
SEQ ID NO:  9   .....MKRFM KLTAVWTLWL SLTLGLL..S PVHAAPDTSV SNKQNFSTDV
SEQ ID NO: 10   .....MKRFM KLTAVWTLWL SLTLGLL..S PVHAAPDTSV SNKQNFSTDV
SEQ ID NO: 11   .....MKKFL KSTAALALGL SLTFGLF..S PAQAAPDTSV SNKQNFSTDV
SEQ ID NO: 12   .......... .......... .......... ....APDTSV SNKQNFSTDV
SEQ ID NO: 13   .....MKNLT VLLKTIPLAL LLFI.LLS.. .LPTAAQADV TNKVNYTRDV
SEQ ID NO: 14   .....MNDLN DFLKTILLSF IFFL.LLS.. .LPTVAEADV TNKVNYSKDV
SEQ ID NO: 15   .....MRRWL SLVLSMSFVF SAIF.IVSDT QKVTVEAAGN LNKVNFTSDV
SEQ ID NO: 16   ...MKRNRFF NTSAAIAISI ALNTFFCSMQ TIAAEPEETY ...LDFRKET 51                                                                 100
SEQ ID NO:  1   IYQIVTDRFY DGDESNNPSG ELYSEGCKNL RKYCGGDWQG IIDKIDDGYL
SEQ ID NO:  2   IYQIVTDRFY DGDESNNPSG ELYSEDCKNL RKYCGGDWQG IIDKIDDGYL
SEQ ID NO:  3   IYQIVTDRFA DGDRTNNPAG DAFSGDRSNL KLYFGGDWQG IIDKINDGYL
SEQ ID NO:  4   VYQIVTDRFV DGNSANNPTG AAFSSDHSNL KLYFGGDWQG ITNKINDGYL
SEQ ID NO:  5   IYQIVTDRFV DGNTSNNPTG DLYDPTHTSL KKYFGGDWQG IINKINDGYL
SEQ ID NO:  6   IYQIVTDRFL DGNPSNNPTG DLYDPTHTSL KKYFGGDWQG IINKINDGYL
SEQ ID NO:  7   IYQVFTDRFL DGNPSNNPTG AAYDATCSNL KLYCGGDWQG LINKINDNYF
SEQ ID NO:  8   IYQVFTDRFL DGNPSNNPTG AAFDGTCSNL KLYCGGDWQG LVNKINDNYF
SEQ ID NO:  9   IYQIFTDRFS DGNPANNPTG AAFDGSCTNL RLYCGGDWQG IINKINDGYL
SEQ ID NO: 10   IYQIFTDRFS DGNPANNPTG AAFDGSCTNL RLYCGGDWQG IINKINDGYL
SEQ ID NO: 11   IYQIFTDRFS DGNPANNPTG AAFDGTCTNL RLYCGGDWQG IINKINDGYL
SEQ ID NO: 12   IYQIFTDRFS DGNPANNPTG PAFDGTCTNL RLYCGGDWQG IINKINDGYL
SEQ ID NO: 13   IYQIVTDRFS DGDPSNNPTG AIYSQDCSDL HKYCGGDWQG IIDKINDGYL
SEQ ID NO: 14   IYQIVTDRFS DGNPGNNPSG AIFSQNCIDL HKYCGGDWQG IIDKINDGYL
SEQ ID NO: 15   VYQIVVDRFV DGNTSNNPSG ALFSSGCTNL RKYCGGDWQG IINKINDGYL
SEQ ID NO: 16   IYFLFLDRFS DGDPSNNAGF NSATYDPNNL KKYTGGDLRG LINKL..PYL 101                                                                150
SEQ ID NO:  1   TNMGVTALWI SPPVENIFET IDDES..GTT SYHGYWARDY KKTNPFFGST
SEQ ID NO:  2   TNMGVTALWI SPPVENIFET IDDEF..GTT SYHGYWARDY KKTNPFFGST
SEQ ID NO:  3   TGMCVTALWI SQPVENITSV IKYSGVNN.T SYHGYWARDF KQTNDAFGDF
SEQ ID NO:  4   TGMGITALWI SQPVENITAV INYSGVNN.T AYHGYWPRDF KKTNAAFGSF
SEQ ID NO:  5   TGMGVTAIWI SQPVENIYAV LPDSTFGGST SYHGYWARDF KRTNPYFGSF
SEQ ID NO:  6   TGMGITAIWI SQPVENIYAV LPDSTFGGST SYHGYWARDF KKTNPFFGSF
SEQ ID NO:  7   SDLGVTALWI SQPVENIFAT INYSGVTN.T AYHGYWARDF KKTNPYFGTM
SEQ ID NO:  8   SDLGVTALWI SQPVENIFAT INYSGVTN.T AYHGYWARDF KKTNPYFGTM
SEQ ID NO:  9   TGMGITAIWI SQPVENIYSV INYSGVNN.T AYHGYWARDF KKTNPAYGTM
SEQ ID NO: 10   TGMGITAIWI SQPVENIYSV INYSGVHN.T AYHGYWARDF KKTNPAYGTM
SEQ ID NO: 11   TGMGVTAIWI SQPVENIYSI INYSGVNN.T AYHGYWARDF KKTNPAYGTI
SEQ ID NO: 12   TGMGITAIWI SQPVENIYSV INYSGVNN.T AYHGYWARDF KKTNPAYGTI
SEQ ID NO: 13   TDLGITAIWI SQPVENVYAL ..HPS..GYT SYHGYWARDY KRTNPFYGDF
SEQ ID NO: 14   TDLGITALWI SQPVENVYAL ..HPS..GYT SYHGYWARDY KKTNPYYGNF
SEQ ID NO: 15   TDMGVTAIWI SQPVENVFSV MNDAS..GSA SYHGYWARDF KKPNPFFGTL
SEQ ID NO: 16   KSLGVTSIWI TPPIDNV... .NNTDAAGNT GYHGYWGRDY FRIDEHFGNL
```

Fig. 1

```
              151                                                        200
SEQ ID NO: 1   EDFERLIETA HSH..DIKIV IDLAPNHTSP ADFDNPNYAE NGILYDNGNY
SEQ ID NO: 2   EDFERLIETA HSH..DIKIV IDLAPNHTSP ADFDNPDYAE NGVLYDDGNY
SEQ ID NO: 3   ADFQNLIDTA HAH..NIKVV IDFAPNHTSP ADRDNPGFAE NGGMYDNGSL
SEQ ID NO: 4   TDFSNLIAAA HSH..NIKVV MDFAPNHTNP ASSTDPSFAE NGALYNNGTL
SEQ ID NO: 5   TDFQNLINTA HAH..NIKVI IDFAPNHTSP ASETDPTYAE NGRLYDNGTL
SEQ ID NO: 6   TDFQNLIATA HAH..NIKVI IDFAPNHTSP ASETDPTYGE NGRLYDNGVL
SEQ ID NO: 7   ADFQNLITTA HAK..GIKIV IDFAPNHTSP AMETDTSFAE NGRLYDNGTL
SEQ ID NO: 8   TDFQNLVTTA HAK..GIKII IDFAPNHTSP AMETDTSFAE NCKLYDNGNL
SEQ ID NO: 9   QDFKNLIDTA HAH..NIKVI IDFAPNHTSP ASSDDPSFAE NGRLYDNGNL
SEQ ID NO: 10  QDFKNLIDTA HAH..NIKVI IDFAPNHTSP ASSDDPSFAE NGRLYDNGNL
SEQ ID NO: 11  ADFQNLIAAA HAK..NIKVI IDFAPNHTSP ASSDQPSFAE NGRLYDNGTL
SEQ ID NO: 12  ADFQNLIAAA HAK..NIKVI IDFAPNHTSP ASLDQPSFAE NGKLYNNGRD
SEQ ID NO: 13  SDFDRLMDTA HSN..GIKVI MDFTPNHSSP ALETDPSYAE NGAVYNDGVL
SEQ ID NO: 14  DDFDRLMSTA HSN..GIKVI MDFTPNHSSP ALETNPNYVE NGAIYDNGAL
SEQ ID NO: 15  SDFQRLVDAA HAK..GIKVI IDFAPNHTSP ASETNPSYME NGRLYDNGTL
SEQ ID NO: 16  DDFKELTSLM HSPDYNMKLV LDYAPNHSNA NDEN.....E FGALYRDGVF 201                                                        250
SEQ ID NO: 1   VSSYSDNS.. ..DLFLYNGG .TDFSTYEDE IYRNLFDLAS FNHINAELNN
SEQ ID NO: 2   LGSYSDDS.. ..DLFLYNGG .TDFSNYEDE IYRNLFDLAS FNHINSELNN
SEQ ID NO: 3   LGAYSNDTA. ..GLFHHNGG .TDFSTIEDG IYKNLYDLAD INHNNNAMDA
SEQ ID NO: 4   LGKYSNDTA. ..GLFHHNGG .TDFSTTESG IYKNLYDLAD INQNNNTIDS
SEQ ID NO: 5   LGGYTNDTN. ..GYFHHYGG .TDFSSYEDG IYRNLFDLAD LNQQNSTIDS
SEQ ID NO: 6   LGGYTNDTN. ..GYFHHYGG .TNFSSYEDG IYRNLFDLAD LDQQNSTIDS
SEQ ID NO: 7   VGGYTNDTN. ..GYFHHNGG .SDFSSLENG IYKNLYDLAD FNHNNATIDK
SEQ ID NO: 8   VGGYTNDTN. ..GYFHHNGG .SDFSTLENG IYKNLYDLAD LNHNNSTIDT
SEQ ID NO: 9   LGGYTNDTQ. ..NLFHHYGG .TDFSTIENG IYKNLYDLAD LNHNNSSVDV
SEQ ID NO: 10  LGGYTNDTQ. ..NLFHHYGG .TDFSTIENG IYKNLYDLAD LNHNNSSVDV
SEQ ID NO: 11  LGGYTNDTQ. ..NLFHHNGG .TDFSTTENG IYKNLYDLAD LNHNNSTVDV
SEQ ID NO: 12  EGGYTNDTH. ..NLFHHNGG .TDFSTTENG IYKNLYDLAD LNHNNSTVDT
SEQ ID NO: 13  IGNYSNDPN. ..NLFHHNGG .TDFSSYEDS IYRNLYDLAD YDLNNTVMDQ
SEQ ID NO: 14  LGNYSNDQQ. ..NLFHHNGG .TDFSSYEDS IYRNLYDLAD YDLNNTVMDQ
SEQ ID NO: 15  LGGYTNDAN. ..MYFHHNGG .TTFSSLEDG IYRNLFDLAD LNHQNPVIDR
SEQ ID NO: 16  ITDYPTNVAA NTGWYHHNGG VTNWNDFFQV KNHNLFNLSD LNQSNTDVYQ 251                                                        300
SEQ ID NO: 1   YLEDAVKKWL DLGIDGIRID AVAHMPPGWQ KAYMDTIY.D HRAV.....F
SEQ ID NO: 2   YLEDAVKKWL DLGIDGIRID AVAHMPPGWK KAYMDTIY.D HRAV.....F
SEQ ID NO: 3   YFKSAIDLWL GMGVDGIRFD AVKHMPFGWQ KSFVSSIYGG DHPV.....F
SEQ ID NO: 4   YLKESIQLWL NLGVDGIRFD AVKHMPQGWQ KSYVSSIYSS ANPV.....F
SEQ ID NO: 5   YLKSAIKVWL DMGIDGIRLD AVKHMPFGWQ KNFMDSIL.S YRPV.....F
SEQ ID NO: 6   YLKAAIKLWL DMGIDGIRMD AVKHMAFGWQ KNFMDSIL.S YRPV.....F
SEQ ID NO: 7   YFKDAIKLWL DMGVDGIRVD AVKHMPLGWQ KSWMSSIY.A HKPV.....F
SEQ ID NO: 8   YFKDAIKLWL DMGVDGIRVD AVKHMPQGWQ KNWMSSIY.A HKPV.....F
SEQ ID NO: 9   YLKDAIKMWL DLGVDGIRVD AVKHMPFGWQ KSFMATIN.N YKPV.....F
SEQ ID NO: 10  YLKDAIKMWL DLGVDGIRVD AVKHMPFGWQ KSFMSTIN.N YKPV.....F
SEQ ID NO: 11  YLKDAIKMWL DLGIDGIRMD AVKHMPFGWQ KSFMAAVN.N YKPV.....F
SEQ ID NO: 12  YLKDAIKMWL DLGIDGIRMD AVKHMPFGWQ KSFMATVN.N YKPV.....F
SEQ ID NO: 13  YLKESIKLWL DKGIDGIRVD AVKHMSEGWQ TSLMSDIY.A HEPV.....F
SEQ ID NO: 14  YLKESIKFWL DKGIDGIRVD AVKHMSEGWQ TSLMSEIY.S HKPV.....F
SEQ ID NO: 15  YLKDAVKMWI DMGIDGIRMD AVKHMPFGWQ KSLMDEID.N YRPV.....F
SEQ ID NO: 16  YLLDGSKFWI DAGVDAIRID AIKHMDKSFI QKWTSDIYDY SKSIGREGFF
```

Fig. 1 continued

```
              301                                                      350
SEQ ID NO:  1   TFGEWFTGPY ....G.NEDY TKFANNSGMS VLDFRFAQTT RNVIGNNNGT
SEQ ID NO:  2   TFGEWFTGPS ....G.NEDY TKFANNSGMS VLDFRFAQTT RNVIGNNNGT
SEQ ID NO:  3   TFGEWYLGAD ....QTDGDN IKFANESGMN LLDFEYAQEV REVFRDKTET
SEQ ID NO:  4   TFGEWFLGPD ....EMTQDN INFANQSGMH LLDFAFAQEI REVFRDKSET
SEQ ID NO:  5   TFGEWFLGTN ....EIDVNN TYFANESGMS LLDFRFSQKV RQVFRDNTDT
SEQ ID NO:  6   TFGEWYLGTN ....EVDPNN TYFANESGMS LLDFRFAQKV RQVFRDNTDT
SEQ ID NO:  7   TFGEWFLGSA ....ASDADN TDFANKSGMS LLDFRFNSAV RNVFRDNTSN
SEQ ID NO:  8   TFGEWFLGSA ....APDADN TDFANESGMS LLDFRFNSAV RNVFRDNTSN
SEQ ID NO:  9   TFGEWFLGVN ....EISPEY HQFANESGMS LLDFRFAQKA RQVFRDNTDN
SEQ ID NO: 10   NFGEWFLGVN ....EISPEY HQFANESGMS LLDFPFAQKA RQVFRDNTDN
SEQ ID NO: 11   TFGEWFLGVN ....EVSPEN HKFANESGMS LLDFRFAQKV RQVFRDNTDN
SEQ ID NO: 12   TFGEWFLGVN ....EVSAEN HKFANVSGMS LLDFRFAQKV RQVFKDNTDN
SEQ ID NO: 13   TFGEWFLGSG ....EVDPQN HHFANESGMS LLDFQFGQTI RDVLMDGSSN
SEQ ID NO: 14   TFGEWFLGSG ....EVDPQN HHFANESGMS LLDFQFGQTI RNVLKDRTSN
SEQ ID NO: 15   TFGEWFLSEN ....EVDANN HYFANESGMS LLDFRFGQKL RQVLRNNSDN
SEQ ID NO: 16   FFGEWFGASA NTTTGVDGNA IDYANTSGSA LLDFGFRDTL ERVLVGRSGN 351                                                      400
SEQ ID NO:  1   .MYDIEKMLT DTENDYDRPQ DQVTFLDNHD MSRFTNDGES T.........
SEQ ID NO:  2   .MYDIEKMLT DTENDYDRPQ DQVTFLDNHD MSRFTNGGES T.........
SEQ ID NO:  3   .MKDLYEVLA STESQYDYIN NMVTFIDNHD MDRFQVAGSG T.........
SEQ ID NO:  4   .MTDLNSVIS STGSSYNYIN NMVTFIDNHD MDRFQQAGAS T.........
SEQ ID NO:  5   .MYGLDSMIQ STASDYNFIN DMVTFIDNHD MDRFYNG.GS T.........
SEQ ID NO:  6   .MYGLDSMIQ STAADYNFIN DMVTFIDNHD MDRFYTG.GS T.........
SEQ ID NO:  7   .MYALDSMIN STATDYNQVN DQVTFIDNHD MDRFKTSAVN N.........
SEQ ID NO:  8   .MYALDSMLT ATAADYNQVN DQVTFIDNHD MDRFKTSAVN N.........
SEQ ID NO:  9   .MYGLKAMLE GSEVDYAQVN DQVTFIDNHD MERFHTSNGD R.........
SEQ ID NO: 10   .MYGLKAMLE GSEVDYAQVN DQVTFIDNHD MERFHTSNGD R.........
SEQ ID NO: 11   .MYGLKAMLE GSAADYAQVD DQVTFIDNHD MERFHASNAN R.........
SEQ ID NO: 12   .MYGLKSMLE GSATDYAQME DQVTFIDNHD MERFHNNSAN R.........
SEQ ID NO: 13   .WYDFNEMIA STEEDYDEVI DQVTFIDNHD MSRFSFEQSS N.........
SEQ ID NO: 14   .WYDFNEMIT STEKEYNEVI DQVTFIDNHD MSRFSVGSSS N.........
SEQ ID NO: 15   .WYGFNQMIQ DTASAYDEVL DQVTFIDNHD MDRFMIDGGD P.........
SEQ ID NO: 16   TMKTLNSYLI KRQTVFTSDD WQVVFMDNHD MARIGTALRS NATTFGPGNN 401                                                      450
SEQ ID NO:  1   .......... ..RTTDIGLA LMLTSRGVPT IYYGTEQYME G.........
SEQ ID NO:  2   .......... ..RTTDIGLA LMLTSRGVPT IYYGTEQYMK G.........
SEQ ID NO:  3   .......... ..RATEQALA LTLTSRGVPA IYYGTEQYMT G.........
SEQ ID NO:  4   .......... ..RPTEQALA VTLTSRGVPA IYYGTEQYMT G.........
SEQ ID NO:  5   .......... ..RPVEQALA FTLTSRGVPA IYYGTEQYMT G.........
SEQ ID NO:  6   .......... ..RPVEQALA FTLTSRGVPA IYYGTEQYMT G.........
SEQ ID NO:  7   .......... ..RRLEQALA FTLTSRGVPA IYYGTEQYLT G.........
SEQ ID NO:  8   .......... ..RRLEQALA FTLTSRGVPA IYYGTEQYLT G.........
SEQ ID NO:  9   .......... ..RKLEQALA FTLTSRGVPA IYYGSEQYMS G.........
SEQ ID NO: 10   .......... ..RKLEQALA FTLTSRGVPA IYYGSEQYMS G.........
SEQ ID NO: 11   .......... ..RKLEQALA FTLTSRGVPA IYYGTEQYMS G.........
SEQ ID NO: 12   .......... ..RKLEQALA FTLTSRGVPA IYYGTEQYMS G.........
SEQ ID NO: 13   .......... ..RHTDIALA VLLTSRGVPT IYYGTEQYLT G.........
SEQ ID NO: 14   .......... ..RQTDMALA VLLTSRGVPT IYYGTEQYVT G.........
SEQ ID NO: 15   .......... ..RKVDMALA VLLTSRGVPN IYYGTEQYMT G.........
SEQ ID NO: 16   ETGGSQSEAF AQKRIDLGLV ATMTVRGIPA IYYGTEHYAA NFTSNSFGQV
```

Fig. 1 continued

```
                451                                                            500
SEQ ID NO: 1    DGDPGSRGMM ESFGENTDAY KLIQKLAPLR KSNPAYGYGT TKERWINDDV
SEQ ID NO: 2    DGDPGSRGMM ASFDENTDAY KLIQKLAPLR KSNPAYGYGT TTERWINDDV
SEQ ID NO: 3    DGDPNNRAMM TSFNTGTTAY KVIQALAPLR KSNPAIAYGT TTERWVNNDV
SEQ ID NO: 4    NGDPNNRGMM TGFDTNKTAY KVIKALAPLR KSNPALAYGS TTQRWVNSDV
SEQ ID NO: 5    NGDPYNRAMM TSFNTSTTAY NVIKKLAPLR KSNPAIAYGT TQQRWINNDV
SEQ ID NO: 6    NGDPYNRAMM TSFDTTTTAY NVIKKLAPLR KSNPAIAYGT QKQRWINNDV
SEQ ID NO: 7    NGDPDNRAKM PSFSKSTTAF NVISKLAPLR KSNPAIAYGS TQQRWINNDV
SEQ ID NO: 8    NGDPDNRGKM PSFSKSTTAF NVISKLAPLR KSNPAIAYGS TQQRWINNDV
SEQ ID NO: 9    GNDPDNRARL PSFSTTTTAY QVIQKLAPLR KSNPAIAYGS THERWINNDV
SEQ ID NO: 10   GNDPDNRARI PSFSTTTTAY QVIQKLAPLR KSNPAIAYGS TQERWINNDV
SEQ ID NO: 11   GTDPDNRARI PSFSTSTTAY QVIQKLAPLR KCNPAIAYGS TQERWINNDV
SEQ ID NO: 12   GNDPDNRARI PSFSTTTTAY QVSKKLAPLR KSNPAIAYGT TQERWINNDV
SEQ ID NO: 13   GNDPENRKPM SDFDRTTNSY QIISTLASLR QNNPALGYGN TSERWINSDV
SEQ ID NO: 14   GNDPENRKPL KTFDRSTNSY QIISKLASLR QTNSALGYGT TTERWLNEDI
SEQ ID NO: 15   NGDPNNRKMM SSFNKNTRAY QVIQKLSSLR RNNPALAYGD TEQRWINGDV
SEQ ID NO: 16   GSDPYNREKM PGFDTESEAF SIIKTLGDLR KSSPAIQNGT YTELWVNDDI 501                                                            550
SEQ ID NO: 1    IIYERNFGDN YALIAINRNL NTSYNIQGLQ TEMPSNSYDD VLDGLLDGQS
SEQ ID NO: 2    LIYERHFGEN YALIAINRSL NTSYNIQGLQ TEMPSNSYDD VLDGLLDGQS
SEQ ID NO: 3    LIIERKFGSS AALVAINRNS SAAYPISGLL SSLPAGTYSD VLNGLLNGNS
SEQ ID NO: 4    YVYERKFGSN VALVAVNRSS TTAYPISGAL TALPNGTYTD VLGGLLNGNS
SEQ ID NO: 5    YIYERKFGNN VALVAINRNL STSYNITGLY TALPAGTYTD VLGGLLNGNS
SEQ ID NO: 6    YIYERQFGNN VALVAINRNL STSYYITGLY TALPAGTYSD MLGGLLNGSS
SEQ ID NO: 7    YVYERKFGKS VAVVAVNRNL STSASITGLS TSLPTGSYTD VLGGVLNGNN
SEQ ID NO: 8    YIYERKFGKS VAVVAVNRNL TTPTSITNLN TSLPSGTYTD VLGGVLNGNN
SEQ ID NO: 9    IIYERKFGNN VAVVAINRNM NTPASITGLV TSLRRASYND VLGGILNGNT
SEQ ID NO: 10   IIYERKFGNN VAVVAINRNM NTPASITGLV TSLPQGSYND VLGGILNGNT
SEQ ID NO: 11   LIYERKFGSN VAVVAVNRNL NAPASISGLV TSLPQGSYND VLGGLLNGNT
SEQ ID NO: 12   LIYERKFGNN VAVIAVNRNV NTSASITGLV TSLPAGSYTD VLGGLLNGNN
SEQ ID NO: 13   YIYERSFGDS VVLTAVN.SG DTSYTINNLN TSLPQCQYTD ELQQLLDGNE
SEQ ID NO: 14   YIYERTFGNS IVLTAVN.SS NSNQTITNLN TSLPQGNYTD ELQQRLDGNT
SEQ ID NO: 15   YVYERQFGKD VVLVAVNRSS SSNYSITGLF TALPAGTYTD QLGGLLDGNT
SEQ ID NO: 16   LVFERRSGND IVIVALNRGE ANTINVKNIA VP......NG VYPSLIGNNS 551                                                            600
SEQ ID NO: 1    IVVDNNGEVN EFQMSPGEVG VWEFEATNVD KPSIGQVGPI IGEAGRTVTI
SEQ ID NO: 2    IVVDNKGGVN EFQMSPGEVS VWEFEAENVD KPSIGQVGPI IGEAGRTVTI
SEQ ID NO: 3    ITVGSGGAVT NFTLAAGGTA VWQYTAPE.T SPAIGNVGPT MGQPGNIVTI
SEQ ID NO: 4    ITVN.GGTVS NFTLAAGGTA VWQYTTTE.S SPIIGNVGPT MGKPGNTITI
SEQ ID NO: 5    ISVASDGSVT PFTLSAGEVA VWQYVSSS.N SPLIGHVGPT MTKAGQTITI
SEQ ID NO: 6    ITVSSNGSVT PFTLAPGEVA VWQYVSTT.N PPLIGHVGPT MTKAGQTITI
SEQ ID NO: 7    IT.STNGSIN NFTLAAGATA VWQYTTAE.T TPTIGHVGPV MGKPGNVVTI
SEQ ID NO: 8    IT.SSGGNIS SFTLAAGATA VWQYTASE.T TPTIGHVGPV MGKPGNVVTI
SEQ ID NO: 9    LTVGAGGAAS NFTLAPGGTA VWQYTTDA.T TPIIGNVGPM MAKPGVTITI
SEQ ID NO: 10   LTVGAGGAAS NFTLAPGGTA VWQYTTDA.T APINGNVGPM MAKAGVTITI
SEQ ID NO: 11   LSVGSGGAAS NFTLAAGGTA VWQYTAAT.A TPTIGHVGPM MAKPGVTITI
SEQ ID NO: 12   LTVGSGGSAS IFTLAAGGTA VWQYTTAV.T APTIGHVGPM MAKPGAAVTI
SEQ ID NO: 13   ITVNSNGAVD SFQLSANGVS VWQITEEH.A SPLIGHVGPM MGKHGNTVTI
SEQ ID NO: 14   ITVNANGAVN SFQLRANSVA VWQVSNPS.T SPLIGQVGPM MGKAGNTITV
SEQ ID NO: 15   IQVGSNGSVN AFDLGPGEVG VWAYSATE.S TPIIGHVGPM MGQVGHQVTI
SEQ ID NO: 16   VSVANK..RT TLTLMQNEAV VIRSQSDDAE NPTVQ..... ..........
```

Fig. 1 continued

```
                601                                                              650
SEQ ID NO: 1    SGEGFGSSPG TVQFGSTS.. .AEIVSWNDT VIIITVPNNE AGYHDITVVT
SEQ ID NO: 2    SGEGFGSSQG TVHFGSTS.. .AEILSWNDT IITLTVPNNE AGYHDITVVT
SEQ ID NO: 3    DGRGFGGTAG TVYFGTTAVT GSGIVSWEDT QIKAVIPKVA AGKTGVSVKT
SEQ ID NO: 4    DGRGFGTTKN KVTFGTTAVT GANIVSWEDT EIKVKVPNVA AGNTAVTVTN
SEQ ID NO: 5    DGRGFGTTSG QVLFGSTAGT ...IVSWDDT EVKVKVPSVT PGKYNISLKT
SEQ ID NO: 6    DGRGFGTTAG QVLFGTTPAT ...IVSWEDT EVKVKVPALT PGKYNITLKT
SEQ ID NO: 7    DGRGFGSTKG TVYFGTTAVT GAAITSWEDT QIKVTIPSVA AGNYAVKVA.
SEQ ID NO: 8    DGRGFGSAKG TVYFGTTAVT GSAITSWEDT QIKVTIPPVA GGDYAVKVA.
SEQ ID NO: 9    DGRGFGSGKG TVYFGTTAVT GADIVAWEDT QIQVKIPAVP GGIYDIRVAN
SEQ ID NO: 10   DGRA.SARQG TVYFGTTAVT GADIVAWEDT QIQVKILRVP GGIYDIRVAN
SEQ ID NO: 11   DGRGFGSSKG TVYFGTTAVS GADITSWEDT QIKVKIPAVA GGNYNIKVAN
SEQ ID NO: 12   DGRGFGATKG TVYFGTTAVT GANITAWEDT QIKVKIPAVA GGVYNIKIAN
SEQ ID NO: 13   TGEGFGDNEG SVLFDSDF.. .SDVLSWSDT KIEVSVPDVT AGHYDISVVN
SEQ ID NO: 14   SGEGFGDERG SVLFDSTS.. .SEIISWSNT KISVKVPNVA GGYYDLSVVT
SEQ ID NO: 15   DGEGFGTNTG TVKFGTTA.. .ANVVSWSNN QIVVAVPNVS PGKYNITVQS
SEQ ID NO: 16   .......... .......... .......... .......... ..........

651                                                              700
SEQ ID NO: 1    EDEQVSNAYE .FEVLTADQV TVRFIIDNAE TKMGENIFLV GNVHELGNW.
SEQ ID NO: 2    EDEQVSNAYE .FEVLTADQV TVRFIIDNAE TKLGENVFLV GNVHELGNW.
SEQ ID NO: 3    SSCTASNTFK SFNVLTGDQV TVRFLVNQAN TNYGTNVYLV GNAAELGSW.
SEQ ID NO: 4    AAGTTSAAFN NFNVLTADQV TVRFKVNNAT TALGQNVYLT GNVAELGNW.
SEQ ID NO: 5    SSGATSNTYN NINILTGNQI CVRFVVNNAS TVYGENVYLT GNVAELGNW.
SEQ ID NO: 6    ASGVTSNSYN NINVLTGNQV CVRFVVNNAT TVWGENVYLT GNVAELGNW.
SEQ ID NO: 7    ASGVNSNAYN NFTILTGDQV TVRFVVNNAS TTLGQNLYLT GNVAELGNWS
SEQ ID NO: 8    ANGVNSNAYN DFTILSGDQV SVRFVINNAT TALGENIYLT GNVSELGNWT
SEQ ID NO: 9    AAGAASNIYD NFEVLTGDQV TVRFVINNAT TALGQNVFLT GNVSELGNW.
SEQ ID NO: 10   AAGAASNIYD NFEVLTGDQV TVRFVINNAT TALGQNVFLT GNVSELGNW.
SEQ ID NO: 11   AAGTASNVYD NFEVLSGDQV SVRFVNNAT  TALGQNVYLT GSVSELGNW.
SEQ ID NO: 12   SAGTSSNVHD NFEVLSGDQV SVRFVNNAT  TALGQNVYLA GSVSELGNW.
SEQ ID NO: 13   AGDSQSPTYD KFEVLTGDQV SIRFAVNNAT TSLGTNLYMV GNVNELGNW.
SEQ ID NO: 14   AANIKSPTYK EFEVLSGNQV SVRFGVNNAT TSPGTNLYIV GNVNELGNW.
SEQ ID NO: 15   SSGQTSAAYD NFEVLTNDQV SVRFVVNNAT TNLGQNIYIV GNVYELGNW.
SEQ ID NO: 16   .......... .......... SINFTCNNGY TISGQSVYII GNIPQLGGW.

701                                                              750
SEQ ID NO: 1    DPEQSVGRFF NQVVYQYPTW YYDVNVPANT DLEFKFIKID Q...DNNVTW
SEQ ID NO: 2    DPEQSVGRFF NQIVYQYPTW YYDVNVPANT DLEFKFIKID Q...DNNVIW
SEQ ID NO: 3    DPNKAIGPMY NQVIAKYPSW YYDVSVPAGT KLDFKFIKKG G...GT.VTW
SEQ ID NO: 4    TAANAIGPMY NQVEASYPTW YFDVSVPANT ALQFKFIKVN G...ST.VTW
SEQ ID NO: 5    DTSKAIGPMF NQVVYQYPTW YYDVSVPAGT TIQFKFIKKN G...NT.ITW
SEQ ID NO: 6    DTSKAIGPMF NQVVYQYPTW YYDVSVPAGT TIEFKFIKKN G...ST.VTW
SEQ ID NO: 7    TGSTAIGPAF NQVIHQYPTW YYDVSVPAGK QLEFKFFKKN G...ST.ITW
SEQ ID NO: 8    TGAASIGPAF NQVIHAYPTW YYDVSVPAGK QLEFKFFKKN G...AT.ITW
SEQ ID NO: 9    DPNNAIGPMY NQVVYQYPTW YYDVSVPAGQ TIEFKFLKKQ G...ST.VTW
SEQ ID NO: 10   DPNNAIGPMY NQVVYQYPTW YYDVSVPAGQ TIEFKFLKKQ G...ST.VTW
SEQ ID NO: 11   DPAKAIGPMY NQVVYQYPNW YYDVSVPAGK TIEFKFLKKQ G...ST.VTW
SEQ ID NO: 12   DPAKAIGPLY NQVIYQYPTW YYDVTVPAGK TIEFKFLKKQ G...ST.VTW
SEQ ID NO: 13   DPDQAIGPMF NQVMYQYPTW YYDISVPAEE NLEYKFIKKD S...SGNVVW
SEQ ID NO: 14   DADKAIGPMF NQVMYQYPTW YYDISVPAGK NLEYKYIKKD Q...NGNVVW
SEQ ID NO: 15   DTSKAIGPMF NQVVYSYPTW YIDVSVPEGK TIEFKFIKKD S...QGNVTW
SEQ ID NO: 16   ....DLTKAV KISPTQYPQW SASLELPSDL NVEWKCVKRN ETNPTANVEW
```

Fig. 1 continued

```
                    751                    774
SEQ ID NO:  1   QSGANHTYSS  PESGTGIIRV  DW..
SEQ ID NO:  2   QSGANQTYSS  PESGTGIIRV  DW..
SEQ ID NO:  3   EGGGNHTYTT  PASGVGTVTV  DWQN
SEQ ID NO:  4   EGGNNHTFTS  PSSGVATVTV  DWQN
SEQ ID NO:  5   EGGSNHTYTV  PSSSTGTVIV  NWQQ
SEQ ID NO:  6   EGGYNHVYTT  PTSGTATVIV  DWQP
SEQ ID NO:  7   ESGSNHTFTT  PASGTATVTV  NWQ.

SEQ ID NO:  8   EGGSNHTFTT  PTSGTATVTI  NWQ.
SEQ ID NO:  9   EGGANRTFTT  PTSGTATVNV  NWQP
SEQ ID NO: 10   EGGANRTFTT  PTSGTATVNV  NWQP
SEQ ID NO: 11   EGGSNHTFTA  PSSGTATINV  NWQP
SEQ ID NO: 12   EGGSNHTFTA  PTSGTATINV  NWQP
SEQ ID NO: 13   ESGNNHTYTT  PATGTDTVLV  DWQ.
SEQ ID NO: 14   QSGNNRTYTS  PTTGTDTVMI  NW..
SEQ ID NO: 15   ESGSNHVYTT  PTNTTGKIIV  DWQN
SEQ ID NO: 16   QSGANNQFNS  NDTQTTNGSF  ....
```

Fig. 1 continued

```
         1         10        20        30        40        50        60        70
                    *
------SSSASVKGDVIYQIIIDRFYDGDTTNNNPAKSYGLYDPTKSKWKMYWGGDLEGVRQKL--PYLK  62
ASDTAVSNVVNYSTDVIYQIVTDRFVDGNTSNNPT---GDLYDPTHTSLKKYFGGDWQGIINKINDGYLT  67
  *

*
QLGVTTIWLSPVLDNLDTLAGT----DNTGYHGYWTRDFKQIEEHFGNWTTFDTLVNDAHQNGIKVIVDF 128
GMGVTAIWISQPVENIYAVLPDSTFGGSTSYHGYWARDFKRTNPYFGSFTDFQNLINTAHAHNIKVIIDF 137
                                          *

VPNHSTPFKANDSTFAEGGALYNNGTYMGNYFDDATKGYFHHNGDISNWDDRYEAQWKNFTDPAGFSLAD 198
APNHTSPASETDPTYAENGRLYDNGTLLGGYTNDT-NGYFHHYGGT-DFSSYEDGIYRNLF-----DLAD 200
                                                              *
LSQENGTIAQYLTDAAVQLVAHGADGLRIDAVKHFNSGFSKSLADKLYQKKDIFLVGEWYGDD-PGTANH 267
LNQQNSTIDSYLKSAIKVWLDMGIDGIRLDAVKHMPFGWQKNFMDSILSYRPVFTFGEWFLG-TNEI--D 267
       *       *                                          *         *

*              *                      *
LEKVRYANNSGVNVLDFDLNTVIRNVFGTFTQTMYDLNNMVNQTGNEYKYKENLITFIDNHDMSRFLSVN 337
VNNTYFANESGMSLLDFRFSQKVRQVFRDNTDTMYGLDSMIQSTASDYNFINDMVTFIDNHDMDRFYN-G 336
                                    *

*
SNKANLHQALAFILTSRGTPSIYYGTEQYMAGGNDPYNRGMMPAFDTTTTAFKEVSTLAGLRRNNAAIQY 407
GSTRPVEQALAFTLTSRGVPAIYYGTEQYMTGNGDPYNRAMMTSFNTSTTAYNVIKKLAPLRKSNPAIAY 406

*
GTTTQRWINNDVYIYERKFFNDVVLVAINRNTQSSYSISGLQTALPNGSYADYLSGLLGGNGISVS-NGS 476
GTTQQRWINNDVYIYERKFGNNVALVAINRNLSTSYNITGLYTALPAGTYTDVLGGLLNGNSISVASDGS 476
                                                                 *
VASFTLAPGAVSVWQYST-SASAPQIGSVAPNMGIPGNVVTIDGKGFGTTQGTVTFGGVTATVKSWTSNR 545
VTPFTLSAGEVAVWQYVSSSN-SPLIGHVGPTMTKAGQTITIDGRGFGTTSGQVLFGSTAGTIVSWDDTE 545
                 *      *

*              *
IEVYVPNMAAGLTDVKVTA-GGVSSNLYS-YNILSGTQTSVVFTVKSAPPTNLGDKIYLTGNIPELGNWS 613
VKVKVPSVTPGKYNISLKTSSGATSNTYNNINILTGNQICVRFVVNNASTVY-GENVYLTGNVAELGNWD 614
               *

*
TDTSGAVNNAQGPLLAP---NYPDWFYVFSVPAGKTIQFKFFIKRADGT-IQWENGSNHVATTPTGATGN 679
TS------KAIGPMFNQVVYQYPTWYYDVSVPAGTTIQFKFIKN--GNTITWEGGSNHTYTVPSSSTGT 676
                 *                        *

ITVTWQN 686
VIVNWQQ 683
```

Fig. 2

Hypothetical sequences with "structural stop codons"

Hypothetical sequences with "structural stop codons"

HYBRID POLYPEPTIDE OF A MALTOGENIC ALPHA-AMYLASE AND A CYCLODEXTRIN GLUCANOTRANSFERASE

CROSS-REFERENCE TO RELATED APPLICATIONS

This application is a continuation of U.S. application Ser. No. 12/703,986 filed on Feb. 11, 2010 (now U.S. Pat. No. 8,017,371), which is a continuation of U.S. application Ser. No. 11/624,750 filed on Jan. 19, 2007 (abandoned), which is a Continuation in Part of PCT/DK2005/000515 filed Aug. 2, 2005, which claims priority or the benefit under 35 U.S.C. 119 of U.S. provisional application No. 60/598,150 filed Aug. 2, 2004, the contents of which are fully incorporated herein by reference.

FIELD OF THE INVENTION

The present invention relates to a method of constructing a hybrid polypeptide from two or more parent polypeptides in order to create diversity. It also relates to hybrid polypeptides constructed by this method.

BACKGROUND OF THE INVENTION

The prior art describes methods of creating diversity by recombination of DNA sequences encoding two or more polypeptides, followed by transformation of a suitable host organism with the recombined DNA sequence and screening of the transformants for enzymatic activity. The recombination may be random or directed. WO 1995022625; U.S. Pat. No. 6,368,805; J. E. Ness et al., Nature Biotechnology, vol. 20, December 2002, pp. 1251-1255; M. C. Saraf et al., 4142-4147, PNAS, Mar. 23, 2004, vol. 101, No. 12.

SUMMARY OF THE INVENTION

The inventors realized that the diversity generated by conventional methods may be limited by steric hindrance between amino acid residues in the three-dimensional structures of the resulting polypeptides. The steric hindrance (also referred to as "structural stop codon") may occur between amino acid residues at widely different positions in the amino acid sequences, e.g. between residues in two different domains of the 3D structure, and resulting polypeptides which include such steric hindrance may never be observed in the conventional recombination methods because they may be expressed in poor yields or may have poor activity or stability.

The removal of "structural stop codons" can result in improved expression and/or stability of the protein of interest, or in ultimate case expression at all of protein of interest. For example in combining of two or more proteins, i.e. combining multiple hybrids of two or more proteins using various DNA techniques e.g. using shuffling techniques as known in the art (WO9522625, WO9827230 and WO2000482862) the removal of "structural stop codons" from one or more of the included proteins will improve the expression and/or stability of the proteins, and/or create access to a novel diversity not found by other shuffling or hybrid techniques. Combination of protein sequences will often result in accommodation of different sized residues and homologous positions, but not always. Sometimes clashes will occur and especially in the core of the protein. The removal of "structural stop codons" results in novel diversity due to allowance of new region combinations not seen because of presence of "structural stop codons", which otherwise may result in a non functional or non expressed protein.

The inventors developed a method to identify and alleviate such steric hindrance in the resulting polypeptides. In an alignment of the three-dimensional structures, steric hindrance is indicated when residues from two different structures are located within a certain distance. Pairs of residues at corresponding positions in the amino acid sequences are not taken into consideration since only one of the two residues is expected to be present in the recombined polypeptide. Pairs of residues are not taken into consideration if one or both is glycine or if one or both side chains is close to the surface (indicated by a high solvent accessibility) as the residue may be able to reposition to avoid the potential clash.

Accordingly, the invention provides a method of constructing a polypeptide, comprising:

a) selecting at least two parent polypeptides each having an amino acid sequence and a three-dimensional structure, b) structurally aligning the three-dimensional structures, thereby aligning amino acid residues from different sequences, c) selecting a first amino acid residue from one structure and a second residue from another structure, such that:
   i) the two residues are not aligned in the superimposition,
   ii) a non-hydrogen atom of the first residue and a non-hydrogen atom of the second residue are located less than 2.7 Å apart, and
   iii) each of the two residues is not Glycine and has a side chain having less than 30% solvent accessibility, and d) substituting or deleting the first and/or the second residue such that the substitution is with a smaller residue, and e) recombining the amino acid sequences after the substitution, and f) preparing a DNA-sequence encoding the polypeptide of step e) and expressing the polypeptide in a transformed host organism.

Further the invention relates to a polypeptide which has at least 80%, 85%, 90%, 95% or 98% or 99% identity to SEQ ID NO: 18 or 19 or 20 or 21 or 22 or 23 or 24 or 25. The invention also relates to a polynucleotide encoding any of the polypeptides.

BRIEF DESCRIPTION OF DRAWINGS

FIG. 1 shows an alignment of various known CGTase sequences. Details are given below.

FIG. 2 shows the results of a comparison of two 3D structures. The upper sequence is 1qho for the maltogenic alpha-amylase Novamyl (SEQ ID NO: 17), and for the lower sequence is 1a47 for a CGTase (SEQ ID NO: 5). Details are described in Examples 1 and 2.

DETAILED DESCRIPTION OF THE INVENTION

Parent Polypeptides

Figure 3:
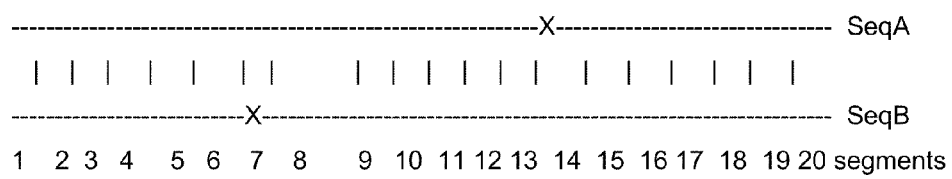
FIGS. 3 and 4 shows hypothetical sequences with "structural stop codons". Details are described in Examples 6 and 7.

According to the invention, two or more parent polypeptides are selected, each having an amino acid sequence and a three-dimensional structure. The parent polypeptides may in particular be selected so as to be structurally similar, e.g. each pair having a amino acid identity of at least 50%, e.g. at least 60%, 70%, 80%, 90%, 95%, 96%, 97%, 98%, or 99%. Amino acid identity may be determined as described in U.S. Pat. No. 6,162,628.

In another preferred embodiment the structurally similar parent polypeptides have a homology of at least 50%, e.g. at least 60%, 70%, 80%, 90%, 95%, 96%, 97%, 98%, or 99%. Homology may be determined as described in WO 2004067737, i.e. by using the GAP routine of the UWGCG package version 9.1.

The parent polypeptides may be polypeptides having biological activity, structural polypeptides, transport proteins, enzymes, antibodies, carbohydrate binding modules, serum albumin (e.g. human and bovine), insulin, ACTH, glucagon, somatostatin, somatotropin, thymosin, parathyroid hormone, pituitary hormones, somatomedin, erythropoietin, luteinizing hormone, interleukin, chorionic gonadotropin, hypothalamic releasing factors, antidiuretic hormones, thyroid stimulating hormone, relaxin, interferon, thrombopoeitin (TPO) and prolactin.

The enzyme may have an active site, e.g. a catalytic triad, which may consist of Ser, Asp and His. The parent enzymes may be selected so as to have identical residues in the active site.

Three-Dimensional Structure

Three-dimensional structure is meant to be a known crystal structure or a model structure.

The 3D structure of each polypeptide may already be known, or it may be modeled using the known 3D structures of one or more polypeptides with a high sequence homology, using an appropriate modeling program such as Homology, Modeller or Nest. The 3D model may be optimized using molecular dynamics simulation as available, e.g., in Charmm or NAMD. The optimization may particularly be done in a water environment, e.g. a box or sphere.

The Homology, Modeller and Charmm software is available from Accelrys Inc., 9685 Scranton Road, San Diego, Calif. 92121-3752, USA, accelrys.com/. The Nest software is distributed free of charge at trantor.bioc.columbia.edu/programs/jackal/index.html. The NAMD software is available at ks.uiuc.edu/Research/namd/.

Structural Alignment of 3D Models

The 3D models may be structurally aligned by methods known in the art. The structural alignment may be done by use of known software. In the structurally aligned models, pairs of residues from different sequences are considered to be aligned when they are located close to each other. The following software may be used:

DALI software, available at ebi.ac.uk/dali/
CE software available at cl.sdsc.edu/
STAMP software available at compbio.dundee.ac.uk/Software/Stamp/stamp.html
Protein 3Dhome at lecb.ncifcrf.gov/~tsai/
Yale Gernstein Lab—spare parts at bioinfo.mbb.yale.edu/align/
Structural alignment server at molmovdb.org/align/

In the case of enzymes having an active site, the structural alignment may be a superimposition of the structures based on the deviations of heavy atoms (i.e. non-hydrogen atoms) in the active sites, e.g. by minimizing the sum of squares of deviations. Alternatively, the superimposition may be done so as to keep deviations between corresponding atoms below 0.8 Å, e.g. below 0.6 Å, below 0.4 Å below 0.3 Å or below 0.2 Å.

Selection of Amino Acid Residues

Steric hindrance ("potential clashes") between two amino acid residues is indicated if a heavy atoms (i.e. non-hydrogen) of the two residues are located less than 2.7 Å, 2.5 Å or 2.0 Å apart, particularly less than 1.7 Å, 1.5 Å, 1.2 Å, 1.1 Å or 1.0 Å apart, with the following exceptions:

Two residues aligned with each other in the structural alignment (pairs of residues at corresponding positions in the amino acid sequences) are not taken into consideration since only one of the two residues is expected to be present in the recombined polypeptide.

Pairs of residues are not taken into consideration if one or both is glycine.

Pairs of non-glycine residues are not taken into consideration if one or both side chains has more than 20%, 25% or 30% solvent accessibility as a high solvent accessibility is taken as an indication that the residue may be able to reposition to avoid the potential clash. Solvent accessibility can be calculated by use of the DSSP program, available from Centre for Molecular and Biomolecular Informatics, University of Nijmegen, Toernooiveld 1, P.O. Box 9010, 6500 GL Nijmegen, +31 (0)24-3653391, cmbi.kun.nl/gv/dssp/. The DSSP program is disclosed in W. Kabsch and C. Sander, BIOPOLYMERS 22 (1983) pp. 2577-2637. The residue total surface areas of the 20 natural amino acids are tabulated in Thomas E. Creighton, PROTEINS; Structure and Molecular Principles, W.H. Freeman and Company, NY, ISBN: 0-7167-1566-X (1984).

To confirm the severity of the potential clash, a local alignment of the two 3D structures may then be made by aligning all residues within a distance of 10 Å.

The steric hindrance may be identified by a comparison of two complete sequences in order, particularly severe clashes (less than 1.2, 1.1 or 1.0 Å apart), to identify potential clashes that may arise no matter how the two sequences are recombined.

Alternatively, the comparison may be made between two partial sequences to be combined in a hybrid, and in this case a larger limit may be used for the distance (less than 2.7 Å, 2.5 Å, 2.0 Å, 1.7 Å or 1.5 Å).

Amino Acid Substitution

When a potential clash between two residues has been identified, one or both residues is substituted with a smaller residue. In this connection, the residues are ranked as follows from smallest to largest: (an equal sign indicates residues with sizes that are practically indistinguishable):

$G<A=S=C<V=T<P<L=I=N=D=M<E=Q<K<H<R<F<Y<W$

The substitution may be such that the two residues after the substitution can form a hydrogen bond, a salt bridge or a cysteine bridge.

Recombination of Amino Acid Sequences

After making amino acid substitutions to alleviate potential clashes, the substituted amino acid sequences are recombined. The recombination may be done by designing hybrids or by gene shuffling.

Hybrids may be constructed by switching from one sequence to another between aligned residues. Once constructed, the hybrids can be produced by conventional methods by preparing a DNA sequence encoding it and expressing it in a transformed host organism.

Alternatively, genes can be prepared encoding each substituted amino acid sequence, by shuffling the genes by known methods, transforming a suitable host organism with the shuffled genes. The shuffling can be done, e.g., as described in WO 1995022625.

In the case of the parent polypeptides being enzymes, the transformants can be screened for enzymatic activity.

Enzymes

The parent enzymes may have hydrolase, oxidoreductase or transferase activities, e.g. activities such as protease, lipolytic enzyme, glycosyl hydrolase, laccase, oxidoreductases with oxygen as acceptor (e.g. glucose oxidase, hexose oxidase or galactose oxidase), glycosyl transferase, esterase, cellulase, xylanase, amylase, isoamylase, pullulanase, branching enzyme, pectate hydrolase, cyclodextrin glucanotransferase, or maltogenic alpha-amylase activity. One or more of the parent enzymes may have a carbohydrate-binding domain.

The method may particularly be applied to two or more structurally similar enzymes, e.g. belonging to the same family in a structural classification of enzymes. Thus, they may belong to the same structural family for glycosyl hydrolases and glycosyl transferases as described, e.g., in the following literature. The enzymes may be of family 13 and may particularly include a maltogenic alpha-amylase and a cyclodextrin glucanotransferase.

Henrissat B., A classification of glycosyl hydrolases based on amino-acid sequence similarities. Biochem. J. 280: 309-316 (1991).

Henrissat B., Bairoch A. New families in the classification of glycosyl hydrolases based on amino-acid sequence similarities. Biochem. J. 293:781-788 (1993).

Henrissat B., Bairoch A. Updating the sequence-based classification of glycosyl hydrolases. Biochem. J. 316: 695-696 (1996).

Davies G., Henrissat B. Structures and mechanisms of glycosyl hydrolases. Structure 3:853-859 (1995).

The parent enzymes may be lipolytic enzymes belonging to the same homologous family as described at led.uni-stuttgart.de/families.html. The 3D structures of the lipolytic enzymes may all include a so-called "lid" in open or closed form.

The enzymes may be proteases or peptidases belonging to the same family or subfamily as described by MEROPS in "the Peptidase Database", available at merops.sanger.ac.uk/. The proteases may be subtilases, e.g. belonging to the same sub-group as described by Siezen R J and Leunissen J A M, 1997, Protein Science, 6, 501-523; one of these sub-groups is the Subtilisin family.

CGTase

The cyclodextrin glucanotransferase (CGTase) may have an amino acid sequence as shown in SEQ ID NOS: 1-16 and may have a three-dimensional structure found under the following identifier in the Protein Data Bank (rcsb.org): *B. circulans* (1CDG), alkalophilic *Bacillus* (1 PAM), *B. stearothermophilus* (1CYG) or *Thermoanaerobacterium thermosulfurigenes* (1 CIU, 1A47). 3D structures for other CGTases may be constructed as described in Example 1 of WO 9623874.

FIG. 1 shows an alignment of the following known CGTase sequences, each identified by accession number in the GeneSeqP database and by source organism. Some sequences include a propeptide, but only the mature peptide is relevant for this invention.

SEQ ID NO: 1. aab71493.gcg *B. agaradherens*
SEQ ID NO: 2. aau76326.gcg *Bacillus agaradhaerans*
SEQ ID NO: 3. cdg1_paema.gcg *Paenibacillus macerans* (*Bacillus macerans*).

SEQ ID NO: 4. cdg2_paema.gcg *Paenibacillus macerans* (*Bacillus macerans*).
SEQ ID NO: 5. cdgt_thetu.gcg *Thermoanaerobacter thermosulfurogenes* (*Clostridium thermosulfurogenes*) (SEQ ID NO: 2:)
SEQ ID NO: 6. aaw06772.gcg *Thermoanaerobacter thermosulphurigenes* sp. ATCC 53627 (SEQ ID NO: 3)
SEQ ID NO: 7. cdgt_bacci.gcg *Bacillus circulans*
SEQ ID NO: 8. cdgt_bacli.gcg *Bacillus* sp. (strain 38-2)
SEQ ID NO: 9. cdgt_bacs0.gcg *Bacillus* sp. (strain 1011)
SEQ ID NO: 10. cdgt_bacs3.gcg *Bacillus* sp. (strain 38-2)
SEQ ID NO: 11 cdgu_bacci.gcg *Bacillus circulans*
SEQ ID NO: 12. cdgt_bacsp.gcg *Bacillus* sp. (strain 17-1, WO 2003068976) (SEQ ID NO: 4)
SEQ ID NO: 13. cdgt_bacoh.gcg *Bacillus ohbensis*
SEQ ID NO: 14. cdgt_bacs2.gcg *Bacillus* sp. (strain 1-1)
SEQ ID NO: 15. cdgt_bacst.gcg *Bacillus stearothermophilus*
SEQ ID NO: 16. cdgt_klepn.gcg *Klebsiella pneumoniae*

To develop variants of a CGTase without a known 3D structure, the sequence may be aligned with a CGTase having a known 3D structure. An alignment for a number of CGTase sequences is shown in FIG. 2. Other sequences may be aligned by conventional methods, e.g. by use of the software GAP from UWGCG Version 8.

Maltogenic Alpha-Amylase

The maltogenic alpha-amylase (EC 3.2.1.133) may have the amino acid sequence shown in SEQ ID NO: 17 (in the following referred to as Novamyl), having the 3D structure described in U.S. Pat. No. 6,162,628 and found in the Protein Data Bank with the identifier 1QH0. Alternatively, the maltogenic alpha-amylase may be a Novamyl variant described in U.S. Pat. No. 6,162,628. A 3D structure of such a variant may be developed from the Novamyl structure by known methods, e.g. as described in T. L. Blundell et al., Nature, vol. 326, p. 347 ff (26 Mar. 1987); J. Greer, Proteins: Structure, Function and Genetics, 7:317-334 (1990); or Example 1 of WO 9623874.

Use of Hybrid Polypeptide

The hybrids may be useful for the same purpose as the parent enzymes.

Thus, a hybrid of a maltogenic alpha-amylase and a cyclodextrin glucanotransferase may form linear oligosaccharides as an initial product by starch hydrolysis and a reduced amount of cyclodextrin and may be useful for anti-staling in baked products.

A hybrid of laccases and/or other enzymes belonging to EC 1.10.3 may be useful for e.g. hair dyeing or reduction of malodor.

EXAMPLES

Example 1

Comparison of Complete Sequences

Superimposition of Parent Enzymes

Two glycosyl hydrolases of family 13 were selected. One was a maltogenic amylase (Novamyl) having the amino acid sequence shown in SEQ ID NO: 17 and having a 3D structure published under number 1 QHO. The other was a CGTase having the amino acid sequence shown in SEQ ID NO: 5 and the 3D structure 1A47, and this was also taken to represent the structure of the highly homologous CGTase having the sequence SEQ ID NO: 6. The two 3D structures were superimposed so as to align the active sites, and the alignment of residues of the two sequences is shown in FIG. 2 Aligned residues shown vertically above each other, with gaps inserted to separate non-aligned residues.

Identification of Potential Clashes

The two structures were analyzed, and the following unaligned residues were identified as having a side chain with less than 30% solvent accessibility and with a heavy atom less than 1.5 Å (or less than 1.0 Å) apart from a heavy atom of a residue in the other structure. The following pairs of residues were found to come within 1.0 Å. The potential clashes are shown as CGTase residue and atom, Novamyl residue and atom, and distance in Å:

| D209 | OD2 | A676 | CB | 0.89 |
|------|-----|------|-----|------|
| L261 | CD1 | K270 | NZ | 0.93 |
| D267 | CG | N266 | O | 0.94 |
| D267 | OD1 | N266 | O | 0.48 |
| M307 | CE | L286 | CD1 | 0.77 |
| H503 | CD2 | K7 | NZ | 0.97 |
| T509 | OG1 | Y574 | CZ | 0.65 |
| V626 | CB | Y181 | CZ | 0.41 |
| V626 | CG1 | Y181 | OH | 0.99 |
| V626 | CG2 | Y181 | CD2 | 0.76 |
| K651 | NZ | P592 | CG | 0.35 |

The above residues are marked by asterisks in FIG. 2.

Example 2

Comparison of Complementary Sequences

To design hypothetical hybrids, residues in a partial sequence of Novamyl (SEQ ID NO: 17) were compared with residues in the complementary part of the CGTase sequence (SEQ ID NO: 6), and residues with heavy atoms located less than 1.7 Å apart were identified. The potential clashes are shown as in Example 1. The identified residues are marked with asterisks in FIG. 2.

Novamyl 1-494+CGTase 495-683

| H503 | CD2 | K7 | NZ | 0.97 |
|------|-----|-----|-----|------|
| N575 | O | Y317 | OH | 1.68 |
| V626 | CB | Y181 | CZ | 0.41 |

CGTase 1-494+Novamyl 495-686

| D3 | C | R545 | NH2 | 1.36 |
|----|---|------|-----|------|
| D209 | OD2 | A676 | CB | 0.89 |

Novamyl 1-499+CGTase 500-683

| H503 | CD2 | K7 | NZ | 0.97 |
|------|-----|-----|-----|------|
| N575 | O | Y317 | OH | 1.68 |
| V626 | CB | Y181 | CZ | 0.41 |

CGTase 1-499+Novamyl 500-686

| D3 | C | R545 | NH2 | 1.36 |
|----|---|------|-----|------|
| D209 | OD2 | A676 | CB | 0.89 |

Novamyl 1-410+CGTase 410-683

| H503 | CD2 | K7 | NZ | 0.97 |
|------|-----|-----|-----|------|
| N575 | O | Y317 | OH | 1.68 |
| V626 | CB | Y181 | CZ | 0.41 |

Novamyl 1-378+CGTase 378-683

| N409 | OE1 | R354 | N | 1.63 |
|------|-----|------|---|------|
| H503 | CD2 | K7 | NZ | 0.97 |
| N575 | O | Y317 | OH | 1.68 |
| V626 | CB | Y181 | CZ | 0.41 |

Novamyl Residues 1-204+CGTase Residues 207-683

| W219 | CZ2 | L75 | CD2 | 1.66 |
|------|-----|-----|-----|------|
| H503 | CD2 | K7 | NZ | 0.97 |
| V626 | CB | Y181 | CZ | 0.41 |

CGTase Residues 1-139 and 207-683+Novamyl Residues 131-204

| V626 | CB | Y181 | CZ | 0.41 |
|------|-----|------|-----|------|

Example 3

Construction of Hybrids

Hybrids were constructed with the following combinations of Novamyl residues and CGTase residues (SEQ ID NO: 6) and with substitutions of Novamyl residues as indicated to alleviate potential clashes. For comparison, similar variants were constructed without substitutions.

| Residues | Novamyl substitutions |
|----------|----------------------|
| Novamyl 1-494 + CGTase 495-683 | K7S + Y181A |
| CGTase 1-494 + Novamyl 495-686 | R545S |
| Novamyl 1-499 + CGTase 500-683 | K7S + Y181A |
| CGTase 1-499 + Novamyl 500-686 | R545S |
| Novamyl 1-410 + CGTase 410-683 | K7S + Y181A |
| Novamyl 1-378 + CGTase 378-683 | K7S + Y181A |
| Novamyl 1-204 + CGTase 207-683 | K7S, W107F |
| CGTase 1-139 + Novamyl 131-204 + CGTase 207-683 | Y181A |
| Novamyl 1-204 + CGTase 207-683 | K7S, W107F, Y181A |
| Novamyl 1-204 + CGTase 207-683 | K7S, Y181A |

The first eight of the above hybrids are found in SEQ ID NO: 18 to SEQ ID NO: 25.

Example 4

Screening of Hybrids for Amylase Activity

Four hybrids of the previous example were produced by preparing a DNA-sequence encoding the hybrid and expressing the hybrid in a transformed organism cultivating a transformant, and the amylase activity was assayed by letting the culture broth act on Phadebas (dye-labelled substrate, available from Pharmacia) and measuring the absorbance at 650 nm. The amylase assay was made at pH 5.5 at two different temperatures: 50° C. and 60° C. Reference hybrids without substitutions were included for comparison.

| Residues | Novamyl substitutions | ABS (650 nm) pH 5.5, 60° C. | ABS (650 nm) pH 5.5, 50° C. |
|---|---|---|---|
| Novamyl 1-410 + CGTase 410-683 | — | 0.01 | 0.01 |
| Novamyl 1-410 + CGTase 410-683 | K7S, Y181A | 0.49 | 1.66 |
| Novamyl 1-378 + CGTase 378-683 | — | 0.01 | 0.01 |
| Novamyl 1-378 + CGTase 378-683 | K7S, Y181A | 0.16 | 0.37 |
| CGTase 1-139 + Novamyl 131-204 + CGTase 207-683 | — | 0.06 | 0.02 |
| CGTase 1-139 + Novamyl 131-204 + CGTase 207-683 | Y181A | 0.21 | 0.07 |

Example 5

Baking with Hybrids

Further two hybrids were produced by cultivating a transformant and tested for baking. The two hybrids are:
BaHy1: CGTase (SEQ ID NO: 6) residue 1-139+Novamyl (SEQ ID NO: 17) residue 131-204+CGTase (SEQ ID NO: 6) residue 207-683; and
BaHy2: Novamyl (SEQ ID NO: 17) residue 1-577+CGTase (SEQ ID NO: 6) residue 580-683+Y181A mutation in Novamyl.
The effect of the two hybrids in straight dough was compared to that of CGTase with respect to a number of parameters: Softness of breadcrumb, elasticity, and mobility of free water. Approximately 1 mg/kg of flour was dosed.
The two hybrids improve the softness of breadcrumb as compared to CGTase.
The two hybrids improve the elasticity as compared to CGTase.
BaHy2 improves the mobility of free water as compared to CGTase, whereas BaHy1 has the same effect as CGTase.

Example 6

Structural Stop Codons—Impact on Diversity

This example illustrates the possible outcome of a hybridization between two proteins having the sequences SeqA and SeqB (FIG. 3):
If combination sites (marked with |) comprises a "structural stop codon" (marked with X), the resulting protein not be expressed properly or maybe even not at all. Segment 14 in SeqA and segment 7 in SeqB indicates such potential clashes due to the presence of "structural stop codons". The result will be a lowering of the diversity, as combinations containing these two segments most likely not will be able to accommodate the clashes and therefore not be present in the diversity of protein molecules.

If X in SeqA and/for SeqB is made smaller the accommodation might result in a functional protein. Accommodation may also be obtained by changing the shape or charge of the residue e.g. I to L and D to N. The "structural stop codon" can also be removed by inserting the proper match of residues by mutating the particular residues and/or mutating the surrounding residues around the clashing residues thus creating accommodation. Smaller residues can be found in the list; $G<A=S=C<V=T<P<L=I=N=D=M<E=Q<K<H<R<F<Y<W$.

If the "structural stop codon" gives 100% non-functional protein—the lowering of diversity is 25% for one "structural stop codon" residue pair—compared to the situation without any "structural stop codons". That is the diversity for the segments are $2^{20}=1048576$ and for the clashes it is $2^{18}=262144$.

Example 7

Figure 4:
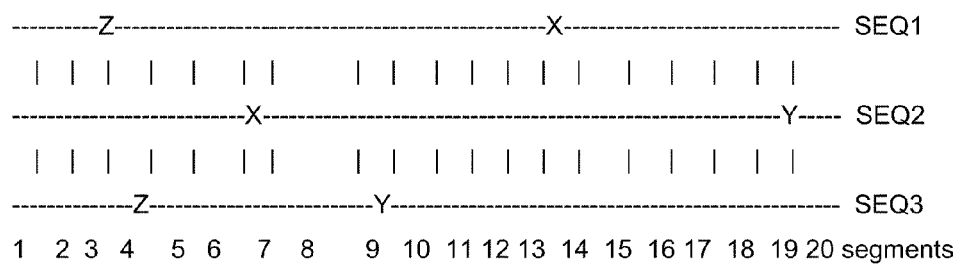

Structural Stop Codons—Impact on Diversity when Combining More than Two Proteins In this example we have three proteins illustrated by SEQ1, SEQ2 and SEQ3 (FIG. 4). SEQ1 has a "structural stop codon" with SEQ2 called X. SEQ1 has a "structural stop codon" with SEQ3 called Z, and SEQ 2 has a "structural stop codon" with SEQ3 called Y. The diversity will hereby be lowered dramatically as exemplified above. We will have the common equation for the number of non-"structural stop codon" containing proteins termed D for diversity in the cases where the "structural stop codons" pairs are found in separate segments not containing other "structural stop codons" and the number of segments are higher or equal to the number of pairs:

$$D=N^K-P*N^{(K-2)} \qquad \text{Equation I}$$

where D is diversity without "structural stop codons", N the number of proteins, K the number segments, and P the number of pairs (ie. X, Y and Z).

For other situations e.g. with "structural stop codons" in the same segment or other situations other equations can be derived.

Using equation I we get D to be ⅔ for the numbers shown in present example and for the numbers in shown in the above example we get 0.75. Consequently the diversity may be increased significantly by removing "structural stop codons".

Example 8

Structural Stop Codons—Impact on Extending Combination Possibilities for Proteins with Low Homology to a Better Result One important aspect is the possibility of combining more distant related proteins by hybridisation or shuffling techniques and not only closely related proteins. The combination by hybridisation or shuffling techniques may go below the 90, or the 80, or the 70, or the 60, or the 50 percent homology level. At the upper level of homology, around 70-90 percent homology, the amount of diversity—meaning the number of active clones coming out of a hybridisation or shuffling experiment—or at the lower level around 50-80 percent homology creation of active clones at all might be the outcome.

Example 9

Example on Finding "Structural Stop Codons" for Combining Proteins E.G. Shuffling or Hybrid Formation The set of parent sequences are analyzed using the 3D structures. The 3D structures can be based on existing known structures or obtained by X-ray crystallography, NMR methods or modeled using appropriate modeling programs like NEST, MODELLER or HOMOLOGY. The two structures are superimposed by optimizing the RMSD of the C-alpha atom distances using a appropriate program as listed in the description. The superimposed structures are analyzed for possible clashes between residues. For each type of atoms (a,b), where atom a is in structure A and atom b is in structure B the distance d(a,b) between the atoms is calculated as the standard Euclidian distance. All atom pairs with distance smaller than a given predefined threshold are potentially structural clashes. A set of rules is imposed to filter out atom pairs with distance smaller than the threshold which are not to be considered as clashes. The rules are:
  i. Atom pairs that form part of the residue that are aligned in the alignment based on the superimposition are filtered out.
  ii. Atom pairs that form part of residues that are adjacent to aligned residue are filtered out.
  iii. Atom pairs where both atoms are backbone atoms are filtered out.
  iv. Atom pairs that form part of residues that are both surface exposed are filtered out.

Surface exposed can be computed based on the "solvent exposed surface area" computed by the DSSP-program by division by the standard accessibilities in the following list; A=62, C=92, D=69, E=156, F=123, G=50, H=130, I=84, K=174, L=97, M=103, N=85, P=67, Q=127, R=211, S=64, T=80, V=81, W=126 and Y=104. The threshold for interatomic distances can be 3 Å, or 2.7 Å, or 2.5 Å or 2.3 Å, or 2.1 Å or 2 Å. The minimal relative surface exposed area for filtering out an atom pair is 20% or preferably 30% for each residue. The found clashes are visualized and inspected in a graphic display program.

Example 10

"Structural Stop Codons" for Combining Protease—Subtilisin S8A

After the superimposition of the two X-ray structures of BPN' (1SBT—also disclosing the amino acid sequence) and Savinase (1SVN—also disclosing the amino acid sequence) using a suitable display software like INSIGHT II from Accellrys inc. a "structural stop codon" can be found i.e. a clash between to residues with distance lower than a certain threshold here 2.5 Å. The residues giving a clash can be seen are located in the core of the two proteins and having the following residues below 2.5 Å apart to I198 from Savinase structure 1SVN and I268 BPN' 3D structure 1SBT. Mutation of either 1SVN to I198V or A or G or T, or the SBT sequence to I268V or A or G or T will remove the interaction.

So for example making the hybrid construction 1SVN sequence A1-G219 and 1SBT sequence N218-Q275 should include the mutations suggested above to obtain the best result regarding expression.

Example 11

"Structural Stop Codons" for Combining Protease TY145 and Savinase

After the superimposition of the two X-ray structures of TY145 (see patent application WO2004067737 A3, also disclosing the amino acid sequence (SEQ ID NO: 1)) and Savinase (1SVN—also disclosing the amino acid sequence) using a suitable display software like INSIGHT II from Accellrys inc. a "structural stop codon" can be found i.e. a clash between to residues with distance lower than a certain threshold here 2.1 Å:
TY145 P308 clashes with Savinase I198
TY145 W101 clashes with Savinase M119
TY145 I03 clashes with Savinase W113
Savinase Y263 clashes with TY145 Mainchain

Example 12

"Structural Stop Codons" for Combining Lipases

Two hybrid enzymes consisting of the N-terminal from *Thermomyces lanuginosus* lipase (TLL, SEQ ID NO: 26) and the C-terminal from *Fusarium* sp. lipase (KVL, SEQ ID NO: 27) have been constructed (Construct 1 and Construct 2). The point of crossover resides within conserved regions within the two enzymes. A study of the three-dimensional structure of *Thermomyces lanuginosus* lipase 1 GT6 and a model of the *Fusarium* sp. lipase build based on the 1GT6 structure reveals two places of residue clashes when making the two hybrid constructs.

In general the following "structural stop codons" can be found:
TLL F142 clashes with KVL F136
TLL T64 clashes with KVL F24
TLL I222 clashes with KVL Y226
TLL F80 clashes with KVL I60
TLL F55 clashes with KVL A62

The structural problem has been alleviated by introduction of the following mutations T64G and T64G/I222L into the two hybrid enzymes Construct 1 and Construct 2, respectively.

The constructs for two specific hybrids are (the numbers are taken for KVL and TLL protein sequences):
  Construct 1. KVL 1-28 and TLL 29-269
  Construct 2. KVL 1-28 and TLL 29-227 and KVL 225-267
  Construct 3. KVL 1-28 and TLL 29-269 and TLL T64G
  Construct 4. KVL 1-28 and TLL 29-227 and KVL 225-267 and TLL T64G and TLL I222L The 3D structures of the KVL lipase was build using the Accelrys software HOMOLOGY program—other suitable software like NEST could also be used.

Example 13

"Structural Stop Codons" for Combining Laccases

Analyzing the three dimensional structure of the *Coprinus cinerius* laccase (CLL, SEQ ID NO:28) and the three dimensional structure model of *Myceliophthora thermophila* laccase (MTL, SEQ ID NO: 29) build using the NEST software based on the *Melanocarpus albomyces* laccase structure (1 GWO—also disclosing the amino acid sequence), it can be found that several "structural stop codons" can be found. Focusing on the core "structural stop codons" the following residues can found to be important to mutate. There are the following important "structural stop codons" that has to be removed before attempting shuffling of the two laccases of CCL and MTL:

MTL M301A and/or CCL F124L
CCL E239A or D
CCL E453A
MTL W464L
MTL W420F

There are besides the mentioned changes other important issues concerning the cystin bridges MTL C301/C267 and CCL C135/C222. Securing of no overlaps in theses regions are of great importance. To avoid the problems the following are a plausible way to go further:

MTL C379S/C345β and CCL C135G/C222V

Alternatively "transfer" CCL cystinbridge to MTL: MTL G193C/V281C.

Example 14

"Structural Stop Codons" for Combining Xylanases

Analysing the three dimensional structure of the *Bacillus agaradherens* xylanase (BAX), having the X-ray structure 1QH7 (also disclosing the amino acid sequence), and the three dimensional structure of *Bacillus halodurans* xylanase (BHX) having the X-ray structure 1βNB (also disclosing the amino acid sequence), it can be found that several "structural stop codons" can be found. Focusing on the core "structural stop codons" the following residues can found to be important to mutate:

BAX R49 clashes with BHX Y165
BAX K53 clashes with BHX Y5
BAX K136+E56 clashes with BHX R73
BAX F163 clashes with BHX F145
BAX L199 clashes with BHX W42
BAX M28 clashes with BHX W6

Analysing the three dimensional structure of the *Bacillus agaradherens* xylanase (BAX), having the X-ray structure 1βH7, and the three dimensional structure model of *Paenibacillus* sp. xylanase (PSX) having the X-ray structure 1BVV (also disclosing the amino acid sequence), it can be found that several "structural stop codons" can be found. Focusing mostly on the core "structural stop codons" the following residues can found to be important to mutate:

BAX R49 clashes with PSX Y166+Q7
BAX K53 clashes with PSX Y5
BAX L199 clashes with PSX W42
BAX F163 clashes with PSX F146
BAX M28 clashes with PSX W6
BAX Y195 clashes with PSX N54.

The invention claimed is:

1. An isolated polypeptide which has at least 90% amino acid sequence identity to the amino acid sequence of SEQ ID NO: 19, and wherein the polypeptide has starch hydrolyzing activity.

2. A dough comprising the polypeptide of claim 1.

3. The polypeptide of claim 1, which has at least 95% amino acid sequence identity to the amino acid sequence of SEQ ID NO: 19.

4. The polypeptide of claim 1, which has at least 98% amino acid sequence identity to the amino acid sequence of SEQ ID NO: 19.

5. The polypeptide of claim 1, which has at least 99% amino acid sequence identity to the amino acid sequence of SEQ ID NO: 19.

6. An isolated polypeptide comprising the amino acid sequence of SEQ ID NO: 19, wherein the polypeptide has starch hydrolyzing activity.

7. The polypeptide of claim 6, consisting of the amino acid sequence of SEQ ID NO: 19.

* * * * *

SEQUENCE LISTING

```
<160> NUMBER OF SEQ ID NOS: 29

<210> SEQ ID NO 1
<211> LENGTH: 713
<212> TYPE: PRT
<213> ORGANISM: Bacillus agaradherens

<400> SEQUENCE: 1

Met Ser Lys Lys Thr Leu Lys Arg Leu Leu Ala Leu Val Val Val Leu
1               5                   10                  15

Phe Ile Leu Ser Gly Ser Gly Ile Leu Asp Phe Ser Ile Thr Ser Ala
            20                  25                  30

Asn Ala Gln Gln Ala Thr Asp Arg Ser Asn Ser Val Asn Tyr Ser Thr
        35                  40                  45

Asp Gly Ile Tyr Gln Ile Val Thr Asp Arg Phe Tyr Asp Gly Asp Glu
    50                  55                  60

Ser Asn Asn Pro Ser Gly Glu Leu Tyr Ser Glu Gly Cys Lys Asn Leu
65                  70                  75                  80

Arg Lys Tyr Cys Gly Gly Asp Trp Gln Gly Ile Ile Asp Lys Ile Asp
                85                  90                  95

Asp Gly Tyr Leu Thr Asn Met Gly Val Thr Ala Leu Trp Ile Ser Pro
            100                 105                 110

Pro Val Glu Asn Ile Phe Glu Thr Ile Asp Asp Glu Ser Gly Thr Thr
        115                 120                 125

Ser Tyr His Gly Tyr Trp Ala Arg Asp Tyr Lys Lys Thr Asn Pro Phe
    130                 135                 140

Phe Gly Ser Thr Glu Asp Phe Glu Arg Leu Ile Glu Thr Ala His Ser
145                 150                 155                 160

His Asp Ile Lys Ile Val Ile Asp Leu Ala Pro Asn His Thr Ser Pro
                165                 170                 175

Ala Asp Phe Asp Asn Pro Asn Tyr Ala Glu Asn Gly Ile Leu Tyr Asp
            180                 185                 190
```

```
Asn Gly Asn Tyr Val Ser Ser Tyr Ser Asp Asn Ser Asp Leu Phe Leu
        195                 200                 205

Tyr Asn Gly Gly Thr Asp Phe Ser Thr Tyr Glu Asp Glu Ile Tyr Arg
        210                 215                 220

Asn Leu Phe Asp Leu Ala Ser Phe Asn His Ile Asn Ala Glu Leu Asn
225                 230                 235                 240

Asn Tyr Leu Glu Asp Ala Val Lys Lys Trp Leu Asp Leu Gly Ile Asp
                245                 250                 255

Gly Ile Arg Ile Asp Ala Val Ala His Met Pro Pro Gly Trp Gln Lys
                260                 265                 270

Ala Tyr Met Asp Thr Ile Tyr Asp His Arg Ala Val Phe Thr Phe Gly
            275                 280                 285

Glu Trp Phe Thr Gly Pro Tyr Gly Asn Glu Asp Tyr Thr Lys Phe Ala
        290                 295                 300

Asn Asn Ser Gly Met Ser Val Leu Asp Phe Arg Phe Ala Gln Thr Thr
305                 310                 315                 320

Arg Asn Val Ile Gly Asn Asn Gly Thr Met Tyr Asp Ile Glu Lys
                325                 330                 335

Met Leu Thr Asp Thr Glu Asn Asp Tyr Asp Arg Pro Gln Asp Gln Val
                340                 345                 350

Thr Phe Leu Asp Asn His Asp Met Ser Arg Phe Thr Asn Asp Gly Glu
            355                 360                 365

Ser Thr Arg Thr Thr Asp Ile Gly Leu Ala Leu Met Leu Thr Ser Arg
        370                 375                 380

Gly Val Pro Thr Ile Tyr Tyr Gly Thr Glu Gln Tyr Met Glu Gly Asp
385                 390                 395                 400

Gly Asp Pro Gly Ser Arg Gly Met Met Glu Ser Phe Gly Glu Asn Thr
                405                 410                 415

Asp Ala Tyr Lys Leu Ile Gln Lys Leu Ala Pro Leu Arg Lys Ser Asn
            420                 425                 430

Pro Ala Tyr Gly Tyr Gly Thr Thr Lys Glu Arg Trp Ile Asn Asp Asp
        435                 440                 445

Val Ile Ile Tyr Glu Arg Asn Phe Gly Asp Asn Tyr Ala Leu Ile Ala
    450                 455                 460

Ile Asn Arg Asn Leu Asn Thr Ser Tyr Asn Ile Gln Gly Leu Gln Thr
465                 470                 475                 480

Glu Met Pro Ser Asn Ser Tyr Asp Asp Val Leu Asp Gly Leu Leu Asp
                485                 490                 495

Gly Gln Ser Ile Val Val Asp Asn Asn Gly Glu Val Asn Glu Phe Gln
            500                 505                 510

Met Ser Pro Gly Glu Val Gly Val Trp Glu Phe Glu Ala Thr Asn Val
        515                 520                 525

Asp Lys Pro Ser Ile Gly Gln Val Gly Pro Ile Ile Gly Glu Ala Gly
    530                 535                 540

Arg Thr Val Thr Ile Ser Gly Glu Gly Phe Gly Ser Ser Pro Gly Thr
545                 550                 555                 560

Val Gln Phe Gly Ser Thr Ser Ala Glu Ile Val Ser Trp Asn Asp Thr
                565                 570                 575

Val Ile Ile Ile Thr Val Pro Asn Asn Glu Ala Gly Tyr His Asp Ile
            580                 585                 590

Thr Val Val Thr Glu Asp Glu Gln Val Ser Asn Ala Tyr Glu Phe Glu
        595                 600                 605

Val Leu Thr Ala Asp Gln Val Thr Val Arg Phe Ile Ile Asp Asn Ala
    610                 615                 620
```

```
Glu Thr Lys Met Gly Glu Asn Ile Phe Leu Val Gly Asn Val His Glu
625                 630                 635                 640

Leu Gly Asn Trp Asp Pro Glu Gln Ser Val Gly Arg Phe Phe Asn Gln
            645                 650                 655

Val Val Tyr Gln Tyr Pro Thr Trp Tyr Tyr Asp Val Asn Val Pro Ala
                660                 665                 670

Asn Thr Asp Leu Glu Phe Lys Phe Ile Lys Ile Asp Gln Asp Asn Asn
            675                 680                 685

Val Thr Trp Gln Ser Gly Ala Asn His Thr Tyr Ser Ser Pro Glu Ser
            690                 695                 700

Gly Thr Gly Ile Ile Arg Val Asp Trp
705                 710

<210> SEQ ID NO 2
<211> LENGTH: 713
<212> TYPE: PRT
<213> ORGANISM: Bacillus agaradherens

<400> SEQUENCE: 2

Met Arg Lys Lys Thr Leu Lys Arg Leu Leu Thr Leu Val Val Gly Leu
1               5                   10                  15

Val Ile Leu Ser Gly Leu Ser Ile Leu Asp Phe Ser Ile Thr Ser Ala
                20                  25                  30

Ser Ala Gln Gln Ala Thr Asp Arg Ser Asn Ser Val Asn Tyr Ser Thr
            35                  40                  45

Asp Val Ile Tyr Gln Ile Val Thr Asp Arg Phe Tyr Asp Gly Asp Glu
    50                  55                  60

Ser Asn Asn Pro Ser Gly Glu Leu Tyr Ser Glu Asp Cys Lys Asn Leu
65                  70                  75                  80

Arg Lys Tyr Cys Gly Gly Asp Trp Gln Gly Ile Ile Asp Lys Ile Asp
                85                  90                  95

Asp Gly Tyr Leu Thr Asn Met Gly Val Thr Ala Leu Trp Ile Ser Pro
            100                 105                 110

Pro Val Glu Asn Ile Phe Glu Thr Ile Asp Asp Glu Phe Gly Thr Thr
            115                 120                 125

Ser Tyr His Gly Tyr Trp Ala Arg Asp Tyr Lys Lys Thr Asn Pro Phe
    130                 135                 140

Phe Gly Ser Thr Glu Asp Phe Glu Arg Leu Ile Glu Thr Ala His Ser
145                 150                 155                 160

His Asp Ile Lys Ile Val Ile Asp Leu Ala Pro Asn His Thr Ser Pro
                165                 170                 175

Ala Asp Phe Asp Asn Pro Asp Tyr Ala Glu Asn Gly Val Leu Tyr Asp
            180                 185                 190

Asp Gly Asn Tyr Leu Gly Ser Tyr Ser Asp Asp Ser Asp Leu Phe Leu
        195                 200                 205

Tyr Asn Gly Gly Thr Asp Phe Ser Asn Tyr Glu Asp Glu Ile Tyr Arg
    210                 215                 220

Asn Leu Phe Asp Leu Ala Ser Phe Asn His Ile Asn Ser Glu Leu Asn
225                 230                 235                 240

Asn Tyr Leu Glu Asp Ala Val Lys Lys Trp Leu Asp Leu Gly Ile Asp
                245                 250                 255

Gly Ile Arg Ile Asp Ala Val Ala His Met Pro Pro Gly Trp Lys Lys
            260                 265                 270

Ala Tyr Met Asp Thr Ile Tyr Asp His Arg Ala Val Phe Thr Phe Gly
            275                 280                 285
```

```
Glu Trp Phe Thr Gly Pro Ser Gly Asn Glu Asp Tyr Thr Lys Phe Ala
    290                 295                 300

Asn Asn Ser Gly Met Ser Val Leu Asp Phe Arg Phe Ala Gln Thr Thr
305                 310                 315                 320

Arg Asn Val Ile Gly Asn Asn Gly Thr Met Tyr Asp Ile Glu Lys
                325                 330                 335

Met Leu Thr Asp Thr Glu Asn Asp Tyr Asp Arg Pro Gln Asp Gln Val
                340                 345                 350

Thr Phe Leu Asp Asn His Asp Met Ser Arg Phe Thr Asn Gly Gly Glu
            355                 360                 365

Ser Thr Arg Thr Thr Asp Ile Gly Leu Ala Leu Met Leu Thr Ser Arg
        370                 375                 380

Gly Val Pro Thr Ile Tyr Tyr Gly Thr Glu Gln Tyr Met Lys Gly Asp
385                 390                 395                 400

Gly Asp Pro Gly Ser Arg Gly Met Met Ala Ser Phe Asp Glu Asn Thr
                405                 410                 415

Asp Ala Tyr Lys Leu Ile Gln Lys Leu Ala Pro Leu Arg Lys Ser Asn
                420                 425                 430

Pro Ala Tyr Gly Tyr Gly Thr Thr Glu Arg Trp Ile Asn Asp Asp
                435                 440                 445

Val Leu Ile Tyr Glu Arg His Phe Gly Glu Asn Tyr Ala Leu Ile Ala
    450                 455                 460

Ile Asn Arg Ser Leu Asn Thr Ser Tyr Asn Ile Gln Gly Leu Gln Thr
465                 470                 475                 480

Glu Met Pro Ser Asn Ser Tyr Asp Asp Val Leu Asp Gly Leu Leu Asp
                485                 490                 495

Gly Gln Ser Ile Val Val Asp Asn Lys Gly Gly Val Asn Glu Phe Gln
                500                 505                 510

Met Ser Pro Gly Glu Val Ser Val Trp Glu Phe Glu Ala Glu Asn Val
                515                 520                 525

Asp Lys Pro Ser Ile Gly Gln Val Gly Pro Ile Ile Gly Glu Ala Gly
    530                 535                 540

Arg Thr Val Thr Ile Ser Gly Glu Gly Phe Gly Ser Ser Gln Gly Thr
545                 550                 555                 560

Val His Phe Gly Ser Thr Ser Ala Glu Ile Leu Ser Trp Asn Asp Thr
                565                 570                 575

Ile Ile Thr Leu Thr Val Pro Asn Asn Glu Ala Gly Tyr His Asp Ile
                580                 585                 590

Thr Val Val Thr Glu Asp Glu Gln Val Ser Asn Ala Tyr Glu Phe Glu
            595                 600                 605

Val Leu Thr Ala Asp Gln Val Thr Val Arg Phe Ile Ile Asp Asn Ala
    610                 615                 620

Glu Thr Lys Leu Gly Glu Asn Val Phe Leu Val Gly Asn Val His Glu
625                 630                 635                 640

Leu Gly Asn Trp Asp Pro Glu Gln Ser Val Gly Arg Phe Phe Asn Gln
                645                 650                 655

Ile Val Tyr Gln Tyr Pro Thr Trp Tyr Tyr Asp Val Asn Val Pro Ala
                660                 665                 670

Asn Thr Asp Leu Glu Phe Lys Phe Ile Lys Ile Asp Gln Asp Asn Asn
                675                 680                 685

Val Ile Trp Gln Ser Gly Ala Asn Gln Thr Tyr Ser Ser Pro Glu Ser
    690                 695                 700

Gly Thr Gly Ile Ile Arg Val Asp Trp
```

<210> SEQ ID NO 3
<211> LENGTH: 714
<212> TYPE: PRT
<213> ORGANISM: Panibacillus macerans

<400> SEQUENCE: 3

Met Lys Ser Arg Tyr Lys Arg Leu Thr Ser Leu Ala Leu Ser Leu Ser
1               5                   10                  15

Met Ala Leu Gly Ile Ser Leu Pro Ala Trp Ala Ser Pro Asp Thr Ser
            20                  25                  30

Val Asp Asn Lys Val Asn Phe Ser Thr Asp Val Ile Tyr Gln Ile Val
        35                  40                  45

Thr Asp Arg Phe Ala Asp Gly Asp Arg Thr Asn Asn Pro Ala Gly Asp
    50                  55                  60

Ala Phe Ser Gly Asp Arg Ser Asn Leu Lys Leu Tyr Phe Gly Gly Asp
65                  70                  75                  80

Trp Gln Gly Ile Ile Asp Lys Ile Asn Asp Gly Tyr Leu Thr Gly Met
                85                  90                  95

Gly Val Thr Ala Leu Trp Ile Ser Gln Pro Val Glu Asn Ile Thr Ser
            100                 105                 110

Val Ile Lys Tyr Ser Gly Val Asn Asn Thr Ser Tyr His Gly Tyr Trp
        115                 120                 125

Ala Arg Asp Phe Lys Gln Thr Asn Asp Ala Phe Gly Asp Phe Ala Asp
    130                 135                 140

Phe Gln Asn Leu Ile Asp Thr Ala His Ala His Asn Ile Lys Val Val
145                 150                 155                 160

Ile Asp Phe Ala Pro Asn His Thr Ser Pro Ala Asp Arg Asp Asn Pro
                165                 170                 175

Gly Phe Ala Glu Asn Gly Gly Met Tyr Asp Asn Gly Ser Leu Leu Gly
            180                 185                 190

Ala Tyr Ser Asn Asp Thr Ala Gly Leu Phe His His Asn Gly Gly Thr
        195                 200                 205

Asp Phe Ser Thr Ile Glu Asp Gly Ile Tyr Lys Asn Leu Tyr Asp Leu
    210                 215                 220

Ala Asp Ile Asn His Asn Asn Asn Ala Met Asp Ala Tyr Phe Lys Ser
225                 230                 235                 240

Ala Ile Asp Leu Trp Leu Gly Met Gly Val Asp Gly Ile Arg Phe Asp
                245                 250                 255

Ala Val Lys His Met Pro Phe Gly Trp Gln Lys Ser Phe Val Ser Ser
            260                 265                 270

Ile Tyr Gly Gly Asp His Pro Val Phe Thr Phe Gly Glu Trp Tyr Leu
        275                 280                 285

Gly Ala Asp Gln Thr Asp Gly Asp Asn Ile Lys Phe Ala Asn Glu Ser
    290                 295                 300

Gly Met Asn Leu Leu Asp Phe Glu Tyr Ala Gln Glu Val Arg Glu Val
305                 310                 315                 320

Phe Arg Asp Lys Thr Glu Thr Met Lys Asp Leu Tyr Glu Val Leu Ala
                325                 330                 335

Ser Thr Glu Ser Gln Tyr Asp Tyr Ile Asn Asn Met Val Thr Phe Ile
            340                 345                 350

Asp Asn His Asp Met Asp Arg Phe Gln Val Ala Gly Ser Gly Thr Arg
        355                 360                 365

Ala Thr Glu Gln Ala Leu Ala Leu Thr Leu Thr Ser Arg Gly Val Pro

```
                370             375             380
Ala Ile Tyr Tyr Gly Thr Glu Gln Tyr Met Thr Gly Asp Gly Asp Pro
385                 390                 395                 400

Asn Asn Arg Ala Met Met Thr Ser Phe Asn Thr Gly Thr Thr Ala Tyr
                405                 410                 415

Lys Val Ile Gln Ala Leu Ala Pro Leu Arg Lys Ser Asn Pro Ala Ile
            420                 425                 430

Ala Tyr Gly Thr Thr Glu Arg Trp Val Asn Asn Asp Val Leu Ile
        435                 440                 445

Ile Glu Arg Lys Phe Gly Ser Ser Ala Ala Leu Val Ala Ile Asn Arg
    450                 455                 460

Asn Ser Ser Ala Ala Tyr Pro Ile Ser Gly Leu Leu Ser Ser Leu Pro
465                 470                 475                 480

Ala Gly Thr Tyr Ser Asp Val Leu Asn Gly Leu Leu Asn Gly Asn Ser
                485                 490                 495

Ile Thr Val Gly Ser Gly Ala Val Thr Asn Phe Thr Leu Ala Ala
                500                 505                 510

Gly Gly Thr Ala Val Trp Gln Tyr Thr Ala Pro Glu Thr Ser Pro Ala
                515                 520                 525

Ile Gly Asn Val Gly Pro Thr Met Gly Gln Pro Gly Asn Ile Val Thr
        530                 535                 540

Ile Asp Gly Arg Gly Phe Gly Thr Ala Gly Thr Val Tyr Phe Gly
545                 550                 555                 560

Thr Thr Ala Val Thr Gly Ser Gly Ile Val Ser Trp Glu Asp Thr Gln
                565                 570                 575

Ile Lys Ala Val Ile Pro Lys Val Ala Ala Gly Lys Thr Gly Val Ser
            580                 585                 590

Val Lys Thr Ser Ser Gly Thr Ala Ser Asn Thr Phe Lys Ser Phe Asn
        595                 600                 605

Val Leu Thr Gly Asp Gln Val Thr Val Arg Phe Leu Val Asn Gln Ala
    610                 615                 620

Asn Thr Asn Tyr Gly Thr Asn Val Tyr Leu Val Gly Asn Ala Ala Glu
625                 630                 635                 640

Leu Gly Ser Trp Asp Pro Asn Lys Ala Ile Gly Pro Met Tyr Asn Gln
                645                 650                 655

Val Ile Ala Lys Tyr Pro Ser Trp Tyr Tyr Asp Val Ser Val Pro Ala
                660                 665                 670

Gly Thr Lys Leu Asp Phe Lys Phe Ile Lys Lys Gly Gly Thr Val
        675                 680                 685

Thr Trp Glu Gly Gly Gly Asn His Thr Tyr Thr Thr Pro Ala Ser Gly
690                 695                 700

Val Gly Thr Val Thr Val Asp Trp Gln Asn
705                 710

<210> SEQ ID NO 4
<211> LENGTH: 713
<212> TYPE: PRT
<213> ORGANISM: Panibacillus macerans

<400> SEQUENCE: 4

Met Lys Lys Gln Val Lys Trp Leu Thr Ser Val Ser Met Ser Val Gly
1               5                   10                  15

Ile Ala Leu Gly Ala Ala Leu Pro Val Trp Ala Ser Pro Asp Thr Ser
            20                  25                  30

Val Asn Asn Lys Leu Asn Phe Ser Thr Asp Thr Val Tyr Gln Ile Val
```

-continued

```
                35                  40                  45
Thr Asp Arg Phe Val Asp Gly Asn Ser Ala Asn Asn Pro Thr Gly Ala
 50                  55                  60
Ala Phe Ser Ser Asp His Ser Asn Leu Lys Leu Tyr Phe Gly Gly Asp
 65                  70                  75                  80
Trp Gln Gly Ile Thr Asn Lys Ile Asn Asp Gly Tyr Leu Thr Gly Met
                 85                  90                  95
Gly Ile Thr Ala Leu Trp Ile Ser Gln Pro Val Glu Asn Ile Thr Ala
                100                 105                 110
Val Ile Asn Tyr Ser Gly Val Asn Asn Thr Ala Tyr His Gly Tyr Trp
                115                 120                 125
Pro Arg Asp Phe Lys Lys Thr Asn Ala Ala Phe Gly Ser Phe Thr Asp
130                 135                 140
Phe Ser Asn Leu Ile Ala Ala His Ser His Asn Ile Lys Val Val
145                 150                 155                 160
Met Asp Phe Ala Pro Asn His Thr Asn Pro Ala Ser Ser Thr Asp Pro
                165                 170                 175
Ser Phe Ala Glu Asn Gly Ala Leu Tyr Asn Asn Gly Thr Leu Leu Gly
                180                 185                 190
Lys Tyr Ser Asn Asp Thr Ala Gly Leu Phe His His Asn Gly Gly Thr
                195                 200                 205
Asp Phe Ser Thr Thr Glu Ser Gly Ile Tyr Lys Asn Leu Tyr Asp Leu
                210                 215                 220
Ala Asp Ile Asn Gln Asn Asn Asn Thr Ile Asp Ser Tyr Leu Lys Glu
225                 230                 235                 240
Ser Ile Gln Leu Trp Leu Asn Leu Gly Val Asp Gly Ile Arg Phe Asp
                245                 250                 255
Ala Val Lys His Met Pro Gln Gly Trp Gln Lys Ser Tyr Val Ser Ser
                260                 265                 270
Ile Tyr Ser Ser Ala Asn Pro Val Phe Thr Phe Gly Glu Trp Phe Leu
                275                 280                 285
Gly Pro Asp Glu Met Thr Gln Asp Asn Ile Asn Phe Ala Asn Gln Ser
290                 295                 300
Gly Met His Leu Leu Asp Phe Ala Phe Ala Gln Glu Ile Arg Glu Val
305                 310                 315                 320
Phe Arg Asp Lys Ser Glu Thr Met Thr Asp Leu Asn Ser Val Ile Ser
                325                 330                 335
Ser Thr Gly Ser Ser Tyr Asn Tyr Ile Asn Asn Met Val Thr Phe Ile
                340                 345                 350
Asp Asn His Asp Met Asp Arg Phe Gln Gln Ala Gly Ala Ser Thr Arg
                355                 360                 365
Pro Thr Glu Gln Ala Leu Ala Val Thr Leu Thr Ser Arg Gly Val Pro
370                 375                 380
Ala Ile Tyr Tyr Gly Thr Glu Gln Tyr Met Thr Gly Asn Gly Asp Pro
385                 390                 395                 400
Asn Asn Arg Gly Met Met Thr Gly Phe Asp Thr Asn Lys Thr Ala Tyr
                405                 410                 415
Lys Val Ile Lys Ala Leu Ala Pro Leu Arg Lys Ser Asn Pro Ala Leu
                420                 425                 430
Ala Tyr Gly Ser Thr Thr Gln Arg Trp Val Asn Ser Asp Val Tyr Val
                435                 440                 445
Tyr Glu Arg Lys Phe Gly Ser Asn Val Ala Leu Val Ala Val Asn Arg
450                 455                 460
```

-continued

```
Ser Ser Thr Thr Ala Tyr Pro Ile Ser Gly Ala Leu Thr Ala Leu Pro
465                 470                 475                 480

Asn Gly Thr Tyr Thr Asp Val Leu Gly Gly Leu Leu Asn Gly Asn Ser
                485                 490                 495

Ile Thr Val Asn Gly Gly Thr Val Ser Asn Phe Thr Leu Ala Ala Gly
            500                 505                 510

Gly Thr Ala Val Trp Gln Tyr Thr Thr Thr Glu Ser Ser Pro Ile Ile
        515                 520                 525

Gly Asn Val Gly Pro Thr Met Gly Lys Pro Gly Asn Thr Ile Thr Ile
530                 535                 540

Asp Gly Arg Gly Phe Gly Thr Thr Lys Asn Lys Val Thr Phe Gly Thr
545                 550                 555                 560

Thr Ala Val Thr Gly Ala Asn Ile Val Ser Trp Glu Asp Thr Glu Ile
                565                 570                 575

Lys Val Lys Val Pro Asn Val Ala Ala Gly Asn Thr Ala Val Thr Val
            580                 585                 590

Thr Asn Ala Ala Gly Thr Thr Ser Ala Ala Phe Asn Asn Phe Asn Val
        595                 600                 605

Leu Thr Ala Asp Gln Val Thr Val Arg Phe Lys Val Asn Asn Ala Thr
610                 615                 620

Thr Ala Leu Gly Gln Asn Val Tyr Leu Thr Gly Asn Val Ala Glu Leu
625                 630                 635                 640

Gly Asn Trp Thr Ala Ala Asn Ala Ile Gly Pro Met Tyr Asn Gln Val
                645                 650                 655

Glu Ala Ser Tyr Pro Thr Trp Tyr Phe Asp Val Ser Val Pro Ala Asn
            660                 665                 670

Thr Ala Leu Gln Phe Lys Phe Ile Lys Val Asn Gly Ser Thr Val Thr
        675                 680                 685

Trp Glu Gly Gly Asn Asn His Thr Phe Thr Ser Pro Ser Ser Gly Val
690                 695                 700

Ala Thr Val Thr Val Asp Trp Gln Asn
705                 710

<210> SEQ ID NO 5
<211> LENGTH: 683
<212> TYPE: PRT
<213> ORGANISM: Thermoanaerobacterium thermosulfurigenes

<400> SEQUENCE: 5

Ala Ser Asp Thr Ala Val Ser Asn Val Val Asn Tyr Ser Thr Asp Val
1               5                   10                  15

Ile Tyr Gln Ile Val Thr Asp Arg Phe Val Asp Gly Asn Thr Ser Asn
                20                  25                  30

Asn Pro Thr Gly Asp Leu Tyr Asp Pro Thr His Thr Ser Leu Lys Lys
            35                  40                  45

Tyr Phe Gly Gly Asp Trp Gln Gly Ile Ile Asn Lys Ile Asn Asp Gly
        50                  55                  60

Tyr Leu Thr Gly Met Gly Val Thr Ala Ile Trp Ile Ser Gln Pro Val
65                  70                  75                  80

Glu Asn Ile Tyr Ala Val Leu Pro Asp Ser Thr Phe Gly Gly Ser Thr
                85                  90                  95

Ser Tyr His Gly Tyr Trp Ala Arg Asp Phe Lys Arg Thr Asn Pro Tyr
            100                 105                 110

Phe Gly Ser Phe Thr Asp Phe Gln Asn Leu Ile Asn Thr Ala His Ala
        115                 120                 125
```

-continued

His Asn Ile Lys Val Ile Ile Asp Phe Ala Pro Asn His Thr Ser Pro
            130                 135                 140

Ala Ser Glu Thr Asp Pro Thr Tyr Ala Glu Asn Gly Arg Leu Tyr Asp
145                 150                 155                 160

Asn Gly Thr Leu Leu Gly Gly Tyr Thr Asn Asp Thr Asn Gly Tyr Phe
                165                 170                 175

His His Tyr Gly Gly Thr Asp Phe Ser Ser Tyr Glu Asp Gly Ile Tyr
            180                 185                 190

Arg Asn Leu Phe Asp Leu Ala Asp Leu Asn Gln Gln Asn Ser Thr Ile
                195                 200                 205

Asp Ser Tyr Leu Lys Ser Ala Ile Lys Val Trp Leu Asp Met Gly Ile
210                 215                 220

Asp Gly Ile Arg Leu Asp Ala Val Lys His Met Pro Phe Gly Trp Gln
225                 230                 235                 240

Lys Asn Phe Met Asp Ser Ile Leu Ser Tyr Arg Pro Val Phe Thr Phe
                245                 250                 255

Gly Glu Trp Phe Leu Gly Thr Asn Glu Ile Asp Val Asn Asn Thr Tyr
            260                 265                 270

Phe Ala Asn Glu Ser Gly Met Ser Leu Leu Asp Phe Arg Phe Ser Gln
            275                 280                 285

Lys Val Arg Gln Val Phe Arg Asp Asn Thr Asp Thr Met Tyr Gly Leu
290                 295                 300

Asp Ser Met Ile Gln Ser Thr Ala Ser Asp Tyr Asn Phe Ile Asn Asp
305                 310                 315                 320

Met Val Thr Phe Ile Asp Asn His Asp Met Asp Arg Phe Tyr Asn Gly
                325                 330                 335

Gly Ser Thr Arg Pro Val Glu Gln Ala Leu Ala Phe Thr Leu Thr Ser
            340                 345                 350

Arg Gly Val Pro Ala Ile Tyr Tyr Gly Thr Glu Gln Tyr Met Thr Gly
                355                 360                 365

Asn Gly Asp Pro Tyr Asn Arg Ala Met Met Thr Ser Phe Asn Thr Ser
            370                 375                 380

Thr Thr Ala Tyr Asn Val Ile Lys Lys Leu Ala Pro Leu Arg Lys Ser
385                 390                 395                 400

Asn Pro Ala Ile Ala Tyr Gly Thr Thr Gln Gln Arg Trp Ile Asn Asn
                405                 410                 415

Asp Val Tyr Ile Tyr Glu Arg Lys Phe Gly Asn Asn Val Ala Leu Val
                420                 425                 430

Ala Ile Asn Arg Asn Leu Ser Thr Ser Tyr Asn Ile Thr Gly Leu Tyr
                435                 440                 445

Thr Ala Leu Pro Ala Gly Thr Tyr Thr Asp Val Leu Gly Gly Leu Leu
450                 455                 460

Asn Gly Asn Ser Ile Ser Val Ala Ser Asp Gly Ser Val Thr Pro Phe
465                 470                 475                 480

Thr Leu Ser Ala Gly Glu Val Ala Val Trp Gln Tyr Val Ser Ser Ser
                485                 490                 495

Asn Ser Pro Leu Ile Gly His Val Gly Pro Thr Met Thr Lys Ala Gly
                500                 505                 510

Gln Thr Ile Thr Ile Asp Gly Arg Gly Phe Gly Thr Thr Ser Gly Gln
            515                 520                 525

Val Leu Phe Gly Ser Thr Ala Gly Thr Ile Val Ser Trp Asp Asp Thr
530                 535                 540

Glu Val Lys Val Lys Val Pro Ser Val Thr Pro Gly Lys Tyr Asn Ile
545                 550                 555                 560

```
Ser Leu Lys Thr Ser Ser Gly Ala Thr Ser Asn Thr Tyr Asn Asn Ile
                565                 570                 575

Asn Ile Leu Thr Gly Asn Gln Ile Cys Val Arg Phe Val Val Asn Asn
                580                 585                 590

Ala Ser Thr Val Tyr Gly Glu Asn Val Tyr Leu Thr Gly Asn Val Ala
                595                 600                 605

Glu Leu Gly Asn Trp Asp Thr Ser Lys Ala Ile Gly Pro Met Phe Asn
            610                 615                 620

Gln Val Val Tyr Gln Tyr Pro Thr Trp Tyr Tyr Asp Val Ser Val Pro
625                 630                 635                 640

Ala Gly Thr Thr Ile Gln Phe Lys Phe Ile Lys Lys Asn Gly Asn Thr
                645                 650                 655

Ile Thr Trp Glu Gly Gly Ser Asn His Thr Tyr Thr Val Pro Ser Ser
            660                 665                 670

Ser Thr Gly Thr Val Ile Val Asn Trp Gln Gln
            675                 680

<210> SEQ ID NO 6
<211> LENGTH: 683
<212> TYPE: PRT
<213> ORGANISM: Thermoanaerobacter species

<400> SEQUENCE: 6

Ala Pro Asp Thr Ser Val Ser Asn Val Asn Tyr Ser Thr Asp Val
1               5                   10                  15

Ile Tyr Gln Ile Val Thr Asp Arg Phe Leu Asp Gly Asn Pro Ser Asn
                20                  25                  30

Asn Pro Thr Gly Asp Leu Tyr Asp Pro Thr His Thr Ser Leu Lys Lys
            35                  40                  45

Tyr Phe Gly Gly Asp Trp Gln Gly Ile Ile Asn Lys Ile Asn Asp Gly
    50                  55                  60

Tyr Leu Thr Gly Met Gly Ile Thr Ala Ile Trp Ile Ser Gln Pro Val
65                  70                  75                  80

Glu Asn Ile Tyr Ala Val Leu Pro Asp Ser Thr Phe Gly Gly Ser Thr
                85                  90                  95

Ser Tyr His Gly Tyr Trp Ala Arg Asp Phe Lys Lys Thr Asn Pro Phe
            100                 105                 110

Phe Gly Ser Phe Thr Asp Phe Gln Asn Leu Ile Ala Thr Ala His Ala
        115                 120                 125

His Asn Ile Lys Val Ile Ile Asp Phe Ala Pro Asn His Thr Ser Pro
    130                 135                 140

Ala Ser Glu Thr Asp Pro Thr Tyr Gly Glu Asn Gly Arg Leu Tyr Asp
145                 150                 155                 160

Asn Gly Val Leu Leu Gly Gly Tyr Thr Asn Asp Thr Asn Gly Tyr Phe
                165                 170                 175

His His Tyr Gly Gly Thr Asn Phe Ser Ser Tyr Glu Asp Gly Ile Tyr
            180                 185                 190

Arg Asn Leu Phe Asp Leu Ala Asp Leu Asp Gln Gln Asn Ser Thr Ile
        195                 200                 205

Asp Ser Tyr Leu Lys Ala Ala Ile Lys Leu Trp Leu Asp Met Gly Ile
    210                 215                 220

Asp Gly Ile Arg Met Asp Ala Val Lys His Met Ala Phe Gly Trp Gln
225                 230                 235                 240

Lys Asn Phe Met Asp Ser Ile Leu Ser Tyr Arg Pro Val Phe Thr Phe
                245                 250                 255
```

```
Gly Glu Trp Tyr Leu Gly Thr Asn Glu Val Asp Pro Asn Asn Thr Tyr
            260                 265                 270

Phe Ala Asn Glu Ser Gly Met Ser Leu Leu Asp Phe Arg Phe Ala Gln
            275                 280                 285

Lys Val Arg Gln Val Phe Arg Asp Asn Thr Asp Thr Met Tyr Gly Leu
290                 295                 300

Asp Ser Met Ile Gln Ser Thr Ala Ala Asp Tyr Asn Phe Ile Asn Asp
305                 310                 315                 320

Met Val Thr Phe Ile Asp Asn His Asp Met Asp Arg Phe Tyr Thr Gly
                325                 330                 335

Gly Ser Thr Arg Pro Val Glu Gln Ala Leu Ala Phe Thr Leu Thr Ser
            340                 345                 350

Arg Gly Val Pro Ala Ile Tyr Tyr Gly Thr Glu Gln Tyr Met Thr Gly
            355                 360                 365

Asn Gly Asp Pro Tyr Asn Arg Ala Met Met Thr Ser Phe Asp Thr Thr
370                 375                 380

Thr Thr Ala Tyr Asn Val Ile Lys Lys Leu Ala Pro Leu Arg Lys Ser
385                 390                 395                 400

Asn Pro Ala Ile Ala Tyr Gly Thr Gln Lys Gln Arg Trp Ile Asn Asn
                405                 410                 415

Asp Val Tyr Ile Tyr Glu Arg Gln Phe Gly Asn Asn Val Ala Leu Val
            420                 425                 430

Ala Ile Asn Arg Asn Leu Ser Thr Ser Tyr Tyr Ile Thr Gly Leu Tyr
            435                 440                 445

Thr Ala Leu Pro Ala Gly Thr Tyr Ser Asp Met Leu Gly Gly Leu Leu
450                 455                 460

Asn Gly Ser Ser Ile Thr Val Ser Ser Asn Gly Ser Val Thr Pro Phe
465                 470                 475                 480

Thr Leu Ala Pro Gly Glu Val Ala Val Trp Gln Tyr Val Ser Thr Thr
                485                 490                 495

Asn Pro Pro Leu Ile Gly His Val Gly Pro Thr Met Thr Lys Ala Gly
            500                 505                 510

Gln Thr Ile Thr Ile Asp Gly Arg Gly Phe Gly Thr Thr Ala Gly Gln
            515                 520                 525

Val Leu Phe Gly Thr Thr Pro Ala Thr Ile Val Ser Trp Glu Asp Thr
530                 535                 540

Glu Val Lys Val Lys Val Pro Ala Leu Thr Pro Gly Lys Tyr Asn Ile
545                 550                 555                 560

Thr Leu Lys Thr Ala Ser Gly Val Thr Ser Asn Ser Tyr Asn Asn Ile
                565                 570                 575

Asn Val Leu Thr Gly Asn Gln Val Cys Val Arg Phe Val Val Asn Asn
            580                 585                 590

Ala Thr Thr Val Trp Gly Glu Asn Val Tyr Leu Thr Gly Asn Val Ala
            595                 600                 605

Glu Leu Gly Asn Trp Asp Thr Ser Lys Ala Ile Gly Pro Met Phe Asn
610                 615                 620

Gln Val Val Tyr Gln Tyr Pro Thr Trp Tyr Tyr Asp Val Ser Val Pro
625                 630                 635                 640

Ala Gly Thr Thr Ile Glu Phe Lys Phe Ile Lys Lys Asn Gly Ser Thr
                645                 650                 655

Val Thr Trp Glu Gly Gly Tyr Asn His Val Tyr Thr Thr Pro Thr Ser
            660                 665                 670

Gly Thr Ala Thr Val Ile Val Asp Trp Gln Pro
```

-continued

```
                675                 680

<210> SEQ ID NO 7
<211> LENGTH: 718
<212> TYPE: PRT
<213> ORGANISM: Bacillus circulans

<400> SEQUENCE: 7

Met Phe Gln Met Ala Lys Arg Ala Phe Leu Ser Thr Thr Leu Thr Leu
1               5                   10                  15

Gly Leu Leu Ala Gly Ser Ala Leu Pro Phe Leu Pro Ala Ser Ala Val
            20                  25                  30

Tyr Ala Asp Pro Asp Thr Ala Val Thr Asn Lys Gln Ser Phe Ser Thr
        35                  40                  45

Asp Val Ile Tyr Gln Val Phe Thr Asp Arg Phe Leu Asp Gly Asn Pro
    50                  55                  60

Ser Asn Asn Pro Thr Gly Ala Ala Tyr Asp Ala Thr Cys Ser Asn Leu
65                  70                  75                  80

Lys Leu Tyr Cys Gly Gly Asp Trp Gln Gly Leu Ile Asn Lys Ile Asn
                85                  90                  95

Asp Asn Tyr Phe Ser Asp Leu Gly Val Thr Ala Leu Trp Ile Ser Gln
            100                 105                 110

Pro Val Glu Asn Ile Phe Ala Thr Ile Asn Tyr Ser Gly Val Thr Asn
        115                 120                 125

Thr Ala Tyr His Gly Tyr Trp Ala Arg Asp Phe Lys Lys Thr Asn Pro
    130                 135                 140

Tyr Phe Gly Thr Met Ala Asp Phe Gln Asn Leu Ile Thr Thr Ala His
145                 150                 155                 160

Ala Lys Gly Ile Lys Ile Val Ile Asp Phe Ala Pro Asn His Thr Ser
                165                 170                 175

Pro Ala Met Glu Thr Asp Thr Ser Phe Ala Glu Asn Gly Arg Leu Tyr
            180                 185                 190

Asp Asn Gly Thr Leu Val Gly Gly Tyr Thr Asn Asp Thr Asn Gly Tyr
        195                 200                 205

Phe His His Asn Gly Gly Ser Asp Phe Ser Ser Leu Glu Asn Gly Ile
    210                 215                 220

Tyr Lys Asn Leu Tyr Asp Leu Ala Asp Phe Asn His Asn Asn Ala Thr
225                 230                 235                 240

Ile Asp Lys Tyr Phe Lys Asp Ala Ile Lys Leu Trp Leu Asp Met Gly
                245                 250                 255

Val Asp Gly Ile Arg Val Asp Ala Val Lys His Met Pro Leu Gly Trp
            260                 265                 270

Gln Lys Ser Trp Met Ser Ser Ile Tyr Ala His Lys Pro Val Phe Thr
        275                 280                 285

Phe Gly Glu Trp Phe Leu Gly Ser Ala Ala Ser Asp Ala Asp Asn Thr
    290                 295                 300

Asp Phe Ala Asn Lys Ser Gly Met Ser Leu Leu Asp Phe Arg Phe Asn
305                 310                 315                 320

Ser Ala Val Arg Asn Val Phe Arg Asp Asn Thr Ser Asn Met Tyr Ala
                325                 330                 335

Leu Asp Ser Met Ile Asn Ser Thr Ala Thr Asp Tyr Asn Gln Val Asn
            340                 345                 350

Asp Gln Val Thr Phe Ile Asp Asn His Asp Met Asp Arg Phe Lys Thr
        355                 360                 365

Ser Ala Val Asn Asn Arg Arg Leu Glu Gln Ala Leu Ala Phe Thr Leu
```

```
                370              375             380
Thr Ser Arg Gly Val Pro Ala Ile Tyr Tyr Gly Thr Glu Gln Tyr Leu
385                 390                 395                 400

Thr Gly Asn Gly Asp Pro Asp Asn Arg Ala Lys Met Pro Ser Phe Ser
                405                 410                 415

Lys Ser Thr Thr Ala Phe Asn Val Ile Ser Lys Leu Ala Pro Leu Arg
            420                 425                 430

Lys Ser Asn Pro Ala Ile Ala Tyr Gly Ser Thr Gln Gln Arg Trp Ile
                435                 440                 445

Asn Asn Asp Val Tyr Val Tyr Glu Arg Lys Phe Gly Lys Ser Val Ala
            450                 455                 460

Val Val Ala Val Asn Arg Asn Leu Ser Thr Ser Ala Ser Ile Thr Gly
465                 470                 475                 480

Leu Ser Thr Ser Leu Pro Thr Gly Ser Tyr Thr Asp Val Leu Gly Gly
                485                 490                 495

Val Leu Asn Gly Asn Asn Ile Thr Ser Thr Asn Gly Ser Ile Asn Asn
                500                 505                 510

Phe Thr Leu Ala Ala Gly Ala Thr Ala Val Trp Gln Tyr Thr Thr Ala
            515                 520                 525

Glu Thr Thr Pro Thr Ile Gly His Val Gly Pro Val Met Gly Lys Pro
            530                 535                 540

Gly Asn Val Val Thr Ile Asp Gly Arg Gly Phe Gly Ser Thr Lys Gly
545                 550                 555                 560

Thr Val Tyr Phe Gly Thr Thr Ala Val Thr Gly Ala Ala Ile Thr Ser
                565                 570                 575

Trp Glu Asp Thr Gln Ile Lys Val Thr Ile Pro Ser Val Ala Ala Gly
            580                 585                 590

Asn Tyr Ala Val Lys Val Ala Ala Ser Gly Val Asn Ser Asn Ala Tyr
            595                 600                 605

Asn Asn Phe Thr Ile Leu Thr Gly Asp Gln Val Thr Val Arg Phe Val
            610                 615                 620

Val Asn Asn Ala Ser Thr Thr Leu Gly Gln Asn Leu Tyr Leu Thr Gly
625                 630                 635                 640

Asn Val Ala Glu Leu Gly Asn Trp Ser Thr Gly Ser Thr Ala Ile Gly
                645                 650                 655

Pro Ala Phe Asn Gln Val Ile His Gln Tyr Pro Thr Trp Tyr Tyr Asp
                660                 665                 670

Val Ser Val Pro Ala Gly Lys Gln Leu Glu Phe Lys Phe Phe Lys Lys
            675                 680                 685

Asn Gly Ser Thr Ile Thr Trp Glu Ser Gly Ser Asn His Thr Phe Thr
            690                 695                 700

Thr Pro Ala Ser Gly Thr Ala Thr Val Thr Val Asn Trp Gln
705                 710                 715

<210> SEQ ID NO 8
<211> LENGTH: 718
<212> TYPE: PRT
<213> ORGANISM: Bacillus species

<400> SEQUENCE: 8

Met Phe Gln Met Ala Lys Arg Val Leu Leu Ser Thr Thr Leu Thr Phe
1               5                   10                  15

Ser Leu Leu Ala Gly Ser Ala Leu Pro Phe Leu Pro Ala Ser Ala Ile
                20                  25                  30

Tyr Ala Asp Ala Asp Thr Ala Val Thr Asn Lys Gln Asn Phe Ser Thr
```

```
                    35                  40                  45
Asp Val Ile Tyr Gln Val Phe Thr Asp Arg Phe Leu Asp Gly Asn Pro
 50                  55                  60

Ser Asn Asn Pro Thr Gly Ala Ala Phe Asp Gly Thr Cys Ser Asn Leu
 65                  70                  75                  80

Lys Leu Tyr Cys Gly Gly Asp Trp Gln Gly Leu Val Asn Lys Ile Asn
                     85                  90                  95

Asp Asn Tyr Phe Ser Asp Leu Gly Val Thr Ala Leu Trp Ile Ser Gln
                100                 105                 110

Pro Val Glu Asn Ile Phe Ala Thr Ile Asn Tyr Ser Gly Val Thr Asn
                115                 120                 125

Thr Ala Tyr His Gly Tyr Trp Ala Arg Asp Phe Lys Lys Thr Asn Pro
            130                 135                 140

Tyr Phe Gly Thr Met Thr Asp Phe Gln Asn Leu Val Thr Thr Ala His
145                 150                 155                 160

Ala Lys Gly Ile Lys Ile Ile Ile Asp Phe Ala Pro Asn His Thr Ser
                165                 170                 175

Pro Ala Met Glu Thr Asp Thr Ser Phe Ala Glu Asn Gly Lys Leu Tyr
            180                 185                 190

Asp Asn Gly Asn Leu Val Gly Gly Tyr Thr Asn Asp Thr Asn Gly Tyr
            195                 200                 205

Phe His His Asn Gly Gly Ser Asp Phe Ser Thr Leu Glu Asn Gly Ile
            210                 215                 220

Tyr Lys Asn Leu Tyr Asp Leu Ala Asp Leu Asn His Asn Asn Ser Thr
225                 230                 235                 240

Ile Asp Thr Tyr Phe Lys Asp Ala Ile Lys Leu Trp Leu Asp Met Gly
                245                 250                 255

Val Asp Gly Ile Arg Val Asp Ala Val Lys His Met Pro Gln Gly Trp
            260                 265                 270

Gln Lys Asn Trp Met Ser Ser Ile Tyr Ala His Lys Pro Val Phe Thr
            275                 280                 285

Phe Gly Glu Trp Phe Leu Gly Ser Ala Ala Pro Asp Ala Asp Asn Thr
            290                 295                 300

Asp Phe Ala Asn Glu Ser Gly Met Ser Leu Leu Asp Phe Arg Phe Asn
305                 310                 315                 320

Ser Ala Val Arg Asn Val Phe Arg Asp Asn Thr Ser Asn Met Tyr Ala
                325                 330                 335

Leu Asp Ser Met Leu Thr Ala Thr Ala Ala Asp Tyr Asn Gln Val Asn
            340                 345                 350

Asp Gln Val Thr Phe Ile Asp Asn His Asp Met Asp Arg Phe Lys Thr
            355                 360                 365

Ser Ala Val Asn Asn Arg Arg Leu Glu Gln Ala Leu Ala Phe Thr Leu
            370                 375                 380

Thr Ser Arg Gly Val Pro Ala Ile Tyr Tyr Gly Thr Glu Gln Tyr Leu
385                 390                 395                 400

Thr Gly Asn Gly Asp Pro Asp Asn Arg Gly Lys Met Pro Ser Phe Ser
                405                 410                 415

Lys Ser Thr Thr Ala Phe Asn Val Ile Ser Lys Leu Ala Pro Leu Arg
                420                 425                 430

Lys Ser Asn Pro Ala Ile Ala Tyr Gly Ser Thr Gln Gln Arg Trp Ile
            435                 440                 445

Asn Asn Asp Val Tyr Ile Tyr Glu Arg Lys Phe Gly Lys Ser Val Ala
            450                 455                 460
```

```
Val Val Ala Val Asn Arg Asn Leu Thr Thr Pro Thr Ser Ile Thr Asn
465                 470                 475                 480

Leu Asn Thr Ser Leu Pro Ser Gly Thr Tyr Thr Asp Val Leu Gly Gly
                485                 490                 495

Val Leu Asn Gly Asn Asn Ile Thr Ser Ser Gly Gly Asn Ile Ser Ser
            500                 505                 510

Phe Thr Leu Ala Ala Gly Ala Thr Ala Val Trp Gln Tyr Thr Ala Ser
            515                 520                 525

Glu Thr Thr Pro Thr Ile Gly His Val Gly Pro Val Met Gly Lys Pro
        530                 535                 540

Gly Asn Val Val Thr Ile Asp Gly Arg Gly Phe Gly Ser Ala Lys Gly
545                 550                 555                 560

Thr Val Tyr Phe Gly Thr Thr Ala Val Thr Gly Ser Ala Ile Thr Ser
                565                 570                 575

Trp Glu Asp Thr Gln Ile Lys Val Thr Ile Pro Pro Val Ala Gly Gly
            580                 585                 590

Asp Tyr Ala Val Lys Val Ala Ala Asn Gly Val Asn Ser Asn Ala Tyr
            595                 600                 605

Asn Asp Phe Thr Ile Leu Ser Gly Asp Gln Val Ser Val Arg Phe Val
610                 615                 620

Ile Asn Asn Ala Thr Thr Ala Leu Gly Glu Asn Ile Tyr Leu Thr Gly
625                 630                 635                 640

Asn Val Ser Glu Leu Gly Asn Trp Thr Thr Gly Ala Ala Ser Ile Gly
                645                 650                 655

Pro Ala Phe Asn Gln Val Ile His Ala Tyr Pro Thr Trp Tyr Tyr Asp
                660                 665                 670

Val Ser Val Pro Ala Gly Lys Gln Leu Glu Phe Lys Phe Phe Lys Lys
            675                 680                 685

Asn Gly Ala Thr Ile Thr Trp Glu Gly Gly Ser Asn His Thr Phe Thr
            690                 695                 700

Thr Pro Thr Ser Gly Thr Ala Thr Val Thr Ile Asn Trp Gln
705                 710                 715

<210> SEQ ID NO 9
<211> LENGTH: 713
<212> TYPE: PRT
<213> ORGANISM: Bacillus sp. 1011

<400> SEQUENCE: 9

Met Lys Arg Phe Met Lys Leu Thr Ala Val Trp Thr Leu Trp Leu Ser
1               5                   10                  15

Leu Thr Leu Gly Leu Leu Ser Pro Val His Ala Ala Pro Asp Thr Ser
                20                  25                  30

Val Ser Asn Lys Gln Asn Phe Ser Thr Asp Val Ile Tyr Gln Ile Phe
            35                  40                  45

Thr Asp Arg Phe Ser Asp Gly Asn Pro Ala Asn Pro Thr Gly Ala
        50                  55                  60

Ala Phe Asp Gly Ser Cys Thr Asn Leu Arg Leu Tyr Cys Gly Gly Asp
65                  70                  75                  80

Trp Gln Gly Ile Ile Asn Lys Ile Asn Asp Gly Tyr Leu Thr Gly Met
                85                  90                  95

Gly Ile Thr Ala Ile Trp Ile Ser Gln Pro Val Glu Asn Ile Tyr Ser
            100                 105                 110

Val Ile Asn Tyr Ser Gly Val Asn Asn Thr Ala Tyr His Gly Tyr Trp
        115                 120                 125
```

-continued

Ala Arg Asp Phe Lys Lys Thr Asn Pro Ala Tyr Gly Thr Met Gln Asp
130                 135                 140

Phe Lys Asn Leu Ile Asp Thr Ala His Ala His Asn Ile Lys Val Ile
145                 150                 155                 160

Ile Asp Phe Ala Pro Asn His Thr Ser Pro Ala Ser Ser Asp Asp Pro
            165                 170                 175

Ser Phe Ala Glu Asn Gly Arg Leu Tyr Asp Asn Gly Asn Leu Leu Gly
            180                 185                 190

Gly Tyr Thr Asn Asp Thr Gln Asn Leu Phe His His Tyr Gly Gly Thr
        195                 200                 205

Asp Phe Ser Thr Ile Glu Asn Gly Ile Tyr Lys Asn Leu Tyr Asp Leu
210                 215                 220

Ala Asp Leu Asn His Asn Asn Ser Ser Val Asp Val Tyr Leu Lys Asp
225                 230                 235                 240

Ala Ile Lys Met Trp Leu Asp Leu Gly Val Asp Gly Ile Arg Val Asp
                245                 250                 255

Ala Val Lys His Met Pro Phe Gly Trp Gln Lys Ser Phe Met Ala Thr
            260                 265                 270

Ile Asn Asn Tyr Lys Pro Val Phe Thr Phe Gly Glu Trp Phe Leu Gly
            275                 280                 285

Val Asn Glu Ile Ser Pro Glu Tyr His Gln Phe Ala Asn Glu Ser Gly
290                 295                 300

Met Ser Leu Leu Asp Phe Arg Phe Ala Gln Lys Ala Arg Gln Val Phe
305                 310                 315                 320

Arg Asp Asn Thr Asp Asn Met Tyr Gly Leu Lys Ala Met Leu Glu Gly
                325                 330                 335

Ser Glu Val Asp Tyr Ala Gln Val Asn Asp Gln Val Thr Phe Ile Asp
            340                 345                 350

Asn His Asp Met Glu Arg Phe His Thr Ser Asn Gly Asp Arg Arg Lys
            355                 360                 365

Leu Glu Gln Ala Leu Ala Phe Thr Leu Thr Ser Arg Gly Val Pro Ala
370                 375                 380

Ile Tyr Tyr Gly Ser Glu Gln Tyr Met Ser Gly Gly Asn Asp Pro Asp
385                 390                 395                 400

Asn Arg Ala Arg Leu Pro Ser Phe Ser Thr Thr Thr Ala Tyr Gln
                405                 410                 415

Val Ile Gln Lys Leu Ala Pro Leu Arg Lys Ser Asn Pro Ala Ile Ala
                420                 425                 430

Tyr Gly Ser Thr His Glu Arg Trp Ile Asn Asn Asp Val Ile Ile Tyr
            435                 440                 445

Glu Arg Lys Phe Gly Asn Asn Val Ala Val Val Ala Ile Asn Arg Asn
450                 455                 460

Met Asn Thr Pro Ala Ser Ile Thr Gly Leu Val Thr Ser Leu Arg Arg
465                 470                 475                 480

Ala Ser Tyr Asn Asp Val Leu Gly Gly Ile Leu Asn Gly Asn Thr Leu
                485                 490                 495

Thr Val Gly Ala Gly Gly Ala Ala Ser Asn Phe Thr Leu Ala Pro Gly
            500                 505                 510

Gly Thr Ala Val Trp Gln Tyr Thr Thr Asp Ala Thr Thr Pro Ile Ile
            515                 520                 525

Gly Asn Val Gly Pro Met Met Ala Lys Pro Gly Val Thr Ile Thr Ile
530                 535                 540

Asp Gly Arg Gly Phe Gly Ser Gly Lys Gly Thr Val Tyr Phe Gly Thr
545                 550                 555                 560

Thr Ala Val Thr Gly Ala Asp Ile Val Ala Trp Glu Asp Thr Gln Ile
                565                 570                 575

Gln Val Lys Ile Pro Ala Val Pro Gly Gly Ile Tyr Asp Ile Arg Val
                580                 585                 590

Ala Asn Ala Ala Gly Ala Ala Ser Asn Ile Tyr Asp Asn Phe Glu Val
                595                 600                 605

Leu Thr Gly Asp Gln Val Thr Val Arg Phe Val Ile Asn Asn Ala Thr
                610                 615                 620

Thr Ala Leu Gly Gln Asn Val Phe Leu Thr Gly Asn Val Ser Glu Leu
625                 630                 635                 640

Gly Asn Trp Asp Pro Asn Asn Ala Ile Gly Pro Met Tyr Asn Gln Val
                645                 650                 655

Val Tyr Gln Tyr Pro Thr Trp Tyr Tyr Asp Val Ser Val Pro Ala Gly
                660                 665                 670

Gln Thr Ile Glu Phe Lys Phe Leu Lys Lys Gln Gly Ser Thr Val Thr
                675                 680                 685

Trp Glu Gly Gly Ala Asn Arg Thr Phe Thr Thr Pro Thr Ser Gly Thr
                690                 695                 700

Ala Thr Val Asn Val Asn Trp Gln Pro
705                 710

<210> SEQ ID NO 10
<211> LENGTH: 712
<212> TYPE: PRT
<213> ORGANISM: Bacillus species

<400> SEQUENCE: 10

Met Lys Arg Phe Met Lys Leu Thr Ala Val Trp Thr Leu Trp Leu Ser
1               5                   10                  15

Leu Thr Leu Gly Leu Leu Ser Pro Val His Ala Ala Pro Asp Thr Ser
                20                  25                  30

Val Ser Asn Lys Gln Asn Phe Ser Thr Asp Val Ile Tyr Gln Ile Phe
                35                  40                  45

Thr Asp Arg Phe Ser Asp Gly Asn Pro Ala Asn Asn Pro Thr Gly Ala
                50                  55                  60

Ala Phe Asp Gly Ser Cys Thr Asn Leu Arg Leu Tyr Cys Gly Gly Asp
65                  70                  75                  80

Trp Gln Gly Ile Ile Asn Lys Ile Asn Asp Gly Tyr Leu Thr Gly Met
                85                  90                  95

Gly Ile Thr Ala Ile Trp Ile Ser Gln Pro Val Glu Asn Ile Tyr Ser
                100                 105                 110

Val Ile Asn Tyr Ser Gly Val His Asn Thr Ala Tyr His Gly Tyr Trp
                115                 120                 125

Ala Arg Asp Phe Lys Lys Thr Asn Pro Ala Tyr Gly Thr Met Gln Asp
                130                 135                 140

Phe Lys Asn Leu Ile Asp Thr Ala His Ala His Asn Ile Lys Val Ile
145                 150                 155                 160

Ile Asp Phe Ala Pro Asn His Thr Ser Pro Ala Ser Ser Asp Asp Pro
                165                 170                 175

Ser Phe Ala Glu Asn Gly Arg Leu Tyr Asp Asn Gly Asn Leu Leu Gly
                180                 185                 190

Gly Tyr Thr Asn Asp Thr Gln Asn Leu Phe His His Tyr Gly Gly Thr
                195                 200                 205

Asp Phe Ser Thr Ile Glu Asn Gly Ile Tyr Lys Asn Leu Tyr Asp Leu
                210                 215                 220

```
Ala Asp Leu Asn His Asn Asn Ser Ser Val Asp Val Tyr Leu Lys Asp
225                 230                 235                 240

Ala Ile Lys Met Trp Leu Asp Leu Gly Val Asp Gly Ile Arg Val Asp
            245                 250                 255

Ala Val Lys His Met Pro Phe Gly Trp Gln Lys Ser Phe Met Ser Thr
        260                 265                 270

Ile Asn Asn Tyr Lys Pro Val Phe Asn Phe Gly Glu Trp Phe Leu Gly
    275                 280                 285

Val Asn Glu Ile Ser Pro Glu Tyr His Gln Phe Ala Asn Glu Ser Gly
290                 295                 300

Met Ser Leu Leu Asp Phe Pro Phe Ala Gln Lys Ala Arg Gln Val Phe
305                 310                 315                 320

Arg Asp Asn Thr Asp Asn Met Tyr Gly Leu Lys Ala Met Leu Glu Gly
            325                 330                 335

Ser Glu Val Asp Tyr Ala Gln Val Asn Asp Gln Val Thr Phe Ile Asp
        340                 345                 350

Asn His Asp Met Glu Arg Phe His Thr Ser Asn Gly Asp Arg Arg Lys
    355                 360                 365

Leu Glu Gln Ala Leu Ala Phe Thr Leu Thr Ser Arg Gly Val Pro Ala
370                 375                 380

Ile Tyr Tyr Gly Ser Glu Gln Tyr Met Ser Gly Gly Asn Asp Pro Asp
385                 390                 395                 400

Asn Arg Ala Arg Ile Pro Ser Phe Ser Thr Thr Thr Ala Tyr Gln
            405                 410                 415

Val Ile Gln Lys Leu Ala Pro Leu Arg Lys Ser Asn Pro Ala Ile Ala
            420                 425                 430

Tyr Gly Ser Thr Gln Glu Arg Trp Ile Asn Asn Asp Val Ile Ile Tyr
        435                 440                 445

Glu Arg Lys Phe Gly Asn Asn Val Ala Val Val Ala Ile Asn Arg Asn
450                 455                 460

Met Asn Thr Pro Ala Ser Ile Thr Gly Leu Val Thr Ser Leu Pro Gln
465                 470                 475                 480

Gly Ser Tyr Asn Asp Val Leu Gly Gly Ile Leu Asn Gly Asn Thr Leu
            485                 490                 495

Thr Val Gly Ala Gly Gly Ala Ala Ser Asn Phe Thr Leu Ala Pro Gly
        500                 505                 510

Gly Thr Ala Val Trp Gln Tyr Thr Thr Asp Ala Thr Ala Pro Ile Asn
    515                 520                 525

Gly Asn Val Gly Pro Met Met Ala Lys Ala Gly Val Thr Ile Thr Ile
530                 535                 540

Asp Gly Arg Ala Ser Ala Arg Gln Gly Thr Val Tyr Phe Gly Thr Thr
545                 550                 555                 560

Ala Val Thr Gly Ala Asp Ile Val Ala Trp Glu Asp Thr Gln Ile Gln
            565                 570                 575

Val Lys Ile Leu Arg Val Pro Gly Gly Ile Tyr Asp Ile Arg Val Ala
            580                 585                 590

Asn Ala Ala Gly Ala Ala Ser Asn Ile Tyr Asp Asn Phe Glu Val Leu
        595                 600                 605

Thr Gly Asp Gln Val Thr Val Arg Phe Val Ile Asn Asn Ala Thr Thr
    610                 615                 620

Ala Leu Gly Gln Asn Val Phe Leu Thr Gly Asn Val Ser Glu Leu Gly
625                 630                 635                 640

Asn Trp Asp Pro Asn Asn Ala Ile Gly Pro Met Tyr Asn Gln Val Val
```

```
                    645                 650                 655
Tyr Gln Tyr Pro Thr Trp Tyr Tyr Asp Val Ser Val Pro Ala Gly Gln
            660                 665                 670

Thr Ile Glu Phe Lys Phe Leu Lys Lys Gln Gly Ser Thr Val Thr Trp
            675                 680                 685

Glu Gly Gly Ala Asn Arg Thr Phe Thr Thr Pro Thr Ser Gly Thr Ala
            690                 695                 700

Thr Val Asn Val Asn Trp Gln Pro
705                 710

<210> SEQ ID NO 11
<211> LENGTH: 713
<212> TYPE: PRT
<213> ORGANISM: Bacillus circulans

<400> SEQUENCE: 11

Met Lys Lys Phe Leu Lys Ser Thr Ala Ala Leu Ala Leu Gly Leu Ser
1               5                   10                  15

Leu Thr Phe Gly Leu Phe Ser Pro Ala Gln Ala Ala Pro Asp Thr Ser
            20                  25                  30

Val Ser Asn Lys Gln Asn Phe Ser Thr Asp Val Ile Tyr Gln Ile Phe
        35                  40                  45

Thr Asp Arg Phe Ser Asp Gly Asn Pro Ala Asn Asn Pro Thr Gly Ala
    50                  55                  60

Ala Phe Asp Gly Thr Cys Thr Asn Leu Arg Leu Tyr Cys Gly Gly Asp
65                  70                  75                  80

Trp Gln Gly Ile Ile Asn Lys Ile Asn Asp Gly Tyr Leu Thr Gly Met
                85                  90                  95

Gly Val Thr Ala Ile Trp Ile Ser Gln Pro Val Glu Asn Ile Tyr Ser
            100                 105                 110

Ile Ile Asn Tyr Ser Gly Val Asn Asn Thr Ala Tyr His Gly Tyr Trp
        115                 120                 125

Ala Arg Asp Phe Lys Lys Thr Asn Pro Ala Tyr Gly Thr Ile Ala Asp
    130                 135                 140

Phe Gln Asn Leu Ile Ala Ala Ala His Ala Lys Asn Ile Lys Val Ile
145                 150                 155                 160

Ile Asp Phe Ala Pro Asn His Thr Ser Pro Ala Ser Ser Asp Gln Pro
                165                 170                 175

Ser Phe Ala Glu Asn Gly Arg Leu Tyr Asp Asn Gly Thr Leu Leu Gly
            180                 185                 190

Gly Tyr Thr Asn Asp Thr Gln Asn Leu Phe His His Asn Gly Gly Thr
        195                 200                 205

Asp Phe Ser Thr Thr Glu Asn Gly Ile Tyr Lys Asn Leu Tyr Asp Leu
    210                 215                 220

Ala Asp Leu Asn His Asn Asn Ser Thr Val Asp Val Tyr Leu Lys Asp
225                 230                 235                 240

Ala Ile Lys Met Trp Leu Asp Leu Gly Ile Asp Gly Ile Arg Met Asp
                245                 250                 255

Ala Val Lys His Met Pro Phe Gly Trp Gln Lys Ser Phe Met Ala Ala
            260                 265                 270

Val Asn Asn Tyr Lys Pro Val Phe Thr Phe Gly Glu Trp Phe Leu Gly
        275                 280                 285

Val Asn Glu Val Ser Pro Glu Asn His Lys Phe Ala Asn Glu Ser Gly
    290                 295                 300

Met Ser Leu Leu Asp Phe Arg Phe Ala Gln Lys Val Arg Gln Val Phe
```

```
                305                 310                 315                 320
Arg Asp Asn Thr Asp Asn Met Tyr Gly Leu Lys Ala Met Leu Glu Gly
                    325                 330                 335

Ser Ala Ala Asp Tyr Ala Gln Val Asp Gln Val Thr Phe Ile Asp
                340                 345                 350

Asn His Asp Met Glu Arg Phe His Ala Ser Asn Ala Asn Arg Arg Lys
                    355                 360                 365

Leu Glu Gln Ala Leu Ala Phe Thr Leu Thr Ser Arg Gly Val Pro Ala
                370                 375                 380

Ile Tyr Tyr Gly Thr Glu Gln Tyr Met Ser Gly Gly Thr Asp Pro Asp
385                 390                 395                 400

Asn Arg Ala Arg Ile Pro Ser Phe Ser Thr Ser Thr Ala Tyr Gln
                    405                 410                 415

Val Ile Gln Lys Leu Ala Pro Leu Arg Lys Cys Asn Pro Ala Ile Ala
                420                 425                 430

Tyr Gly Ser Thr Gln Glu Arg Trp Ile Asn Asn Asp Val Leu Ile Tyr
                    435                 440                 445

Glu Arg Lys Phe Gly Ser Asn Val Ala Val Ala Val Asn Arg Asn
                450                 455                 460

Leu Asn Ala Pro Ala Ser Ile Ser Gly Leu Val Thr Ser Leu Pro Gln
465                 470                 475                 480

Gly Ser Tyr Asn Asp Val Leu Gly Gly Leu Leu Asn Gly Asn Thr Leu
                    485                 490                 495

Ser Val Gly Ser Gly Gly Ala Ala Ser Asn Phe Thr Leu Ala Ala Gly
                500                 505                 510

Gly Thr Ala Val Trp Gln Tyr Thr Ala Ala Thr Ala Thr Pro Thr Ile
                    515                 520                 525

Gly His Val Gly Pro Met Met Ala Lys Pro Gly Val Thr Ile Thr Ile
                530                 535                 540

Asp Gly Arg Gly Phe Gly Ser Ser Lys Gly Thr Val Tyr Phe Gly Thr
545                 550                 555                 560

Thr Ala Val Ser Gly Ala Asp Ile Thr Ser Trp Glu Asp Thr Gln Ile
                    565                 570                 575

Lys Val Lys Ile Pro Ala Val Ala Gly Gly Asn Tyr Asn Ile Lys Val
                580                 585                 590

Ala Asn Ala Ala Gly Thr Ala Ser Asn Val Tyr Asp Asn Phe Glu Val
                    595                 600                 605

Leu Ser Gly Asp Gln Val Ser Val Arg Phe Val Val Asn Asn Ala Thr
610                 615                 620

Thr Ala Leu Gly Gln Asn Val Tyr Leu Thr Gly Ser Val Ser Glu Leu
625                 630                 635                 640

Gly Asn Trp Asp Pro Ala Lys Ala Ile Gly Pro Met Tyr Asn Gln Val
                    645                 650                 655

Val Tyr Gln Tyr Pro Asn Trp Tyr Tyr Asp Val Ser Val Pro Ala Gly
                660                 665                 670

Lys Thr Ile Glu Phe Lys Phe Leu Lys Lys Gln Gly Ser Thr Val Thr
                    675                 680                 685

Trp Glu Gly Gly Ser Asn His Thr Phe Thr Ala Pro Ser Ser Gly Thr
                690                 695                 700

Ala Thr Ile Asn Val Asn Trp Gln Pro
705                 710

<210> SEQ ID NO 12
<211> LENGTH: 686
```

```
<212> TYPE: PRT
<213> ORGANISM: Bacillus species

<400> SEQUENCE: 12

Ala Pro Asp Thr Ser Val Ser Asn Lys Gln Asn Phe Ser Thr Asp Val
1               5                   10                  15

Ile Tyr Gln Ile Phe Thr Asp Arg Phe Ser Asp Gly Asn Pro Ala Asn
            20                  25                  30

Asn Pro Thr Gly Ala Ala Phe Asp Gly Ser Cys Thr Asn Leu Arg Leu
        35                  40                  45

Tyr Cys Gly Gly Asp Trp Gln Gly Ile Ile Asn Lys Ile Asn Asp Gly
    50                  55                  60

Tyr Leu Thr Gly Met Gly Ile Thr Ala Ile Trp Ile Ser Gln Pro Val
65                  70                  75                  80

Glu Asn Ile Tyr Ser Val Ile Asn Tyr Ser Gly Val Asn Asn Thr Ala
                85                  90                  95

Tyr His Gly Tyr Trp Ala Arg Asp Phe Lys Lys Thr Asn Pro Ala Tyr
            100                 105                 110

Gly Thr Met Gln Asp Phe Lys Asn Leu Ile Asp Thr Ala His Ala His
        115                 120                 125

Asn Ile Lys Val Ile Ile Asp Phe Ala Pro Asn His Thr Ser Pro Ala
130                 135                 140

Ser Ser Asp Asp Pro Ser Phe Ala Glu Asn Gly Arg Leu Tyr Asp Asn
145                 150                 155                 160

Gly Asn Leu Leu Gly Gly Tyr Thr Asn Asp Thr Gln Asn Leu Phe His
                165                 170                 175

His Tyr Gly Gly Thr Asp Phe Ser Thr Ile Glu Asn Gly Ile Tyr Lys
            180                 185                 190

Asn Leu Tyr Asp Leu Ala Asp Leu Asn His Asn Asn Ser Ser Val Asp
        195                 200                 205

Val Tyr Leu Lys Asp Ala Ile Lys Met Trp Leu Asp Leu Gly Val Asp
    210                 215                 220

Gly Ile Arg Val Asp Ala Val Lys His Met Pro Phe Gly Trp Gln Lys
225                 230                 235                 240

Ser Phe Met Ser Thr Ile Asn Asn Tyr Lys Pro Val Phe Thr Phe Gly
                245                 250                 255

Glu Trp Phe Leu Gly Val Asn Glu Ile Ser Pro Glu Tyr His Gln Phe
            260                 265                 270

Ala Asn Glu Ser Gly Met Ser Leu Leu Asp Phe Arg Phe Ala Gln Lys
        275                 280                 285

Ala Arg Gln Val Phe Arg Asp Asn Thr Asp Asn Met Tyr Gly Leu Lys
    290                 295                 300

Ala Met Leu Glu Gly Ser Glu Val Asp Tyr Ala Gln Val Asn Asp Gln
305                 310                 315                 320

Val Thr Phe Ile Asp Asn His Asp Met Glu Arg Phe His Thr Ser Asn
                325                 330                 335

Gly Asp Arg Arg Lys Leu Glu Gln Ala Leu Ala Phe Thr Leu Thr Ser
            340                 345                 350

Arg Gly Val Pro Ala Ile Tyr Tyr Gly Ser Glu Gln Tyr Met Ser Gly
        355                 360                 365

Gly Asn Asp Pro Asp Asn Arg Ala Arg Ile Pro Ser Phe Ser Thr Thr
    370                 375                 380

Thr Thr Ala Tyr Gln Val Ile Gln Lys Leu Ala Pro Leu Arg Lys Ser
385                 390                 395                 400
```

-continued

Asn Pro Ala Ile Ala Tyr Gly Ser Thr Gln Glu Arg Trp Ile Asn Asn
                405                 410                 415

Asp Val Ile Ile Tyr Glu Arg Lys Phe Gly Asn Val Ala Val Val
            420                 425                 430

Ala Ile Asn Arg Asn Met Asn Thr Pro Ala Ser Ile Thr Gly Leu Val
        435                 440                 445

Thr Ser Leu Pro Gln Gly Ser Tyr Asn Asp Val Leu Gly Gly Ile Leu
    450                 455                 460

Asn Gly Asn Thr Leu Thr Val Gly Ala Gly Ala Ala Ser Asn Phe
465                 470                 475                 480

Thr Leu Ala Pro Gly Gly Thr Ala Val Trp Gln Tyr Thr Asp Ala
                485                 490                 495

Thr Ala Pro Ile Ile Gly Asn Val Gly Pro Met Met Ala Lys Pro Gly
            500                 505                 510

Val Thr Ile Thr Ile Asp Gly Arg Gly Phe Gly Ser Gly Lys Gly Thr
        515                 520                 525

Val Tyr Phe Gly Thr Thr Ala Val Thr Gly Ala Asp Ile Val Ala Trp
    530                 535                 540

Glu Asp Thr Gln Ile Gln Val Lys Ile Pro Ala Val Pro Gly Gly Ile
545                 550                 555                 560

Tyr Asp Ile Arg Val Ala Asn Ala Ala Gly Ala Ala Ser Asn Ile Tyr
                565                 570                 575

Asp Asn Phe Glu Val Leu Thr Gly Asp Gln Val Thr Val Arg Phe Val
            580                 585                 590

Ile Asn Asn Ala Thr Thr Ala Leu Gly Gln Asn Val Phe Leu Thr Gly
        595                 600                 605

Asn Val Ser Glu Leu Gly Asn Trp Asp Pro Asn Ala Ile Gly Pro
    610                 615                 620

Met Tyr Asn Gln Val Val Tyr Gln Tyr Pro Thr Trp Tyr Tyr Asp Val
625                 630                 635                 640

Ser Val Pro Ala Gly Gln Thr Ile Glu Phe Lys Phe Leu Lys Lys Gln
                645                 650                 655

Gly Ser Thr Val Thr Trp Glu Gly Gly Ala Asn Arg Thr Phe Thr Thr
            660                 665                 670

Pro Thr Ser Gly Thr Ala Thr Met Asn Val Asn Trp Gln Pro
        675                 680                 685

<210> SEQ ID NO 13
<211> LENGTH: 704
<212> TYPE: PRT
<213> ORGANISM: Bacillus ohbensis

<400> SEQUENCE: 13

Met Lys Asn Leu Thr Val Leu Leu Lys Thr Ile Pro Leu Ala Leu Leu
1               5                   10                  15

Leu Phe Ile Leu Leu Ser Leu Pro Thr Ala Ala Gln Ala Asp Val Thr
            20                  25                  30

Asn Lys Val Asn Tyr Thr Arg Asp Val Ile Tyr Gln Ile Val Thr Asp
        35                  40                  45

Arg Phe Ser Asp Gly Asp Pro Ser Asn Asn Pro Thr Gly Ala Ile Tyr
    50                  55                  60

Ser Gln Asp Cys Ser Asp Leu His Lys Tyr Cys Gly Gly Asp Trp Gln
65                  70                  75                  80

Gly Ile Ile Asp Lys Ile Asn Asp Gly Tyr Leu Thr Asp Leu Gly Ile
                85                  90                  95

-continued

Thr Ala Ile Trp Ile Ser Gln Pro Val Glu Asn Val Tyr Ala Leu His
            100                 105                 110

Pro Ser Gly Tyr Thr Ser Tyr His Gly Tyr Trp Ala Arg Asp Tyr Lys
            115                 120                 125

Arg Thr Asn Pro Phe Tyr Gly Asp Phe Ser Asp Phe Asp Arg Leu Met
130                 135                 140

Asp Thr Ala His Ser Asn Gly Ile Lys Val Ile Met Asp Phe Thr Pro
145                 150                 155                 160

Asn His Ser Ser Pro Ala Leu Glu Thr Asp Pro Ser Tyr Ala Glu Asn
                165                 170                 175

Gly Ala Val Tyr Asn Asp Gly Val Leu Ile Gly Asn Tyr Ser Asn Asp
            180                 185                 190

Pro Asn Asn Leu Phe His His Asn Gly Gly Thr Asp Phe Ser Ser Tyr
            195                 200                 205

Glu Asp Ser Ile Tyr Arg Asn Leu Tyr Asp Leu Ala Asp Tyr Asp Leu
    210                 215                 220

Asn Asn Thr Val Met Asp Gln Tyr Leu Lys Glu Ser Ile Lys Leu Trp
225                 230                 235                 240

Leu Asp Lys Gly Ile Asp Gly Ile Arg Val Asp Ala Val Lys His Met
                245                 250                 255

Ser Glu Gly Trp Gln Thr Ser Leu Met Ser Asp Ile Tyr Ala His Glu
            260                 265                 270

Pro Val Phe Thr Phe Gly Glu Trp Phe Leu Gly Ser Gly Glu Val Asp
            275                 280                 285

Pro Gln Asn His His Phe Ala Asn Glu Ser Gly Met Ser Leu Leu Asp
            290                 295                 300

Phe Gln Phe Gly Gln Thr Ile Arg Asp Val Leu Met Asp Gly Ser Ser
305                 310                 315                 320

Asn Trp Tyr Asp Phe Asn Glu Met Ile Ala Ser Thr Glu Glu Asp Tyr
                325                 330                 335

Asp Glu Val Ile Asp Gln Val Thr Phe Ile Asp Asn His Asp Met Ser
            340                 345                 350

Arg Phe Ser Phe Glu Gln Ser Ser Asn Arg His Thr Asp Ile Ala Leu
            355                 360                 365

Ala Val Leu Leu Thr Ser Arg Gly Val Pro Thr Ile Tyr Tyr Gly Thr
            370                 375                 380

Glu Gln Tyr Leu Thr Gly Gly Asn Asp Pro Glu Asn Arg Lys Pro Met
385                 390                 395                 400

Ser Asp Phe Asp Arg Thr Thr Asn Ser Tyr Gln Ile Ile Ser Thr Leu
                405                 410                 415

Ala Ser Leu Arg Gln Asn Asn Pro Ala Leu Gly Tyr Gly Asn Thr Ser
            420                 425                 430

Glu Arg Trp Ile Asn Ser Asp Val Tyr Ile Tyr Glu Arg Ser Phe Gly
            435                 440                 445

Asp Ser Val Val Leu Thr Ala Val Asn Ser Gly Asp Thr Ser Tyr Thr
            450                 455                 460

Ile Asn Asn Leu Asn Thr Ser Leu Pro Gln Gly Gln Tyr Thr Asp Glu
465                 470                 475                 480

Leu Gln Gln Leu Leu Asp Gly Asn Glu Ile Thr Val Asn Ser Asn Gly
                485                 490                 495

Ala Val Asp Ser Phe Gln Leu Ser Ala Asn Gly Val Ser Val Trp Gln
            500                 505                 510

Ile Thr Glu Glu His Ala Ser Pro Leu Ile Gly His Val Gly Pro Met
            515                 520                 525

```
Met Gly Lys His Gly Asn Thr Val Thr Ile Thr Gly Glu Gly Phe Gly
    530                 535                 540

Asp Asn Glu Gly Ser Val Leu Phe Asp Ser Asp Phe Ser Asp Val Leu
545                 550                 555                 560

Ser Trp Ser Asp Thr Lys Ile Glu Val Ser Val Pro Asp Val Thr Ala
                565                 570                 575

Gly His Tyr Asp Ile Ser Val Val Asn Ala Gly Asp Ser Gln Ser Pro
                580                 585                 590

Thr Tyr Asp Lys Phe Glu Val Leu Thr Gly Asp Gln Val Ser Ile Arg
                595                 600                 605

Phe Ala Val Asn Asn Ala Thr Thr Ser Leu Gly Thr Asn Leu Tyr Met
610                 615                 620

Val Gly Asn Val Asn Glu Leu Gly Asn Trp Asp Pro Asp Gln Ala Ile
625                 630                 635                 640

Gly Pro Met Phe Asn Gln Val Met Tyr Gln Tyr Pro Thr Trp Tyr Tyr
                645                 650                 655

Asp Ile Ser Val Pro Ala Glu Glu Asn Leu Glu Tyr Lys Phe Ile Lys
                660                 665                 670

Lys Asp Ser Ser Gly Asn Val Val Trp Glu Ser Gly Asn Asn His Thr
                675                 680                 685

Tyr Thr Thr Pro Ala Thr Gly Thr Asp Thr Val Leu Val Asp Trp Gln
690                 695                 700

<210> SEQ ID NO 14
<211> LENGTH: 703
<212> TYPE: PRT
<213> ORGANISM: Bacillus species

<400> SEQUENCE: 14

Met Asn Asp Leu Asn Asp Phe Leu Lys Thr Ile Leu Leu Ser Phe Ile
1               5                   10                  15

Phe Phe Leu Leu Leu Ser Leu Pro Thr Val Ala Glu Ala Asp Val Thr
                20                  25                  30

Asn Lys Val Asn Tyr Ser Lys Asp Val Ile Tyr Gln Ile Val Thr Asp
                35                  40                  45

Arg Phe Ser Asp Gly Asn Pro Gly Asn Asn Pro Ser Gly Ala Ile Phe
            50                  55                  60

Ser Gln Asn Cys Ile Asp Leu His Lys Tyr Cys Gly Gly Asp Trp Gln
65              70                  75                  80

Gly Ile Ile Asp Lys Ile Asn Asp Gly Tyr Leu Thr Asp Leu Gly Ile
                85                  90                  95

Thr Ala Leu Trp Ile Ser Gln Pro Val Glu Asn Val Tyr Ala Leu His
                100                 105                 110

Pro Ser Gly Tyr Thr Ser Tyr His Gly Tyr Trp Ala Arg Asp Tyr Lys
            115                 120                 125

Lys Thr Asn Pro Tyr Tyr Gly Asn Phe Asp Asp Phe Asp Arg Leu Met
        130                 135                 140

Ser Thr Ala His Ser Asn Gly Ile Lys Val Ile Met Asp Phe Thr Pro
145             150                 155                 160

Asn His Ser Ser Pro Ala Leu Glu Thr Asn Pro Asn Tyr Val Glu Asn
                165                 170                 175

Gly Ala Ile Tyr Asp Asn Gly Ala Leu Leu Gly Asn Tyr Ser Asn Asp
            180                 185                 190

Gln Gln Asn Leu Phe His His Asn Gly Gly Thr Asp Phe Ser Ser Tyr
        195                 200                 205
```

```
Glu Asp Ser Ile Tyr Arg Asn Leu Tyr Asp Leu Ala Asp Tyr Asp Leu
    210                 215                 220

Asn Asn Thr Val Met Asp Gln Tyr Leu Lys Glu Ser Ile Lys Phe Trp
225                 230                 235                 240

Leu Asp Lys Gly Ile Asp Gly Ile Arg Val Asp Ala Val Lys His Met
                245                 250                 255

Ser Glu Gly Trp Gln Thr Ser Leu Met Ser Glu Ile Tyr Ser His Lys
            260                 265                 270

Pro Val Phe Thr Phe Gly Glu Trp Phe Leu Gly Ser Gly Glu Val Asp
        275                 280                 285

Pro Gln Asn His His Phe Ala Asn Glu Ser Gly Met Ser Leu Leu Asp
    290                 295                 300

Phe Gln Phe Gly Gln Thr Ile Arg Asn Val Leu Lys Asp Arg Thr Ser
305                 310                 315                 320

Asn Trp Tyr Asp Phe Asn Glu Met Ile Thr Ser Thr Glu Lys Glu Tyr
                325                 330                 335

Asn Glu Val Ile Asp Gln Val Thr Phe Ile Asp Asn His Asp Met Ser
            340                 345                 350

Arg Phe Ser Val Gly Ser Ser Asn Arg Gln Thr Asp Met Ala Leu
        355                 360                 365

Ala Val Leu Leu Thr Ser Arg Gly Val Pro Thr Ile Tyr Tyr Gly Thr
370                 375                 380

Glu Gln Tyr Val Thr Gly Gly Asn Asp Pro Glu Asn Arg Lys Pro Leu
385                 390                 395                 400

Lys Thr Phe Asp Arg Ser Thr Asn Ser Tyr Gln Ile Ile Ser Lys Leu
                405                 410                 415

Ala Ser Leu Arg Gln Thr Asn Ser Ala Leu Gly Tyr Gly Thr Thr Thr
            420                 425                 430

Glu Arg Trp Leu Asn Glu Asp Ile Tyr Ile Tyr Glu Arg Thr Phe Gly
        435                 440                 445

Asn Ser Ile Val Leu Thr Ala Val Asn Ser Ser Asn Ser Asn Gln Thr
    450                 455                 460

Ile Thr Asn Leu Asn Thr Ser Leu Pro Gln Gly Asn Tyr Thr Asp Glu
465                 470                 475                 480

Leu Gln Gln Arg Leu Asp Gly Asn Thr Ile Thr Val Asn Ala Asn Gly
                485                 490                 495

Ala Val Asn Ser Phe Gln Leu Arg Ala Asn Ser Val Ala Val Trp Gln
            500                 505                 510

Val Ser Asn Pro Ser Thr Ser Pro Leu Ile Gly Gln Val Gly Pro Met
        515                 520                 525

Met Gly Lys Ala Gly Asn Thr Ile Thr Val Ser Gly Glu Gly Phe Gly
    530                 535                 540

Asp Glu Arg Gly Ser Val Leu Phe Asp Ser Thr Ser Ser Glu Ile Ile
545                 550                 555                 560

Ser Trp Ser Asn Thr Lys Ile Ser Val Lys Val Pro Asn Val Ala Gly
                565                 570                 575

Gly Tyr Tyr Asp Leu Ser Val Val Thr Ala Ala Asn Ile Lys Ser Pro
            580                 585                 590

Thr Tyr Lys Glu Phe Glu Val Leu Ser Gly Asn Gln Val Ser Val Arg
        595                 600                 605

Phe Gly Val Asn Asn Ala Thr Thr Ser Pro Gly Thr Asn Leu Tyr Ile
    610                 615                 620

Val Gly Asn Val Asn Glu Leu Gly Asn Trp Asp Ala Asp Lys Ala Ile
```

```
                625                 630                 635                 640
Gly Pro Met Phe Asn Gln Val Met Tyr Gln Tyr Pro Thr Trp Tyr Tyr
                    645                 650                 655

Asp Ile Ser Val Pro Ala Gly Lys Asn Leu Glu Tyr Lys Tyr Ile Lys
                660                 665                 670

Lys Asp Gln Asn Gly Asn Val Val Trp Gln Ser Gly Asn Asn Arg Thr
                675                 680                 685

Tyr Thr Ser Pro Thr Thr Gly Thr Asp Thr Val Met Ile Asn Trp
                690                 695                 700

<210> SEQ ID NO 15
<211> LENGTH: 711
<212> TYPE: PRT
<213> ORGANISM: Bacillus stearothermophilus

<400> SEQUENCE: 15

Met Arg Arg Trp Leu Ser Leu Val Leu Ser Met Ser Phe Val Phe Ser
1               5                   10                  15

Ala Ile Phe Ile Val Ser Asp Thr Gln Lys Val Thr Val Glu Ala Ala
                20                  25                  30

Gly Asn Leu Asn Lys Val Asn Phe Thr Ser Asp Val Val Tyr Gln Ile
                35                  40                  45

Val Val Asp Arg Phe Val Asp Gly Asn Thr Ser Asn Asn Pro Ser Gly
            50                  55                  60

Ala Leu Phe Ser Ser Gly Cys Thr Asn Leu Arg Lys Tyr Cys Gly Gly
65                  70                  75                  80

Asp Trp Gln Gly Ile Ile Asn Lys Ile Asn Asp Gly Tyr Leu Thr Asp
                85                  90                  95

Met Gly Val Thr Ala Ile Trp Ile Ser Gln Pro Val Glu Asn Val Phe
                100                 105                 110

Ser Val Met Asn Asp Ala Ser Gly Ser Ala Ser Tyr His Gly Tyr Trp
                115                 120                 125

Ala Arg Asp Phe Lys Lys Pro Asn Pro Phe Phe Gly Thr Leu Ser Asp
            130                 135                 140

Phe Gln Arg Leu Val Asp Ala Ala His Ala Lys Gly Ile Lys Val Ile
145                 150                 155                 160

Ile Asp Phe Ala Pro Asn His Thr Ser Pro Ala Ser Glu Thr Asn Pro
                165                 170                 175

Ser Tyr Met Glu Asn Gly Arg Leu Tyr Asp Asn Gly Thr Leu Leu Gly
                180                 185                 190

Gly Tyr Thr Asn Asp Ala Asn Met Tyr Phe His His Asn Gly Gly Thr
                195                 200                 205

Thr Phe Ser Ser Leu Glu Asp Gly Ile Tyr Arg Asn Leu Phe Asp Leu
            210                 215                 220

Ala Asp Leu Asn His Gln Asn Pro Val Ile Asp Arg Tyr Leu Lys Asp
225                 230                 235                 240

Ala Val Lys Met Trp Ile Asp Met Gly Ile Asp Gly Ile Arg Met Asp
                245                 250                 255

Ala Val Lys His Met Pro Phe Gly Trp Gln Lys Ser Leu Met Asp Glu
                260                 265                 270

Ile Asp Asn Tyr Arg Pro Val Phe Thr Phe Gly Glu Trp Phe Leu Ser
                275                 280                 285

Glu Asn Glu Val Asp Ala Asn Asn His Tyr Phe Ala Asn Glu Ser Gly
            290                 295                 300

Met Ser Leu Leu Asp Phe Arg Phe Gly Gln Lys Leu Arg Gln Val Leu
```

```
                305                 310                 315                 320
Arg Asn Asn Ser Asp Asn Trp Tyr Gly Phe Asn Gln Met Ile Gln Asp
            325                 330                 335

Thr Ala Ser Ala Tyr Asp Glu Val Leu Asp Gln Val Thr Phe Ile Asp
            340                 345                 350

Asn His Asp Met Asp Arg Phe Met Ile Asp Gly Gly Asp Pro Arg Lys
            355                 360                 365

Val Asp Met Ala Leu Ala Val Leu Leu Thr Ser Arg Gly Val Pro Asn
            370                 375                 380

Ile Tyr Tyr Gly Thr Glu Gln Tyr Met Thr Gly Asn Gly Asp Pro Asn
385                 390                 395                 400

Asn Arg Lys Met Met Ser Ser Phe Asn Lys Asn Thr Arg Ala Tyr Gln
            405                 410                 415

Val Ile Gln Lys Leu Ser Ser Leu Arg Arg Asn Asn Pro Ala Leu Ala
            420                 425                 430

Tyr Gly Asp Thr Glu Gln Arg Trp Ile Asn Gly Asp Val Tyr Val Tyr
            435                 440                 445

Glu Arg Gln Phe Gly Lys Asp Val Val Leu Val Ala Val Asn Arg Ser
            450                 455                 460

Ser Ser Ser Asn Tyr Ser Ile Thr Gly Leu Phe Thr Ala Leu Pro Ala
465                 470                 475                 480

Gly Thr Tyr Thr Asp Gln Leu Gly Gly Leu Leu Asp Gly Asn Thr Ile
            485                 490                 495

Gln Val Gly Ser Asn Gly Ser Val Asn Ala Phe Asp Leu Gly Pro Gly
            500                 505                 510

Glu Val Gly Val Trp Ala Tyr Ser Ala Thr Glu Ser Thr Pro Ile Ile
            515                 520                 525

Gly His Val Gly Pro Met Met Gly Gln Val Gly His Gln Val Thr Ile
            530                 535                 540

Asp Gly Glu Gly Phe Gly Thr Asn Thr Gly Thr Val Lys Phe Gly Thr
545                 550                 555                 560

Thr Ala Ala Asn Val Val Ser Trp Ser Asn Asn Gln Ile Val Val Ala
            565                 570                 575

Val Pro Asn Val Ser Pro Gly Lys Tyr Asn Ile Thr Val Gln Ser Ser
            580                 585                 590

Ser Gly Gln Thr Ser Ala Ala Tyr Asp Asn Phe Glu Val Leu Thr Asn
            595                 600                 605

Asp Gln Val Ser Val Arg Phe Val Val Asn Asn Ala Thr Thr Asn Leu
            610                 615                 620

Gly Gln Asn Ile Tyr Ile Val Gly Asn Val Tyr Glu Leu Gly Asn Trp
625                 630                 635                 640

Asp Thr Ser Lys Ala Ile Gly Pro Met Phe Asn Gln Val Val Tyr Ser
            645                 650                 655

Tyr Pro Thr Trp Tyr Ile Asp Val Ser Val Pro Glu Gly Lys Thr Ile
            660                 665                 670

Glu Phe Lys Phe Ile Lys Lys Asp Ser Gln Gly Asn Val Thr Trp Glu
            675                 680                 685

Ser Gly Ser Asn His Val Tyr Thr Thr Pro Thr Asn Thr Thr Gly Lys
            690                 695                 700

Ile Ile Val Asp Trp Gln Asn
705                 710

<210> SEQ ID NO 16
<211> LENGTH: 655
```

```
<212> TYPE: PRT
<213> ORGANISM: Klebsiella pneumoniae

<400> SEQUENCE: 16

Met Lys Arg Asn Arg Phe Phe Asn Thr Ser Ala Ala Ile Ala Ile Ser
1               5                   10                  15

Ile Ala Leu Asn Thr Phe Phe Cys Ser Met Gln Thr Ile Ala Ala Glu
                20                  25                  30

Pro Glu Glu Thr Tyr Leu Asp Phe Arg Lys Glu Thr Ile Tyr Phe Leu
            35                  40                  45

Phe Leu Asp Arg Phe Ser Asp Gly Asp Pro Ser Asn Asn Ala Gly Phe
        50                  55                  60

Asn Ser Ala Thr Tyr Asp Pro Asn Asn Leu Lys Lys Tyr Thr Gly Gly
65                  70                  75                  80

Asp Leu Arg Gly Leu Ile Asn Lys Leu Pro Tyr Leu Lys Ser Leu Gly
                85                  90                  95

Val Thr Ser Ile Trp Ile Thr Pro Pro Ile Asp Asn Val Asn Asn Thr
            100                 105                 110

Asp Ala Ala Gly Asn Thr Gly Tyr His Gly Tyr Trp Gly Arg Asp Tyr
        115                 120                 125

Phe Arg Ile Asp Glu His Phe Gly Asn Leu Asp Phe Lys Glu Leu
130                 135                 140

Thr Ser Leu Met His Ser Pro Asp Tyr Asn Met Lys Leu Val Leu Asp
145                 150                 155                 160

Tyr Ala Pro Asn His Ser Asn Ala Asn Asp Glu Asn Glu Phe Gly Ala
                165                 170                 175

Leu Tyr Arg Asp Gly Val Phe Ile Thr Asp Tyr Pro Thr Asn Val Ala
            180                 185                 190

Ala Asn Thr Gly Trp Tyr His His Asn Gly Gly Val Thr Asn Trp Asn
        195                 200                 205

Asp Phe Phe Gln Val Lys Asn His Asn Leu Phe Asn Leu Ser Asp Leu
210                 215                 220

Asn Gln Ser Asn Thr Asp Val Tyr Gln Tyr Leu Leu Asp Gly Ser Lys
225                 230                 235                 240

Phe Trp Ile Asp Ala Gly Val Asp Ala Ile Arg Ile Asp Ala Ile Lys
                245                 250                 255

His Met Asp Lys Ser Phe Ile Gln Lys Trp Thr Ser Asp Ile Tyr Asp
            260                 265                 270

Tyr Ser Lys Ser Ile Gly Arg Glu Gly Phe Phe Phe Gly Glu Trp
        275                 280                 285

Phe Gly Ala Ser Ala Asn Thr Thr Thr Gly Val Asp Gly Asn Ala Ile
290                 295                 300

Asp Tyr Ala Asn Thr Ser Gly Ser Ala Leu Leu Asp Phe Gly Phe Arg
305                 310                 315                 320

Asp Thr Leu Glu Arg Val Leu Val Gly Arg Ser Gly Asn Thr Met Lys
                325                 330                 335

Thr Leu Asn Ser Tyr Leu Ile Lys Arg Gln Thr Val Phe Thr Ser Asp
            340                 345                 350

Asp Trp Gln Val Val Phe Met Asp Asn His Asp Met Ala Arg Ile Gly
        355                 360                 365

Thr Ala Leu Arg Ser Asn Ala Thr Thr Phe Gly Pro Gly Asn Asn Glu
370                 375                 380

Thr Gly Gly Ser Gln Ser Glu Ala Phe Ala Gln Lys Arg Ile Asp Leu
385                 390                 395                 400
```

```
Gly Leu Val Ala Thr Met Thr Val Arg Gly Ile Pro Ala Ile Tyr Tyr
                405                 410                 415

Gly Thr Glu His Tyr Ala Ala Asn Phe Thr Ser Asn Ser Phe Gly Gln
            420                 425                 430

Val Gly Ser Asp Pro Tyr Asn Arg Glu Lys Met Pro Gly Phe Asp Thr
        435                 440                 445

Glu Ser Glu Ala Phe Ser Ile Ile Lys Thr Leu Gly Asp Leu Arg Lys
    450                 455                 460

Ser Ser Pro Ala Ile Gln Asn Gly Thr Tyr Thr Glu Leu Trp Val Asn
465                 470                 475                 480

Asp Asp Ile Leu Val Phe Glu Arg Arg Ser Gly Asn Asp Ile Val Ile
                485                 490                 495

Val Ala Leu Asn Arg Gly Glu Ala Asn Thr Ile Asn Val Lys Asn Ile
            500                 505                 510

Ala Val Pro Asn Gly Val Tyr Pro Ser Leu Ile Gly Asn Asn Ser Val
        515                 520                 525

Ser Val Ala Asn Lys Arg Thr Thr Leu Thr Leu Met Gln Asn Glu Ala
    530                 535                 540

Val Val Ile Arg Ser Gln Ser Asp Asp Ala Glu Asn Pro Thr Val Gln
545                 550                 555                 560

Ser Ile Asn Phe Thr Cys Asn Asn Gly Tyr Thr Ile Ser Gly Gln Ser
                565                 570                 575

Val Tyr Ile Ile Gly Asn Ile Pro Gln Leu Gly Gly Trp Asp Leu Thr
            580                 585                 590

Lys Ala Val Lys Ile Ser Pro Thr Gln Tyr Pro Gln Trp Ser Ala Ser
        595                 600                 605

Leu Glu Leu Pro Ser Asp Leu Asn Val Glu Trp Lys Cys Val Lys Arg
    610                 615                 620

Asn Glu Thr Asn Pro Thr Ala Asn Val Glu Trp Gln Ser Gly Ala Asn
625                 630                 635                 640

Asn Gln Phe Asn Ser Asn Asp Thr Gln Thr Thr Asn Gly Ser Phe
                645                 650                 655

<210> SEQ ID NO 17
<211> LENGTH: 686
<212> TYPE: PRT
<213> ORGANISM: Bacillus stearothermophilus

<400> SEQUENCE: 17

Ser Ser Ser Ala Ser Val Lys Gly Asp Val Ile Tyr Gln Ile Ile
1               5                   10                  15

Asp Arg Phe Tyr Asp Gly Asp Thr Thr Asn Asn Asn Pro Ala Lys Ser
                20                  25                  30

Tyr Gly Leu Tyr Asp Pro Thr Lys Ser Lys Trp Lys Met Tyr Trp Gly
            35                  40                  45

Gly Asp Leu Glu Gly Val Arg Gln Lys Leu Pro Tyr Leu Lys Gln Leu
        50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
            100                 105                 110

Leu Val Asn Asp Ala His Gln Asn Gly Ile Lys Val Ile Val Asp Phe
        115                 120                 125
```

-continued

```
Val Pro Asn His Ser Thr Pro Phe Lys Ala Asn Asp Ser Thr Phe Ala
130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
                180                 185                 190

Gly Phe Ser Leu Ala Asp Leu Ser Gln Glu Asn Gly Thr Ile Ala Gln
                195                 200                 205

Tyr Leu Thr Asp Ala Ala Val Gln Leu Val Ala His Gly Ala Asp Gly
210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
                260                 265                 270

Tyr Ala Asn Asn Ser Gly Val Asn Val Leu Asp Phe Asp Leu Asn Thr
                275                 280                 285

Val Ile Arg Asn Val Phe Gly Thr Phe Thr Gln Thr Met Tyr Asp Leu
290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
                340                 345                 350

Ser Arg Gly Thr Pro Ser Ile Tyr Tyr Gly Thr Glu Gln Tyr Met Ala
                355                 360                 365

Gly Gly Asn Asp Pro Tyr Asn Arg Gly Met Met Pro Ala Phe Asp Thr
                370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Thr Gln Arg Trp Ile Asn
                405                 410                 415

Asn Asp Val Tyr Ile Tyr Glu Arg Lys Phe Phe Asn Asp Val Val Leu
                420                 425                 430

Val Ala Ile Asn Arg Asn Thr Gln Ser Ser Tyr Ser Ile Ser Gly Leu
                435                 440                 445

Gln Thr Ala Leu Pro Asn Gly Ser Tyr Ala Asp Tyr Leu Ser Gly Leu
450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495

Ser Ala Pro Gln Ile Gly Ser Val Ala Pro Asn Met Gly Ile Pro Gly
                500                 505                 510

Asn Val Val Thr Ile Asp Gly Lys Gly Phe Gly Thr Thr Gln Gly Thr
                515                 520                 525

Val Thr Phe Gly Gly Val Thr Ala Thr Val Lys Ser Trp Thr Ser Asn
530                 535                 540

Arg Ile Glu Val Tyr Val Pro Asn Met Ala Ala Gly Leu Thr Asp Val
545                 550                 555                 560
```

```
Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
            580                 585                 590

Pro Thr Asn Leu Gly Asp Lys Ile Tyr Leu Thr Gly Asn Ile Pro Glu
            595                 600                 605

Leu Gly Asn Trp Ser Thr Asp Thr Ser Gly Ala Val Asn Asn Ala Gln
610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
                645                 650                 655

Asp Gly Thr Ile Gln Trp Glu Asn Gly Ser Asn His Val Ala Thr Thr
                660                 665                 670

Pro Thr Gly Ala Thr Gly Asn Ile Thr Val Thr Trp Gln Asn
            675                 680                 685

<210> SEQ ID NO 18
<211> LENGTH: 683
<212> TYPE: PRT
<213> ORGANISM: Bacillus stearothermophilus

<400> SEQUENCE: 18

Ser Ser Ser Ala Ser Val Ser Gly Asp Val Ile Tyr Gln Ile Ile
1               5                   10                  15

Asp Arg Phe Tyr Asp Gly Asp Thr Thr Asn Asn Pro Ala Lys Ser
            20                  25                  30

Tyr Gly Leu Tyr Asp Pro Thr Lys Ser Lys Trp Lys Met Tyr Trp Gly
            35                  40                  45

Gly Asp Leu Glu Gly Val Arg Gln Lys Leu Pro Tyr Leu Lys Gln Leu
50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
            100                 105                 110

Leu Val Asn Asp Ala His Gln Asn Gly Ile Lys Val Ile Val Asp Phe
            115                 120                 125

Val Pro Asn His Ser Thr Pro Phe Lys Ala Asn Asp Ser Thr Phe Ala
130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Ala Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
            195                 200                 205

Tyr Leu Thr Asp Ala Ala Val Gln Leu Val Ala His Gly Ala Asp Gly
            210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255
```

```
Trp Tyr Gly Asp Asp Pro Gly Thr Ala Asn His Leu Glu Lys Val Arg
            260                 265                 270

Tyr Ala Asn Asn Ser Gly Val Asn Val Leu Asp Phe Asp Leu Asn Thr
        275                 280                 285

Val Ile Arg Asn Val Phe Gly Thr Phe Thr Gln Thr Met Tyr Asp Leu
    290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
            340                 345                 350

Ser Arg Gly Thr Pro Ser Ile Tyr Tyr Gly Thr Glu Gln Tyr Met Ala
        355                 360                 365

Gly Gly Asn Asp Pro Tyr Asn Arg Gly Met Met Pro Ala Phe Asp Thr
    370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Thr Gln Arg Trp Ile Asn
                405                 410                 415

Asn Asp Val Tyr Ile Tyr Glu Arg Lys Phe Phe Asn Asp Val Val Leu
            420                 425                 430

Val Ala Ile Asn Arg Asn Thr Gln Ser Ser Tyr Ser Ile Ser Gly Leu
        435                 440                 445

Gln Thr Ala Leu Pro Asn Gly Ser Tyr Ala Asp Tyr Leu Ser Gly Leu
    450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Thr Thr
                485                 490                 495

Asn Pro Pro Leu Ile Gly His Val Gly Pro Thr Met Thr Lys Ala Gly
            500                 505                 510

Gln Thr Ile Thr Ile Asp Gly Arg Gly Phe Gly Thr Thr Ala Gly Gln
        515                 520                 525

Val Leu Phe Gly Thr Thr Pro Ala Thr Ile Val Ser Trp Glu Asp Thr
    530                 535                 540

Glu Val Lys Val Lys Val Pro Ala Leu Thr Pro Gly Lys Tyr Asn Ile
545                 550                 555                 560

Thr Leu Lys Thr Ala Ser Gly Val Thr Ser Asn Ser Tyr Asn Asn Ile
                565                 570                 575

Asn Val Leu Thr Gly Asn Gln Val Cys Val Arg Phe Val Val Asn Asn
            580                 585                 590

Ala Thr Thr Val Trp Gly Glu Asn Val Tyr Leu Thr Gly Asn Val Ala
        595                 600                 605

Glu Leu Gly Asn Trp Asp Thr Ser Lys Ala Ile Gly Pro Met Phe Asn
    610                 615                 620

Gln Val Val Tyr Gln Tyr Pro Thr Trp Tyr Tyr Asp Val Ser Val Pro
625                 630                 635                 640

Ala Gly Thr Thr Ile Glu Phe Lys Phe Ile Lys Lys Asn Gly Ser Thr
                645                 650                 655

Val Thr Trp Glu Gly Gly Tyr Asn His Val Tyr Thr Thr Pro Thr Ser
            660                 665                 670

Gly Thr Ala Thr Val Ile Val Asp Trp Gln Pro
```

<210> SEQ ID NO 19
<211> LENGTH: 686
<212> TYPE: PRT
<213> ORGANISM: Bacillus stearothermophilus

<400> SEQUENCE: 19

```
Ala Pro Asp Thr Ser Val Ser Asn Val Asn Tyr Ser Thr Asp Val
1               5                   10                  15

Ile Tyr Gln Ile Val Thr Asp Arg Phe Leu Asp Gly Asn Pro Ser Asn
                20                  25                  30

Asn Pro Thr Gly Asp Leu Tyr Asp Pro Thr His Thr Ser Leu Lys Lys
            35                  40                  45

Tyr Phe Gly Gly Asp Trp Gln Gly Ile Ile Asn Lys Ile Asn Asp Gly
    50                  55                  60

Tyr Leu Thr Gly Met Gly Ile Thr Ala Ile Trp Ile Ser Gln Pro Val
65                  70                  75                  80

Glu Asn Ile Tyr Ala Val Leu Pro Asp Ser Thr Phe Gly Gly Ser Thr
                85                  90                  95

Ser Tyr His Gly Tyr Trp Ala Arg Asp Phe Lys Lys Thr Asn Pro Phe
            100                 105                 110

Phe Gly Ser Phe Thr Asp Phe Gln Asn Leu Ile Ala Thr Ala His Ala
    115                 120                 125

His Asn Ile Lys Val Ile Ile Asp Phe Ala Pro Asn His Thr Ser Pro
130                 135                 140

Ala Ser Glu Thr Asp Pro Thr Tyr Gly Glu Asn Gly Arg Leu Tyr Asp
145                 150                 155                 160

Asn Gly Val Leu Leu Gly Gly Tyr Thr Asn Asp Thr Asn Gly Tyr Phe
                165                 170                 175

His His Tyr Gly Gly Thr Asn Phe Ser Ser Tyr Glu Asp Gly Ile Tyr
            180                 185                 190

Arg Asn Leu Phe Asp Leu Ala Asp Leu Asp Gln Gln Asn Ser Thr Ile
    195                 200                 205

Asp Ser Tyr Leu Lys Ala Ala Ile Lys Leu Trp Leu Asp Met Gly Ile
210                 215                 220

Asp Gly Ile Arg Met Asp Ala Val Lys His Met Ala Phe Gly Trp Gln
225                 230                 235                 240

Lys Asn Phe Met Asp Ser Ile Leu Ser Tyr Arg Pro Val Phe Thr Phe
                245                 250                 255

Gly Glu Trp Tyr Leu Gly Thr Asn Glu Val Asp Pro Asn Asn Thr Tyr
            260                 265                 270

Phe Ala Asn Glu Ser Gly Met Ser Leu Leu Asp Phe Arg Phe Ala Gln
    275                 280                 285

Lys Val Arg Gln Val Phe Arg Asp Asn Thr Asp Thr Met Tyr Gly Leu
290                 295                 300

Asp Ser Met Ile Gln Ser Thr Ala Ala Asp Tyr Asn Phe Ile Asn Asp
305                 310                 315                 320

Met Val Thr Phe Ile Asp Asn His Asp Met Asp Arg Phe Tyr Thr Gly
                325                 330                 335

Gly Ser Thr Arg Pro Val Glu Gln Ala Leu Ala Phe Thr Leu Thr Ser
            340                 345                 350

Arg Gly Val Pro Ala Ile Tyr Tyr Gly Thr Glu Gln Tyr Met Thr Gly
    355                 360                 365

Asn Gly Asp Pro Tyr Asn Arg Ala Met Met Thr Ser Phe Asp Thr Thr
```

```
            370                 375                 380
Thr Thr Ala Tyr Asn Val Ile Lys Lys Leu Ala Pro Leu Arg Lys Ser
385                 390                 395                 400

Asn Pro Ala Ile Ala Tyr Gly Thr Gln Lys Gln Arg Trp Ile Asn Asn
                405                 410                 415

Asp Val Tyr Ile Tyr Glu Arg Gln Phe Gly Asn Asn Val Ala Leu Val
                420                 425                 430

Ala Ile Asn Arg Asn Leu Ser Thr Ser Tyr Tyr Ile Thr Gly Leu Tyr
                435                 440                 445

Thr Ala Leu Pro Ala Gly Thr Tyr Ser Asp Met Leu Gly Gly Leu Leu
            450                 455                 460

Asn Gly Ser Ser Ile Thr Val Ser Ser Asn Gly Ser Val Thr Pro Phe
465                 470                 475                 480

Thr Leu Ala Pro Gly Glu Val Ala Val Trp Gln Tyr Val Ser Ser Ala
                485                 490                 495

Ser Ala Pro Gln Ile Gly Ser Val Ala Pro Asn Met Gly Ile Pro Gly
                500                 505                 510

Asn Val Val Thr Ile Asp Gly Lys Gly Phe Gly Thr Thr Gln Gly Thr
                515                 520                 525

Val Thr Phe Gly Gly Val Thr Ala Thr Val Lys Ser Trp Thr Ser Asn
            530                 535                 540

Ser Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
                580                 585                 590

Pro Thr Asn Leu Gly Asp Lys Ile Tyr Leu Thr Gly Asn Ile Pro Glu
            595                 600                 605

Leu Gly Asn Trp Ser Thr Asp Thr Ser Gly Ala Val Asn Asn Ala Gln
            610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
                645                 650                 655

Asp Gly Thr Ile Gln Trp Glu Asn Gly Ser Asn His Val Ala Thr Thr
                660                 665                 670

Pro Thr Gly Ala Thr Gly Asn Ile Thr Val Thr Trp Gln Asn
            675                 680                 685

<210> SEQ ID NO 20
<211> LENGTH: 683
<212> TYPE: PRT
<213> ORGANISM: Bacillus stearothermophilus

<400> SEQUENCE: 20

Ser Ser Ser Ala Ser Val Ser Gly Asp Val Ile Tyr Gln Ile Ile
1               5                   10                  15

Asp Arg Phe Tyr Asp Gly Asp Thr Thr Asn Asn Pro Ala Lys Ser
                20                  25                  30

Tyr Gly Leu Tyr Asp Pro Thr Lys Ser Lys Trp Lys Met Tyr Trp Gly
                35                  40                  45

Gly Asp Leu Glu Gly Val Arg Gln Lys Leu Pro Tyr Leu Lys Gln Leu
            50                  55                  60

Gly Val Thr Thr Ile Trp Leu Ser Pro Val Leu Asp Asn Leu Asp Thr
```

-continued

```
            65                  70                  75                  80
        Leu Ala Gly Thr Asp Asn Thr Gly Tyr His Gly Tyr Trp Thr Arg Asp
                            85                  90                  95

Phe Lys Gln Ile Glu Glu His Phe Gly Asn Trp Thr Thr Phe Asp Thr
                            100                 105                 110

Leu Val Asn Asp Ala His Gln Asn Gly Ile Lys Val Ile Val Asp Phe
                            115                 120                 125

Val Pro Asn His Ser Thr Pro Phe Lys Ala Asn Asp Ser Thr Phe Ala
                    130                 135                 140

Glu Gly Gly Ala Leu Tyr Asn Asn Gly Thr Tyr Met Gly Asn Tyr Phe
        145                 150                 155                 160

Asp Asp Ala Thr Lys Gly Tyr Phe His His Asn Gly Asp Ile Ser Asn
                            165                 170                 175

Trp Asp Asp Arg Ala Glu Ala Gln Trp Lys Asn Phe Thr Asp Pro Ala
                        180                 185                 190

Gly Phe Ser Leu Ala Asp Leu Ser Gln Glu Asn Gly Thr Ile Ala Gln
                        195                 200                 205

Tyr Leu Thr Asp Ala Ala Val Gln Leu Val Ala His Gly Ala Asp Gly
            210                 215                 220

Leu Arg Ile Asp Ala Val Lys His Phe Asn Ser Gly Phe Ser Lys Ser
        225                 230                 235                 240

Leu Ala Asp Lys Leu Tyr Gln Lys Lys Asp Ile Phe Leu Val Gly Glu
                        245                 250                 255

Trp Tyr Gly Asp Asp Pro Gly Thr Ala Asn His Leu Glu Lys Val Arg
                    260                 265                 270

Tyr Ala Asn Asn Ser Gly Val Asn Val Leu Asp Phe Asp Leu Asn Thr
                275                 280                 285

Val Ile Arg Asn Val Phe Gly Thr Phe Thr Gln Thr Met Tyr Asp Leu
            290                 295                 300

Asn Asn Met Val Asn Gln Thr Gly Asn Glu Tyr Lys Tyr Lys Glu Asn
        305                 310                 315                 320

Leu Ile Thr Phe Ile Asp Asn His Asp Met Ser Arg Phe Leu Ser Val
                        325                 330                 335

Asn Ser Asn Lys Ala Asn Leu His Gln Ala Leu Ala Phe Ile Leu Thr
                    340                 345                 350

Ser Arg Gly Thr Pro Ser Ile Tyr Tyr Gly Thr Glu Gln Tyr Met Ala
                355                 360                 365

Gly Gly Asn Asp Pro Tyr Asn Arg Gly Met Met Pro Ala Phe Asp Thr
            370                 375                 380

Thr Thr Thr Ala Phe Lys Glu Val Ser Thr Leu Ala Gly Leu Arg Arg
        385                 390                 395                 400

Asn Asn Ala Ala Ile Gln Tyr Gly Thr Thr Thr Gln Arg Trp Ile Asn
                        405                 410                 415

Asn Asp Val Tyr Ile Tyr Glu Arg Lys Phe Phe Asn Asp Val Val Leu
                    420                 425                 430

Val Ala Ile Asn Arg Asn Thr Gln Ser Ser Tyr Ser Ile Ser Gly Leu
                435                 440                 445

Gln Thr Ala Leu Pro Asn Gly Ser Tyr Ala Asp Tyr Leu Ser Gly Leu
            450                 455                 460

Leu Gly Gly Asn Gly Ile Ser Val Ser Asn Gly Ser Val Ala Ser Phe
        465                 470                 475                 480

Thr Leu Ala Pro Gly Ala Val Ser Val Trp Gln Tyr Ser Thr Ser Ala
                        485                 490                 495
```

```
Ser Ala Pro Leu Ile Gly His Val Gly Pro Thr Met Thr Lys Ala Gly
            500                 505                 510

Gln Thr Ile Thr Ile Asp Gly Arg Gly Phe Gly Thr Thr Ala Gly Gln
        515                 520                 525

Val Leu Phe Gly Thr Thr Pro Ala Thr Ile Val Ser Trp Glu Asp Thr
530                 535                 540

Glu Val Lys Val Lys Val Pro Ala Leu Thr Pro Gly Lys Tyr Asn Ile
545                 550                 555                 560

Thr Leu Lys Thr Ala Ser Gly Val Thr Ser Asn Ser Tyr Asn Asn Ile
                565                 570                 575

Asn Val Leu Thr Gly Asn Gln Val Cys Val Arg Phe Val Val Asn Asn
            580                 585                 590

Ala Thr Thr Val Trp Gly Glu Asn Val Tyr Leu Thr Gly Asn Val Ala
        595                 600                 605

Glu Leu Gly Asn Trp Asp Thr Ser Lys Ala Ile Gly Pro Met Phe Asn
    610                 615                 620

Gln Val Val Tyr Gln Tyr Pro Thr Trp Tyr Tyr Asp Val Ser Val Pro
625                 630                 635                 640

Ala Gly Thr Thr Ile Glu Phe Lys Phe Ile Lys Lys Asn Gly Ser Thr
                645                 650                 655

Val Thr Trp Glu Gly Gly Tyr Asn His Val Tyr Thr Thr Pro Thr Ser
            660                 665                 670

Gly Thr Ala Thr Val Ile Val Asp Trp Gln Pro
        675                 680

<210> SEQ ID NO 21
<211> LENGTH: 686
<212> TYPE: PRT
<213> ORGANISM: Bacillus stearothermophilus

<400> SEQUENCE: 21

Ala Pro Asp Thr Ser Val Ser Asn Val Val Asn Tyr Ser Thr Asp Val
1               5                   10                  15

Ile Tyr Gln Ile Val Thr Asp Arg Phe Leu Asp Gly Asn Pro Ser Asn
            20                  25                  30

Asn Pro Thr Gly Asp Leu Tyr Asp Pro Thr His Thr Ser Leu Lys Lys
        35                  40                  45

Tyr Phe Gly Gly Asp Trp Gln Gly Ile Ile Asn Lys Ile Asn Asp Gly
    50                  55                  60

Tyr Leu Thr Gly Met Gly Ile Thr Ala Ile Trp Ile Ser Gln Pro Val
65                  70                  75                  80

Glu Asn Ile Tyr Ala Val Leu Pro Asp Ser Thr Phe Gly Gly Ser Thr
                85                  90                  95

Ser Tyr His Gly Tyr Trp Ala Arg Asp Phe Lys Lys Thr Asn Pro Phe
            100                 105                 110

Phe Gly Ser Phe Thr Asp Phe Gln Asn Leu Ile Ala Thr Ala His Ala
        115                 120                 125

His Asn Ile Lys Val Ile Ile Asp Phe Ala Pro Asn His Thr Ser Pro
    130                 135                 140

Ala Ser Glu Thr Asp Pro Thr Tyr Gly Glu Asn Gly Arg Leu Tyr Asp
145                 150                 155                 160

Asn Gly Val Leu Leu Gly Gly Tyr Thr Asn Asp Thr Asn Gly Tyr Phe
                165                 170                 175

His His Tyr Gly Gly Thr Asn Phe Ser Ser Tyr Glu Asp Gly Ile Tyr
            180                 185                 190
```

```
Arg Asn Leu Phe Asp Leu Ala Asp Leu Asp Gln Gln Asn Ser Thr Ile
        195                 200                 205

Asp Ser Tyr Leu Lys Ala Ala Ile Lys Leu Trp Leu Asp Met Gly Ile
        210                 215                 220

Asp Gly Ile Arg Met Asp Ala Val Lys His Met Ala Phe Gly Trp Gln
225                 230                 235                 240

Lys Asn Phe Met Asp Ser Ile Leu Ser Tyr Arg Pro Val Phe Thr Phe
                245                 250                 255

Gly Glu Trp Tyr Leu Gly Thr Asn Glu Val Asp Pro Asn Asn Thr Tyr
                260                 265                 270

Phe Ala Asn Glu Ser Gly Met Ser Leu Leu Asp Phe Arg Phe Ala Gln
                275                 280                 285

Lys Val Arg Gln Val Phe Arg Asp Asn Thr Asp Thr Met Tyr Gly Leu
        290                 295                 300

Asp Ser Met Ile Gln Ser Thr Ala Ala Asp Tyr Asn Phe Ile Asn Asp
305                 310                 315                 320

Met Val Thr Phe Ile Asp Asn His Asp Met Asp Arg Phe Tyr Thr Gly
                325                 330                 335

Gly Ser Thr Arg Pro Val Glu Gln Ala Leu Ala Phe Thr Leu Thr Ser
                340                 345                 350

Arg Gly Val Pro Ala Ile Tyr Tyr Gly Thr Glu Gln Tyr Met Thr Gly
        355                 360                 365

Asn Gly Asp Pro Tyr Asn Arg Ala Met Met Thr Ser Phe Asp Thr Thr
        370                 375                 380

Thr Thr Ala Tyr Asn Val Ile Lys Lys Leu Ala Pro Leu Arg Lys Ser
385                 390                 395                 400

Asn Pro Ala Ile Ala Tyr Gly Thr Gln Lys Gln Arg Trp Ile Asn Asn
                405                 410                 415

Asp Val Tyr Ile Tyr Glu Arg Gln Phe Gly Asn Asn Val Ala Leu Val
                420                 425                 430

Ala Ile Asn Arg Asn Leu Ser Thr Ser Tyr Tyr Ile Thr Gly Leu Tyr
        435                 440                 445

Thr Ala Leu Pro Ala Gly Thr Tyr Ser Asp Met Leu Gly Gly Leu Leu
        450                 455                 460

Asn Gly Ser Ser Ile Thr Val Ser Ser Asn Gly Ser Val Thr Pro Phe
465                 470                 475                 480

Thr Leu Ala Pro Gly Glu Val Ala Val Trp Gln Tyr Val Ser Thr Thr
                485                 490                 495

Asn Pro Pro Gln Ile Gly Ser Val Ala Pro Asn Met Gly Ile Pro Gly
                500                 505                 510

Asn Val Val Thr Ile Asp Gly Lys Gly Phe Gly Thr Thr Gln Gly Thr
        515                 520                 525

Val Thr Phe Gly Gly Val Thr Ala Thr Val Lys Ser Trp Thr Ser Asn
        530                 535                 540

Ser Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
                580                 585                 590

Pro Thr Asn Leu Gly Asp Lys Ile Tyr Leu Thr Gly Asn Ile Pro Glu
        595                 600                 605

Leu Gly Asn Trp Ser Thr Asp Ser Gly Ala Val Asn Asn Ala Gln
        610                 615                 620
```

```
Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
            645                 650                 655

Asp Gly Thr Ile Gln Trp Glu Asn Gly Ser Asn His Val Ala Thr Thr
                660                 665                 670

Pro Thr Gly Ala Thr Gly Asn Ile Thr Val Thr Trp Gln Asn
        675                 680                 685

<210> SEQ ID NO 22
<211> LENGTH: 684
<212> TYPE: PRT
<213> ORGANISM: Bacillus stearothermophilus

<400> SEQUENCE: 22

Ser Ser Ser Ala Ser Val Ser Gly Asp Val Ile Tyr Gln Ile Ile
1               5                   10                  15

Asp Arg Phe Tyr Asp Gly Asp Thr Thr Asn Asn Pro Ala Lys Ser
                20                  25                  30

Tyr Gly Leu Tyr Asp Pro Thr Lys Ser Lys Trp Lys Met Tyr Trp Gly
            35                  40                  45

Gly Asp Leu Glu Gly Val Arg Gln Lys Leu Pro Tyr Leu Lys Gln Leu
        50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
                100                 105                 110

Leu Val Asn Asp Ala His Gln Asn Gly Ile Lys Val Ile Val Asp Phe
            115                 120                 125

Val Pro Asn His Ser Thr Pro Phe Lys Ala Asn Asp Ser Thr Phe Ala
        130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Ala Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
        195                 200                 205

Tyr Leu Thr Asp Ala Ala Val Gln Leu Val Ala His Gly Ala Asp Gly
        210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
            260                 265                 270

Tyr Ala Asn Asn Ser Gly Val Asn Val Leu Asp Phe Asp Leu Asn Thr
        275                 280                 285

Val Ile Arg Asn Val Phe Gly Thr Phe Thr Gln Thr Met Tyr Asp Leu
        290                 295                 300

Asn Asn Met Val Asn Gln Thr Gly Asn Glu Tyr Lys Tyr Lys Glu Asn
305                 310                 315                 320
```

```
Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
            340                 345                 350

Ser Arg Gly Thr Pro Ser Ile Tyr Tyr Gly Thr Glu Gln Tyr Met Ala
        355                 360                 365

Gly Gly Asn Asp Pro Tyr Asn Arg Gly Met Met Pro Ala Phe Asp Thr
    370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Lys Gln Arg Trp Ile Asn
                405                 410                 415

Asn Asp Val Tyr Ile Tyr Glu Arg Gln Phe Gly Asn Asn Val Ala Leu
            420                 425                 430

Val Ala Ile Asn Arg Asn Leu Ser Thr Ser Tyr Tyr Ile Thr Gly Leu
        435                 440                 445

Tyr Thr Ala Leu Pro Ala Gly Thr Tyr Ser Asp Met Leu Gly Gly Leu
    450                 455                 460

Leu Asn Gly Ser Ser Ile Thr Val Ser Ser Asn Gly Ser Val Thr Pro
465                 470                 475                 480

Phe Thr Leu Ala Pro Gly Glu Val Ala Val Trp Gln Tyr Val Ser Thr
                485                 490                 495

Thr Asn Pro Pro Leu Ile Gly His Val Gly Pro Thr Met Thr Lys Ala
            500                 505                 510

Gly Gln Thr Ile Thr Ile Asp Gly Arg Gly Phe Gly Thr Thr Ala Gly
        515                 520                 525

Gln Val Leu Phe Gly Thr Thr Pro Ala Thr Ile Val Ser Trp Glu Asp
    530                 535                 540

Thr Glu Val Lys Val Lys Val Pro Ala Leu Thr Pro Gly Lys Tyr Asn
545                 550                 555                 560

Ile Thr Leu Lys Thr Ala Ser Gly Val Thr Ser Asn Ser Tyr Asn Asn
                565                 570                 575

Ile Asn Val Leu Thr Gly Asn Gln Val Cys Val Arg Phe Val Val Asn
            580                 585                 590

Asn Ala Thr Thr Val Trp Gly Glu Asn Val Tyr Leu Thr Gly Asn Val
        595                 600                 605

Ala Glu Leu Gly Asn Trp Asp Thr Ser Lys Ala Ile Gly Pro Met Phe
    610                 615                 620

Asn Gln Val Val Tyr Gln Tyr Pro Thr Trp Tyr Tyr Asp Val Ser Val
625                 630                 635                 640

Pro Ala Gly Thr Thr Ile Glu Phe Lys Phe Ile Lys Lys Asn Gly Ser
                645                 650                 655

Thr Val Thr Trp Glu Gly Gly Tyr Asn His Val Tyr Thr Thr Pro Thr
            660                 665                 670

Ser Gly Thr Ala Thr Val Ile Val Asp Trp Gln Pro
        675                 680

<210> SEQ ID NO 23
<211> LENGTH: 684
<212> TYPE: PRT
<213> ORGANISM: Bacillus stearothermophilus

<400> SEQUENCE: 23

Ser Ser Ser Ala Ser Val Ser Gly Asp Val Ile Tyr Gln Ile Ile Ile
1               5                   10                  15
```

```
Asp Arg Phe Tyr Asp Gly Asp Thr Thr Asn Asn Asn Pro Ala Lys Ser
                20                  25                  30

Tyr Gly Leu Tyr Asp Pro Thr Lys Ser Lys Trp Lys Met Tyr Trp Gly
            35                  40                  45

Gly Asp Leu Glu Gly Val Arg Gln Lys Leu Pro Tyr Leu Lys Gln Leu
 50                  55                  60

Gly Val Thr Thr Ile Trp Leu Ser Pro Val Leu Asp Asn Leu Asp Thr
 65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
                100                 105                 110

Leu Val Asn Asp Ala His Gln Asn Gly Ile Lys Val Ile Val Asp Phe
                115                 120                 125

Val Pro Asn His Ser Thr Pro Phe Lys Ala Asn Asp Ser Thr Phe Ala
130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Ala Glu Ala Gln Trp Lys Asn Phe Thr Asp Pro Ala
                180                 185                 190

Gly Phe Ser Leu Ala Asp Leu Ser Gln Glu Asn Gly Thr Ile Ala Gln
                195                 200                 205

Tyr Leu Thr Asp Ala Ala Val Gln Leu Val Ala His Gly Ala Asp Gly
                210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
                260                 265                 270

Tyr Ala Asn Asn Ser Gly Val Asn Val Leu Asp Phe Asp Leu Asn Thr
                275                 280                 285

Val Ile Arg Asn Val Phe Gly Thr Phe Thr Gln Thr Met Tyr Asp Leu
                290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
                340                 345                 350

Ser Arg Gly Thr Pro Ser Ile Tyr Tyr Gly Thr Glu Gln Tyr Met Ala
                355                 360                 365

Gly Gly Asn Asp Pro Tyr Asn Arg Gly Met Met Thr Ser Phe Asp Thr
                370                 375                 380

Thr Thr Thr Ala Tyr Asn Val Ile Lys Lys Leu Ala Pro Leu Arg Lys
385                 390                 395                 400

Ser Asn Pro Ala Ile Ala Tyr Gly Thr Gln Lys Gln Arg Trp Ile Asn
                405                 410                 415

Asn Asp Val Tyr Ile Tyr Glu Arg Gln Phe Gly Asn Asn Val Ala Leu
                420                 425                 430

Val Ala Ile Asn Arg Asn Leu Ser Thr Ser Tyr Tyr Ile Thr Gly Leu
```

```
                435                 440                 445
Tyr Thr Ala Leu Pro Ala Gly Thr Tyr Ser Asp Met Leu Gly Gly Leu
    450                 455                 460

Leu Asn Gly Ser Ser Ile Thr Val Ser Ser Asn Gly Ser Val Thr Pro
465                 470                 475                 480

Phe Thr Leu Ala Pro Gly Glu Val Ala Val Trp Gln Tyr Val Ser Thr
                485                 490                 495

Thr Asn Pro Pro Leu Ile Gly His Val Gly Pro Thr Met Thr Lys Ala
            500                 505                 510

Gly Gln Thr Ile Thr Ile Asp Gly Arg Gly Phe Gly Thr Thr Ala Gly
        515                 520                 525

Gln Val Leu Phe Gly Thr Thr Pro Ala Thr Ile Val Ser Trp Glu Asp
    530                 535                 540

Thr Glu Val Lys Val Lys Val Pro Ala Leu Thr Pro Gly Lys Tyr Asn
545                 550                 555                 560

Ile Thr Leu Lys Thr Ala Ser Gly Val Thr Ser Asn Ser Tyr Asn Asn
                565                 570                 575

Ile Asn Val Leu Thr Gly Asn Gln Val Cys Val Arg Phe Val Val Asn
            580                 585                 590

Asn Ala Thr Thr Val Trp Gly Glu Asn Val Tyr Leu Thr Gly Asn Val
        595                 600                 605

Ala Glu Leu Gly Asn Trp Asp Thr Ser Lys Ala Ile Gly Pro Met Phe
    610                 615                 620

Asn Gln Val Val Tyr Gln Tyr Pro Thr Trp Tyr Tyr Asp Val Ser Val
625                 630                 635                 640

Pro Ala Gly Thr Thr Ile Glu Phe Lys Phe Ile Lys Lys Asn Gly Ser
                645                 650                 655

Thr Val Thr Trp Glu Gly Gly Tyr Asn His Val Tyr Thr Thr Pro Thr
            660                 665                 670

Ser Gly Thr Ala Thr Val Ile Val Asp Trp Gln Pro
        675                 680

<210> SEQ ID NO 24
<211> LENGTH: 681
<212> TYPE: PRT
<213> ORGANISM: Bacillus stearothermophilus

<400> SEQUENCE: 24

Ser Ser Ser Ala Ser Val Ser Gly Asp Val Ile Tyr Gln Ile Ile
1               5                   10                  15

Asp Arg Phe Tyr Asp Gly Asp Thr Thr Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Phe Thr Thr Phe Asp Thr
            100                 105                 110

Leu Val Asn Asp Ala His Gln Asn Gly Ile Lys Val Ile Val Asp Phe
        115                 120                 125

Val Pro Asn His Ser Thr Pro Phe Lys Ala Asn Asp Ser Thr Phe Ala
```

```
                130             135             140
Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
            180                 185                 190

Gly Phe Ser Leu Ala Asp Leu Ser Gln Glu Asn Gly Thr Ile Asp Ser
            195                 200                 205

Tyr Leu Lys Ala Ala Ile Lys Leu Trp Leu Asp Met Gly Ile Asp Gly
        210                 215                 220

Ile Arg Met Asp Ala Val Lys His Met Ala Phe Gly Trp Gln Lys Asn
225                 230                 235                 240

Phe Met Asp Ser Ile Leu Ser Tyr Arg Pro Val Phe Thr Phe Gly Glu
                245                 250                 255

Trp Tyr Leu Gly Thr Asn Glu Val Asp Pro Asn Asn Thr Tyr Phe Ala
            260                 265                 270

Asn Glu Ser Gly Met Ser Leu Leu Asp Phe Arg Phe Ala Gln Lys Val
        275                 280                 285

Arg Gln Val Phe Arg Asp Asn Thr Asp Thr Met Tyr Gly Leu Asp Ser
    290                 295                 300

Met Ile Gln Ser Thr Ala Ala Asp Tyr Asn Phe Ile Asn Asp Met Val
305                 310                 315                 320

Thr Phe Ile Asp Asn His Asp Met Asp Arg Phe Tyr Thr Gly Gly Ser
                325                 330                 335

Thr Arg Pro Val Glu Gln Ala Leu Ala Phe Thr Leu Thr Ser Arg Gly
            340                 345                 350

Val Pro Ala Ile Tyr Tyr Gly Thr Glu Gln Tyr Met Thr Gly Asn Gly
        355                 360                 365

Asp Pro Tyr Asn Arg Ala Met Met Thr Ser Phe Asp Thr Thr Thr Thr
    370                 375                 380

Ala Tyr Asn Val Ile Lys Lys Leu Ala Pro Leu Arg Lys Ser Asn Pro
385                 390                 395                 400

Ala Ile Ala Tyr Gly Thr Gln Lys Gln Arg Trp Ile Asn Asn Asp Val
                405                 410                 415

Tyr Ile Tyr Glu Arg Gln Phe Gly Asn Asn Val Ala Leu Val Ala Ile
            420                 425                 430

Asn Arg Asn Leu Ser Thr Ser Tyr Tyr Ile Thr Gly Leu Tyr Thr Ala
        435                 440                 445

Leu Pro Ala Gly Thr Tyr Ser Asp Met Leu Gly Gly Leu Leu Asn Gly
450                 455                 460

Ser Ser Ile Thr Val Ser Ser Asn Gly Ser Val Thr Pro Phe Thr Leu
465                 470                 475                 480

Ala Pro Gly Glu Val Ala Val Trp Gln Tyr Val Ser Thr Thr Asn Pro
                485                 490                 495

Pro Leu Ile Gly His Val Gly Pro Thr Met Thr Lys Ala Gly Gln Thr
            500                 505                 510

Ile Thr Ile Asp Gly Arg Gly Phe Gly Thr Thr Ala Gly Gln Val Leu
        515                 520                 525

Phe Gly Thr Thr Pro Ala Thr Ile Val Ser Trp Glu Asp Thr Glu Val
    530                 535                 540

Lys Val Lys Val Pro Ala Leu Thr Pro Gly Lys Tyr Asn Ile Thr Leu
545                 550                 555                 560
```

```
Lys Thr Ala Ser Gly Val Thr Ser Asn Ser Tyr Asn Ile Asn Val
                565                 570                 575

Leu Thr Gly Asn Gln Val Cys Val Arg Phe Val Val Asn Asn Ala Thr
            580                 585                 590

Thr Val Trp Gly Glu Asn Val Tyr Leu Thr Gly Asn Val Ala Glu Leu
        595                 600                 605

Gly Asn Trp Asp Thr Ser Lys Ala Ile Gly Pro Met Phe Asn Gln Val
    610                 615                 620

Val Tyr Gln Tyr Pro Thr Trp Tyr Asp Val Ser Val Pro Ala Gly
625                 630                 635                 640

Thr Thr Ile Glu Phe Lys Phe Ile Lys Lys Asn Gly Ser Thr Val Thr
                645                 650                 655

Trp Glu Gly Gly Tyr Asn His Val Tyr Thr Thr Pro Thr Ser Gly Thr
                660                 665                 670

Ala Thr Val Ile Val Asp Trp Gln Pro
            675                 680

<210> SEQ ID NO 25
<211> LENGTH: 690
<212> TYPE: PRT
<213> ORGANISM: Bacillus stearothermophilus

<400> SEQUENCE: 25

Ala Pro Asp Thr Ser Val Ser Asn Val Val Asn Tyr Ser Thr Asp Val
1               5                   10                  15

Ile Tyr Gln Ile Val Thr Asp Arg Phe Leu Asp Gly Asn Pro Ser Asn
            20                  25                  30

Asn Pro Thr Gly Asp Leu Tyr Asp Pro Thr His Thr Ser Leu Lys Lys
        35                  40                  45

Tyr Phe Gly Gly Asp Trp Gln Gly Ile Ile Asn Lys Ile Asn Asp Gly
    50                  55                  60

Tyr Leu Thr Gly Met Gly Ile Thr Ala Ile Trp Ile Ser Gln Pro Val
65                  70                  75                  80

Glu Asn Ile Tyr Ala Val Leu Pro Asp Ser Thr Phe Gly Gly Ser Thr
                85                  90                  95

Ser Tyr His Gly Tyr Trp Ala Arg Asp Phe Lys Lys Thr Asn Pro Phe
            100                 105                 110

Phe Gly Ser Phe Thr Asp Phe Gln Asn Leu Ile Ala Thr Ala His Ala
        115                 120                 125

His Asn Ile Lys Val Ile Ile Asp Phe Ala Pro Asn His Ser Thr Pro
    130                 135                 140

Phe Lys Ala Asn Asp Ser Thr Phe Ala Glu Gly Gly Ala Leu Tyr Asn
145                 150                 155                 160

Asn Gly Thr Tyr Met Gly Asn Tyr Phe Asp Asp Ala Thr Lys Gly Tyr
                165                 170                 175

Phe His His Asn Gly Asp Ile Ser Asn Trp Asp Asp Arg Ala Glu Ala
            180                 185                 190

Gln Trp Lys Asn Phe Thr Asp Pro Ala Gly Phe Ser Leu Ala Asp Leu
        195                 200                 205

Ser Gln Glu Asn Gly Thr Ile Asp Ser Tyr Leu Lys Ala Ala Ile Lys
    210                 215                 220

Leu Trp Leu Asp Met Gly Ile Asp Gly Ile Arg Met Asp Ala Val Lys
225                 230                 235                 240

His Met Ala Phe Gly Trp Gln Lys Asn Phe Met Asp Ser Ile Leu Ser
                245                 250                 255
```

-continued

```
Tyr Arg Pro Val Phe Thr Phe Gly Glu Trp Tyr Leu Gly Thr Asn Glu
            260                 265                 270

Val Asp Pro Asn Asn Thr Tyr Phe Ala Asn Glu Ser Gly Met Ser Leu
            275                 280                 285

Leu Asp Phe Arg Phe Ala Gln Lys Val Arg Gln Val Phe Arg Asp Asn
            290                 295                 300

Thr Asp Thr Met Tyr Gly Leu Asp Ser Met Ile Gln Ser Thr Ala Ala
305                 310                 315                 320

Asp Tyr Asn Phe Ile Asn Asp Met Val Thr Phe Ile Asp Asn His Asp
                    325                 330                 335

Met Asp Arg Phe Tyr Thr Gly Gly Ser Thr Arg Pro Val Glu Gln Ala
            340                 345                 350

Leu Ala Phe Thr Leu Thr Ser Arg Gly Val Pro Ala Ile Tyr Tyr Gly
            355                 360                 365

Thr Glu Gln Tyr Met Thr Gly Asn Gly Asp Pro Tyr Asn Arg Ala Met
            370                 375                 380

Met Thr Ser Phe Asp Thr Thr Thr Ala Tyr Asn Val Ile Lys Lys
385                 390                 395                 400

Leu Ala Pro Leu Arg Lys Ser Asn Pro Ala Ile Ala Tyr Gly Thr Gln
            405                 410                 415

Lys Gln Arg Trp Ile Asn Asn Asp Val Tyr Ile Tyr Glu Arg Gln Phe
            420                 425                 430

Gly Asn Asn Val Ala Leu Val Ala Ile Asn Arg Asn Leu Ser Thr Ser
            435                 440                 445

Tyr Tyr Ile Thr Gly Leu Tyr Thr Ala Leu Pro Ala Gly Thr Tyr Ser
            450                 455                 460

Asp Met Leu Gly Gly Leu Leu Asn Gly Ser Ser Ile Thr Val Ser Ser
465                 470                 475                 480

Asn Gly Ser Val Thr Pro Phe Thr Leu Ala Pro Gly Glu Val Ala Val
            485                 490                 495

Trp Gln Tyr Val Ser Thr Thr Asn Pro Pro Leu Ile Gly His Val Gly
            500                 505                 510

Pro Thr Met Thr Lys Ala Gly Gln Thr Ile Thr Ile Asp Gly Arg Gly
            515                 520                 525

Phe Gly Thr Thr Ala Gly Gln Val Leu Phe Gly Thr Thr Pro Ala Thr
            530                 535                 540

Ile Val Ser Trp Glu Asp Thr Glu Val Lys Val Lys Val Pro Ala Leu
545                 550                 555                 560

Thr Pro Gly Lys Tyr Asn Ile Thr Leu Lys Thr Ala Ser Gly Val Thr
            565                 570                 575

Ser Asn Ser Tyr Asn Asn Ile Asn Val Leu Thr Gly Asn Gln Val Cys
            580                 585                 590

Val Arg Phe Val Val Asn Asn Ala Thr Thr Val Trp Gly Glu Asn Val
            595                 600                 605

Tyr Leu Thr Gly Asn Val Ala Glu Leu Gly Asn Trp Asp Thr Ser Lys
            610                 615                 620

Ala Ile Gly Pro Met Phe Asn Gln Val Val Tyr Gln Tyr Pro Thr Trp
625                 630                 635                 640

Tyr Tyr Asp Val Ser Val Pro Ala Gly Thr Thr Ile Glu Phe Lys Phe
                    645                 650                 655

Ile Lys Lys Asn Gly Ser Thr Val Thr Trp Glu Gly Gly Tyr Asn His
            660                 665                 670

Val Tyr Thr Thr Pro Thr Ser Gly Thr Ala Thr Val Ile Val Asp Trp
            675                 680                 685
```

Gln Pro
    690

<210> SEQ ID NO 26
<211> LENGTH: 269
<212> TYPE: PRT
<213> ORGANISM: Thermomyces lanuginosus

<400> SEQUENCE: 26

Glu Val Ser Gln Asp Leu Phe Asn Gln Phe Asn Leu Phe Ala Gln Tyr
1               5                   10                  15

Ser Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 27
<211> LENGTH: 267
<212> TYPE: PRT
<213> ORGANISM: Fusarium species

<400> SEQUENCE: 27

Ala Val Thr Val Thr Thr Gln Asp Leu Ser Asn Phe Arg Phe Tyr Leu
1               5                   10                  15

Gln His Ala Asp Ala Ala Tyr Cys Asn Phe Asn Thr Ala Val Gly Lys
            20                  25                  30

Pro Val His Cys Gly Ala Gly Asn Cys Pro Asp Ile Glu Lys Asp Ala
        35                  40                  45

```
Ala Ile Val Val Gly Ser Val Gly Thr Lys Thr Gly Ile Gly Ala
    50                  55                  60

Tyr Val Ala Thr Asp Asn Ala Arg Lys Glu Ile Val Ser Val Arg
65                  70                  75                  80

Gly Ser Ile Asn Val Arg Asn Trp Ile Thr Asn Phe Asn Phe Gly Gln
                85                  90                  95

Lys Thr Cys Asp Leu Val Ala Gly Cys Gly Val His Thr Gly Phe Leu
            100                 105                 110

Asp Ala Trp Glu Glu Val Ala Ala Asn Ile Lys Ala Ala Val Ser Ser
            115                 120                 125

Ala Lys Thr Ala Asn Pro Thr Phe Lys Phe Val Val Gly His Ser
    130                 135                 140

Leu Gly Gly Ala Val Ala Thr Val Ala Ala Ala Tyr Leu Arg Lys Asp
145                 150                 155                 160

Gly Phe Pro Phe Asp Leu Tyr Thr Tyr Gly Ser Pro Arg Val Gly Asn
                165                 170                 175

Asp Phe Phe Ala Asn Phe Val Thr Gln Gln Thr Gly Ala Glu Tyr Arg
                180                 185                 190

Val Thr His Gly Asp Asp Pro Val Pro Arg Leu Pro Pro Ile Val Phe
                195                 200                 205

Gly Tyr Arg His Thr Ser Pro Glu Tyr Trp Leu Asp Gly Gly Pro Leu
                210                 215                 220

Asp Lys Asp Tyr Thr Val Ser Glu Ile Lys Val Cys Glu Gly Ile Ala
225                 230                 235                 240

Asn Val Met Cys Asn Gly Gly Thr Ile Gly Leu Asp Ile Leu Ala His
                245                 250                 255

Ile Thr Tyr Phe Gln Ser Met Ala Thr Cys Ala
                260                 265

<210> SEQ ID NO 28
<211> LENGTH: 539
<212> TYPE: PRT
<213> ORGANISM: Coprinus cinereus

<400> SEQUENCE: 28

Met Val Lys Asn Leu Leu Ser Phe Ala Leu Leu Ala Ile Ser Val Ala
1               5                   10                  15

Asn Ala Gln Ile Val Asn Ser Val Asp Thr Met Thr Leu Thr Asn Ala
                20                  25                  30

Asn Val Ser Pro Asp Gly Phe Thr Arg Ala Gly Ile Leu Val Asn Gly
            35                  40                  45

Val His Gly Pro Leu Ile Arg Gly Gly Lys Asn Asp Asn Phe Glu Leu
    50                  55                  60

Asn Val Val Asn Asp Leu Asp Asn Pro Thr Met Leu Arg Pro Thr Ser
65                  70                  75                  80

Ile His Trp His Gly Leu Phe Gln Arg Gly Thr Asn Trp Ala Asp Gly
                85                  90                  95

Ala Asp Gly Val Asn Gln Cys Pro Ile Ser Pro Gly His Ala Phe Leu
            100                 105                 110

Tyr Lys Phe Thr Pro Ala Gly His Ala Gly Thr Phe Trp Tyr His Ser
            115                 120                 125

His Phe Gly Thr Gln Tyr Cys Asp Gly Leu Arg Gly Pro Met Val Ile
    130                 135                 140

Tyr Asp Asp Asn Asp Pro His Ala Ala Leu Tyr Asp Glu Asp Asp Glu
145                 150                 155                 160
```

```
Asn Thr Ile Ile Thr Leu Ala Asp Trp Tyr His Ile Pro Ala Pro Ser
                165                 170                 175
Ile Gln Gly Ala Ala Gln Pro Asp Ala Thr Leu Ile Asn Gly Lys Gly
            180                 185                 190
Arg Tyr Val Gly Gly Pro Ala Ala Glu Leu Ser Ile Val Asn Val Glu
        195                 200                 205
Gln Gly Lys Lys Tyr Arg Met Arg Leu Ile Ser Leu Ser Cys Asp Pro
    210                 215                 220
Asn Trp Gln Phe Ser Ile Asp Gly His Glu Leu Thr Ile Ile Glu Val
225                 230                 235                 240
Asp Gly Gln Leu Thr Glu Pro His Thr Val Asp Arg Leu Gln Ile Phe
                245                 250                 255
Thr Gly Gln Arg Tyr Ser Phe Val Leu Asp Ala Asn Gln Pro Val Asp
            260                 265                 270
Asn Tyr Trp Ile Arg Ala Gln Pro Asn Lys Gly Arg Asn Gly Leu Ala
        275                 280                 285
Gly Thr Phe Ala Asn Gly Val Asn Ser Ala Ile Leu Arg Tyr Ala Gly
    290                 295                 300
Ala Ala Asn Ala Asp Pro Thr Thr Ser Ala Asn Pro Asn Pro Ala Gln
305                 310                 315                 320
Leu Asn Glu Ala Asp Leu His Ala Leu Ile Asp Pro Ala Ala Pro Gly
                325                 330                 335
Ile Pro Thr Pro Gly Ala Ala Asp Val Asn Leu Arg Phe Gln Leu Gly
            340                 345                 350
Phe Ser Gly Gly Arg Phe Thr Ile Asn Gly Thr Ala Tyr Glu Ser Pro
        355                 360                 365
Ser Val Pro Thr Leu Leu Gln Ile Met Ser Gly Ala Gln Ser Ala Asn
    370                 375                 380
Asp Leu Leu Pro Ala Gly Ser Val Tyr Glu Leu Pro Arg Asn Gln Val
385                 390                 395                 400
Val Glu Leu Val Val Pro Ala Gly Val Leu Gly Gly Pro His Pro Phe
                405                 410                 415
His Leu His Gly His Ala Phe Ser Val Val Arg Ser Ala Gly Ser Ser
            420                 425                 430
Thr Tyr Asn Phe Val Asn Pro Val Lys Arg Asp Val Val Ser Leu Gly
        435                 440                 445
Val Thr Gly Asp Glu Val Thr Ile Arg Phe Val Thr Asp Asn Pro Gly
    450                 455                 460
Pro Trp Phe Phe His Cys His Ile Glu Phe His Leu Met Asn Gly Leu
465                 470                 475                 480
Ala Ile Val Phe Ala Glu Asp Met Ala Asn Thr Val Asp Ala Asn Asn
                485                 490                 495
Pro Pro Val Glu Trp Ala Gln Leu Cys Glu Ile Tyr Asp Asp Leu Pro
            500                 505                 510
Pro Glu Ala Thr Ser Ile Gln Thr Val Val Arg Arg Ala Glu Pro Thr
        515                 520                 525
Gly Phe Ser Ala Lys Phe Arg Arg Glu Gly Leu
    530                 535

<210> SEQ ID NO 29
<211> LENGTH: 620
<212> TYPE: PRT
<213> ORGANISM: Myceliophthora thermophila

<400> SEQUENCE: 29
```

```
Met Arg Ser Phe Ile Ser Ala Ala Thr Leu Leu Val Gly Ile Leu Thr
1               5                   10                  15

Pro Ser Val Ala Ala Pro Ser Thr Pro Glu Gln Arg Asp Leu
            20              25              30

Leu Val Pro Ile Thr Glu Arg Glu Ala Ala Val Lys Ala Arg Gln
        35              40              45

Gln Ser Cys Asn Thr Pro Ser Asn Arg Ala Cys Trp Thr Asp Gly Tyr
    50              55              60

Asp Ile Asn Thr Asp Tyr Glu Val Asp Ser Pro Asp Thr Gly Val Val
65              70              75              80

Arg Pro Tyr Thr Leu Thr Leu Thr Glu Val Asp Asn Trp Thr Gly Pro
                85              90              95

Asp Gly Val Val Lys Glu Lys Val Met Leu Val Asn Asn Ser Ile Ile
            100             105             110

Gly Pro Thr Ile Phe Ala Asp Trp Gly Asp Thr Ile Gln Val Thr Val
            115             120             125

Ile Asn Asn Leu Glu Thr Asn Gly Thr Ser Ile His Trp His Gly Leu
130             135             140

His Gln Lys Gly Thr Asn Leu His Asp Gly Ala Asn Gly Ile Thr Glu
145             150             155             160

Cys Pro Ile Pro Pro Lys Gly Gly Arg Lys Val Tyr Arg Phe Lys Ala
                165             170             175

Gln Gln Tyr Gly Thr Ser Trp Tyr His Ser His Phe Ser Ala Gln Tyr
            180             185             190

Gly Asn Gly Val Val Gly Ala Ile Gln Ile Asn Gly Pro Ala Ser Leu
            195             200             205

Pro Tyr Asp Thr Asp Leu Gly Val Phe Pro Ile Ser Asp Tyr Tyr Tyr
210             215             220

Ser Ser Ala Asp Glu Leu Val Glu Leu Thr Lys Asn Ser Gly Ala Pro
225             230             235             240

Phe Ser Asp Asn Val Leu Phe Asn Gly Thr Ala Lys His Pro Glu Thr
                245             250             255

Gly Glu Gly Glu Tyr Ala Asn Val Thr Leu Thr Pro Gly Arg Arg His
            260             265             270

Arg Leu Arg Leu Ile Asn Thr Ser Val Glu Asn His Phe Gln Val Ser
        275             280             285

Leu Val Asn His Thr Met Thr Ile Ile Ala Ala Asp Met Val Pro Val
        290             295             300

Asn Ala Met Thr Val Asp Ser Leu Phe Leu Gly Val Gly Gln Arg Tyr
305             310             315             320

Asp Val Val Ile Glu Ala Ser Arg Thr Pro Gly Asn Tyr Trp Phe Asn
            325             330             335

Val Thr Phe Gly Gly Gly Leu Leu Cys Gly Gly Ser Arg Asn Pro Tyr
            340             345             350

Pro Ala Ala Ile Phe His Tyr Ala Gly Ala Pro Gly Gly Pro Pro Thr
            355             360             365

Asp Glu Gly Lys Ala Pro Val Asp His Asn Cys Leu Asp Leu Pro Asn
        370             375             380

Leu Lys Pro Val Val Ala Arg Asp Val Pro Leu Ser Gly Phe Ala Lys
385             390             395             400

Arg Pro Asp Asn Thr Leu Asp Val Thr Leu Asp Thr Thr Gly Thr Pro
            405             410             415

Leu Phe Val Trp Lys Val Asn Gly Ser Ala Ile Asn Ile Asp Trp Gly
            420             425             430
```

```
Arg Pro Val Val Asp Tyr Val Leu Thr Gln Asn Thr Ser Phe Pro Pro
        435             440             445

Gly Tyr Asn Ile Val Glu Val Asn Gly Ala Asp Gln Trp Ser Tyr Trp
        450             455             460

Leu Ile Glu Asn Asp Pro Gly Ala Pro Phe Thr Leu Pro His Pro Met
465             470             475             480

His Leu His Gly His Asp Phe Tyr Val Leu Gly Arg Ser Pro Asp Glu
        485             490             495

Ser Pro Ala Ser Asn Glu Arg His Val Phe Asp Pro Ala Arg Asp Ala
        500             505             510

Gly Leu Leu Ser Gly Ala Asn Pro Val Arg Arg Asp Val Thr Met Leu
        515             520             525

Pro Ala Phe Gly Trp Val Val Leu Ala Phe Arg Ala Asp Asn Pro Gly
        530             535             540

Ala Trp Leu Phe His Cys His Ile Ala Trp His Val Ser Gly Gly Leu
545             550             555             560

Gly Val Val Tyr Leu Glu Arg Ala Asp Asp Leu Arg Gly Ala Val Ser
            565             570             575

Asp Ala Asp Ala Asp Asp Leu Asp Arg Leu Cys Ala Asp Trp Arg Arg
            580             585             590

Tyr Trp Pro Thr Asn Pro Tyr Pro Lys Ser Asp Ser Gly Leu Lys His
        595             600             605

Arg Trp Val Glu Glu Gly Glu Trp Leu Val Lys Ala
        610             615             620
```